US008728760B2

(12) United States Patent
Galen et al.

(10) Patent No.: US 8,728,760 B2
(45) Date of Patent: May 20, 2014

(54) MICROCIN H47 PLASMID SELECTION SYSTEM

(75) Inventors: James E. Galen, Sykesville, MD (US); Chee-Mun Fang, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 1040 days.

(21) Appl. No.: 12/531,714

(22) PCT Filed: Apr. 3, 2008

(86) PCT No.: PCT/US2008/059214
§ 371 (c)(1),
(2), (4) Date: Oct. 6, 2009

(87) PCT Pub. No.: WO2009/011940
PCT Pub. Date: Jan. 22, 2009

(65) Prior Publication Data
US 2010/0112674 A1     May 6, 2010

Related U.S. Application Data

(60) Provisional application No. 60/907,540, filed on Apr. 6, 2007.

(51) Int. Cl.
*C12P 21/06* (2006.01)
*C07H 21/04* (2006.01)
*C07H 21/02* (2006.01)

(52) U.S. Cl.
USPC .... 435/69.1; 435/243; 435/252.3; 435/320.1; 435/325; 536/23.1; 536/23.7; 536/24.1

(58) Field of Classification Search
USPC ................ 435/69.1, 243, 252.3, 320.1, 325; 536/23.1, 23.7, 24.1
See application file for complete search history.

(56) References Cited

U.S. PATENT DOCUMENTS

| | | |
|---|---|---|
| 6,413,768 B1 | 7/2002 | Galen |
| 6,703,233 B1 | 3/2004 | Galen |
| 7,141,408 B2 | 11/2006 | Galen |

OTHER PUBLICATIONS

Galen et al, Adaptation of the Endogenous *Salmonella enterica* Serovar Typhi clyA-Encoded Hemolysin for Antigen Export Enhances the Immunogenicity of Anthrax Protective Antigen Domain 4 Expressed by the Attenuated Live-Vector Vaccine Strain CVD 908-htrA, *Infection and Immunity*, 2004, vol. 72, No. 12, pp. 7096-7106.
Patzer et al, The Colicin G, H and X Determinants Encode Microcins M and H47, Which Might Utilize the Catecholate Siderophore Receptors FepA, Cir, Fiu, and IroN, *Microbiology*, 2003, vol. 149, pp. 2557-2570.
International Search Report, PCT/US2008/059214, Jul. 23, 2009.
Gaggero, C. et al., Genetic analysis of microcin H47 antibiotic system, Journal of Bacteriology, 1993, vol. 175. No. 17, pp. 5420-5427.
Galan, J. et al., Cloning and characterization of the asd gene of *Salmonella typhimurium*: use in stable maintenance of recombinant plasmids in *Salmonella* vaccine strains, Gene, 1990, vol. 94, pp. 29-35.
Galen, J. et al., Optimization of plasmid maintenance in the attenuated live vector vaccine strain *Salmonella typhi* CVD 908-htrA, Infection and Immunity, 1999, vol. 67, No. 12, pp. 6424-6433.
Pecota, D. et al., Combining the hok/sok, parDE, and pnd postsegregational killer loci to enhance plasmid stability, Applied and Environmental Microbiology, 1997, vol. 63, No. 5, pp. 1917-1924.
Porter, R. et al., L. Use of the *Escherichia coli* ssb gene to prevent bioreactor takeover by plasmidless cells, Biotechnology, 1990, vol. 8, pp. 47-51.
Rodriguez, E. et al. The structural gene for microcin H47 encodes a peptide precursor with antibiotic activity, Antimicrobial Agents and Chemotherapy, 1999. vol. 43, No. 9, pp. 2176-2182.
Williams, K. et al.. Characterization of the structural and functional defect in the *Escherichia coli* single-stranded DNA binding protein encoded by the ssb-1 mutant gene, The Journal of Biological Chemistry, 1984, vol. 259, No. 19, pp. 11804-11811.
Wu, K. et al., Evaluation of the hok/sok killer locus for enhanced plasmid stability, Biotechnology and Bioengineering, 1994: vol. 44, pp. 912-921.
Miller, C. et al., Nucleotide sequence of the partition locus of *Escherichia coli* plasmid pSC101, Gene, 1983, vol. 24, pp. 309-315.
Lavina, M. et al., Microcin H47, a chromosome-encoded microcin antibiotic of *Escherichia coli*, Journal of Bacteriology, 1990, vol. 172, No. 11, pp. 6585-6588.

*Primary Examiner* — Rodney P Swartz
(74) *Attorney, Agent, or Firm* — Roylance, Abrams, Berdo & Goodman, L.L.P.

(57) ABSTRACT

The present invention relates generally to stabilized expression plasmid systems. The stabilized expression plasmid systems comprise an expression vector that includes a plasmid maintenance system (PMS) and, optionally, one or both of a polynucleotide encoding a selected antigen under control of a promoter, and a polynucleotide encoding a selectable marker under control of a promoter. The use of the mchI protein as a selectable marker is found in preferred embodiments of the invention.

28 Claims, 7 Drawing Sheets ssb locus pBRmSSB map pJG-SSB map

US 8,728,760 B2

SEQUENCE LISTING

<160> NUMBER OF SEQ ID NOS: 36

<210> SEQ ID NO 1
<211> LENGTH: 687
<212> TYPE: DNA
<213> ORGANISM: Escherichia coli

<400> SEQUENCE: 1
cctagggcca gcaaaaggcc aggaaccgta aaaaggccgc gttgctggcg tttttccata 60
ggctccgccc ccctgacgag catcacaaaa atcgacgctc aagtcagagg tggcgaaacc 120
cgacaggact ataaagatac caggcgtttc cccctggaag ctccctcgtg cgctctcctg 180
ttccgaccct gccgcttacc ggatacctgt ccgcctttct cccttcggga agcgtggcgc 240
tttctcatag ctcacgctgt aggtatctca gttcggtgta ggtcgttcgc tccaagctgg 300
gctgtgtgca cgaacccccc gttcagcccg accgctgcgc cttatccggt aactatcgtc 360
ttgagtccaa cccggtaaga cacgacttat cgccactggc agcagccact ggtaacagga 420
ttagcagagc gaggtatgta ggcggtgcta cagagttctt gaagtggtgg cctaactacg 480
gctacactag aaggacagta tttggtatct gcgctctgct gaagccagtt accttcggaa 540
aaagagttgg tagctcttga tccggcaaac aaaccaccgc tggtagcggt ggtttttttg 600
tttgcaagca gcagattacg cgcagaaaaa aaggatctca agaagatcct ttgatctttt 660
ctacggggtc tgacgctcag tagatct 687

<210> SEQ ID NO 2
<211> LENGTH: 635
<212> TYPE: DNA
<213> ORGANISM: Escherichia coli

<400> SEQUENCE: 2
cctaggagat acttaacagg gaagtgagag ggccgcggca aagccgtttt tccataggct 60
ccgcccccct gacaagcatc acgaaatctg acgctcaaat cagtggtggc gaaacccgac 120
aggactataa agataccagg cgtttccccc tggcggctcc ctcgtgcgct ctcctgttcc 180
tgcctttcgg tttaccggtg tcattccgct gttatggccg cgtttgtctc attccacgcc 240
tgacactcag ttccgggtag gcagttcgct ccaagctgga ctgtatgcac gaaccccccg 300
ttcagtccga ccgctgcgcc ttatccggta actatcgtct tgagtccaac ccggaaagac 360
atgcaaaagc accactggca gcagccactg gtaattgatt tagaggagtt agtcttgaag 420
tcatgcgccg gttaaggcta aactgaaagg acaagttttg gtgactgcgc tcctccaagc 480
cagttacctc ggttcaaaga gttggtagct cagagaacct tcgaaaaacc gccctgcaag 540
gcggtttttt cgttttcaga gcaagagatt acgcgcagac caaaacgatc tcaagaagat 600
catcttatta atcagataaa atatttctag gatct 635

<210> SEQ ID NO 3

<211> LENGTH: 1955
<212> TYPE: DNA
<213> ORGANISM: Salmonella typhimurium

<400> SEQUENCE: 3

```
cctaggtttc acctgttcta ttaggtgtta catgctgttc atctgttaca ttgtcgatct      60
gttcatggtg aacagcttta aatgcaccaa aaactcgtaa aagctctgat gtatctatct     120
tttttacacc gttttcatct gtgcatatgg acagttttcc ctttgatatc taacggtgaa     180
cagttgttct acttttgttt gttagtcttg atgcttcact gatagataca agagccataa     240
gaacctcaga tccttccgta tttagccagt atgttctcta gtgtggttcg ttgttttgc      300
gtgagccatg agaacgaacc attgagatca tgcttacttt gcatgtcact caaaaatttt     360
gcctcaaaac tggtgagctg aattttgca gttaaagcat cgtgtagtgt ttttcttagt      420
ccgttacgta ggtaggaatc tgatgtaatg gttgttggta ttttgtcacc attcattttt     480
atctggttgt tctcaagttc ggttacgaga tccatttgtc tatctagttc aacttggaaa     540
atcaacgtat cagtcgggcg gcctcgctta tcaaccacca atttcatatt gctgtaagtg     600
tttaaatctt tacttattgg tttcaaaacc cattggttaa gccttttaaa ctcatggtag     660
ttattttcaa gcattaacat gaacttaaat tcatcaaggc taatctctat atttgccttg     720
tgagttttct tttgtgttag ttctttttaat aaccactcat aaatcctcat agagtatttg     780
ttttcaaaag acttaacatg ttccagatta tattttatga attttttttaa ctggaaaaga     840
taaggcaata tctcttcact aaaaactaat tctaattttt cgcttgagaa cttggcatag     900
tttgtccact ggaaaatctc aaagccttta accaaaggat tcctgatttc cacagttctc     960
gtcatcagct ctctggttgc tttagctaat acaccataag catttttccct actgatgttc    1020
atcatctgag cgtattggtt ataagtgaac gataccgtcc gttctttcct tgtagggttt    1080
tcaatcgtgg ggttgagtag tgccacacag cataaaatta gcttggtttc atgctccgtt    1140
aagtcatagc gactaatcgc tagttcattt gctttgaaaa caactaattc agacatacat    1200
ctcaattggt ctaggtgatt ttaatcacta taccaattga gatgggctag tcaatgataa    1260
ttactagtcc tttttccttg agttgtgggt atctgtaaat tctgctagac ctttgctgga    1320
aaacttgtaa attctgctag accctctgta aattccgcta gacctttgtg tgttttttt    1380
gtttatattc aagtggttat aatttataga ataagaaag aataaaaaaa gataaaaaga    1440
atagatccca gccctgtgta taactcacta ctttagtcag ttccgcagta ttacaaaagg    1500
atgtcgcaaa cgctgtttgc tcctctacaa aacagacctt aaaaccctaa aggcttaagt    1560
agcaccctcg caagctcggg caaatcgctg aatattcctt ttgtctccga ccatcaggca    1620
cctgagtcgc tgtctttttc gtgacattca gttcgctgcg ctcacggctc tggcagtgaa    1680
tgggggtaaa tggcactaca ggcgcctttt atggattcat gcaaggaaac tacccataat    1740
acaagaaaag cccgtcacgg gcttctcagg gcgttttatg gcgggtctgc tatgtggtgc    1800
tatctgactt tttgctgttc agcagttcct gccctctgat tttccagtct gaccacttcg    1860
gattatcccg tgacaggtca ttcagactgg ctaatgcacc cagtaaggca gcggtatcat    1920
caacaggctt acccgtctta ctgtcaaccg gatct                               1955
```

<210> SEQ ID NO 4
<211> LENGTH: 734
<212> TYPE: DNA
<213> ORGANISM: Shigella flexneri 2a strain CVD 1208s

<400> SEQUENCE: 4

| catatgattg | acctgaatga | atatacagta | ttggaatgca | ttatccggag | tgttgtgtaa | 60 |
| caatgtctgg | ccaggtttgt | tcccggaac | cgaggtcaca | acatagtaaa | agcgctattg | 120 |
| gtaatggtac | aatcgcgcgt | ttacacttat | tcagaacgac | aggagacacg | aacatggcca | 180 |
| gcagaggcgt | aaacaaggtt | attctcgttg | gtaatctggg | tcaggacccg | gaagtacgct | 240 |
| acatgccaaa | tggtggcgca | gttgccaaca | ttacgctggc | tacttccgaa | tcctggcgtg | 300 |
| ataaagcgac | cggcgagatg | aaagaacaga | ctgaatggca | ccgcgttgtg | ctgttcggca | 360 |
| aactggcaga | agtggcgagc | gaatatctgc | gtaaaggttc | tcaggtttat | atcgaaggtc | 420 |
| agctgcgtac | ccgtaaatgg | accgatcaat | ccggtcagga | tcgctacacc | acagaagtcg | 480 |
| tggtgaacgt | tggcggcacc | atgcagatgc | tgggtggtcg | tcagggtggt | ggcgctccgg | 540 |
| caggtggcaa | tatcggtggt | ggtcagccgc | agggcggttg | gggtcagcct | cagcagccgc | 600 |
| agggtggcaa | tcagttcagc | ggcggcgcgc | agtctcgccc | gcagcagtcc | gctccggcag | 660 |
| cgccgtctaa | cgagccgccg | atggactttg | atgatgacat | tccgttctga | tttgtcatta | 720 |
| aaacaatagc | tagc | | | | | 734 |

<210> SEQ ID NO 5
<211> LENGTH: 1686
<212> TYPE: DNA
<213> ORGANISM: Escherichia coli

<400> SEQUENCE: 5

| cacttttgtt | acccgccaaa | caaaacccaa | aacaaccca | tacccaaccc | aataaaacac | 60 |
| caaaacaaga | caaataatca | ttgattgatg | gttgaaatgg | ggtaaacttg | acaaacaaac | 120 |
| ccacttaaaa | cccaaaacat | acccaaacac | acaccaaaaa | aacaccataa | ggagttttat | 180 |
| aaatgttggt | attcattgat | gacggttcaa | caaacatcaa | actacagtgg | caggaaagcg | 240 |
| acggaacaat | taaacagcac | attagcccga | acagcttcaa | acgcgagtgg | gcagtctctt | 300 |
| ttggtgataa | aaaggtctttt | aactacacac | tgaacggcga | acagtattca | tttgatccaa | 360 |
| tcagcccgga | tgctgtagtc | acaaccaata | tcgcatggca | atacagcgac | gttaatgtcg | 420 |
| ttgcagtgca | tcacgcctta | ctgaccagtg | gtctgccggt | aagcgaagtg | gatattgttt | 480 |
| gcacacttcc | tctgacagag | tattacgaca | gaaataacca | acccaatacg | gaaaatattg | 540 |
| agcgtaagaa | agcaaacttc | cggaaaaaaa | ttacattaaa | tggcggggat | acattcacaa | 600 |
| taaaagatgt | aaaagtcatg | cctgaatcta | taccggcagg | ttatgaagtt | ctacaagaac | 660 |
| tggatgagtt | agattcttta | ttaattatag | atctcgggg | caccacatta | gatatttctc | 720 |
| aggtaatggg | gaaattatcg | gggatcagta | aaatatacgg | agactcatct | cttggtgtct | 780 |
| ctctggttac | atctgcagta | aaagatgccc | tttctcttgc | gagaacaaaa | ggaagtagct | 840 |
| atcttgctga | cgatataatc | attcacagaa | aagataataa | ctatctgaag | caacgaatta | 900 |
| atgatgagaa | caaatatca | aatgtcaccg | aagcaatgaa | tgaagcactt | cgtaaacttg | 960 |
| agcaacgtgt | attaaatacg | ctcaatgaat | tttctggtta | tactcatgtt | atggttatag | 1020 |
| gcggtggcgc | agaattaata | tgcgatgcag | taaaaaaaca | cacacagatt | cgtgatgaac | 1080 |
| gttttttcaa | aaccaataac | tctcaatatg | atttagttaa | cggtatgtat | ctcataggta | 1140 |
| attaatgatg | acaagcgca | gaaccattgc | cttcaaacta | aatccagatg | taaatcaaac | 1200 |
| agataaaatt | gtttgtgata | cactggacag | tatcccgcaa | ggggaacgaa | gccgccttaa | 1260 |
| ccgggccgca | ctgacggcag | gtctggcctt | atacagacaa | gatccccgga | ccccttcct | 1320 |
| tttatgtgag | ctgctgacga | aagaaaccac | attttcagat | atcgtgaata | tattgagatc | 1380 |

```
gctatttcca aaagagatgg ccgattttaa ttcttcaata gtcactcaat cctcttcaca   1440
acaagagcaa aaaagtgatg aagagaccaa aaaaatgcg atgaagctaa taaattaatt   1500
caattattat tgagttccct ttatccacta tcaggctgga taaagggaac tcaatcaagt   1560
tattttctta ccagtcatta cataatcgtt attatgaaat aatcgtttgc actgtctctg   1620
ttattcaggc aatttcaata aaggcacttg ctcacgctct gtcattttct gaaactcttc   1680
atgctg                                                              1686

<210> SEQ ID NO 6
<211> LENGTH: 367
<212> TYPE: DNA
<213> ORGANISM: Escherichia coli

<400> SEQUENCE: 6
gacagtaaga cgggtaagcc tgttgatgat accgctgcct tactgggtgc attagccagt     60
ctgaatgacc tgtcacggga taatccgaag tggtcagact ggaaaatcag agggcaggaa    120
ctgctgaaca gcaaaaagtc agatagcacc acatagcaga cccgccataa aacgccctga    180
gaagcccgtg acgggctttt cttgtattat gggtagtttc cttgcatgaa tccataaaag    240
gcgcctgtag tgccatttac ccccattcac tgccagagcc gtgagcgcag cgaactgaat    300
gtcacgaaaa agacagcgac tcaggtgcct gatggtcgga gacaaaagga atattcagcg    360
atttgcc                                                             367

<210> SEQ ID NO 7
<211> LENGTH: 459
<212> TYPE: DNA
<213> ORGANISM: Escherichia coli

<400> SEQUENCE: 7
ttctgtggta gcacagaata atgaaaagtg tgtaaagaag ggtaaaaaaa accgaatgcg     60
aggcatccgg ttgaaatagg ggtaaacaga cattcagaaa tgaatgacgg taataaataa    120
agttaatgat gatagcggga gttattctag ttgcgagtga aggttttgtt ttgacattca    180
gtgctgtcaa atacttaaga ataagttatt gattttaacc ttgaattatt attgcttgat    240
gttaggtgct tatttcgcca ttccgcaata atcttaaaaa gttcccttgc atttacattt    300
tgaaacatct atagcgataa atgaaacatc ttaaaagttt tagtatcata ttcgtgttgg    360
attattctgc attttggggg agaatggact tgccgactga ttaatgaggg ttaatcagta    420
tgcagtggca taaaaaagca aataaaggca tataacaga                          459

<210> SEQ ID NO 8
<211> LENGTH: 8763
<212> TYPE: DNA
<213> ORGANISM: Artificial Sequence
<220> FEATURE:
<223> OTHER INFORMATION: chemically synthesized plasmid pJG9-SSB
<220> FEATURE:
<221> NAME/KEY: misc_feature
<222> LOCATION: (1508)..(1508)
<223> OTHER INFORMATION: n is a, c, g, or t
<220> FEATURE:
<221> NAME/KEY: misc_feature
<222> LOCATION: (5028)..(5028)
<223> OTHER INFORMATION: n is a, c, g, or t

<400> SEQUENCE: 8
gaattcgccc ttcatatgat tgacctgaat gaatatacag tattggaatg cattatccgg     60
agtgttgtgt aacaatgtct ggccaggttt gtttcccgga accgaggtca caacatagta    120
```

```
aaagcgctat tggtaatggt acaatcgcgc gtttacactt attcagaacg acaggagaca      180
cgaacatggc cagcagaggc gtaaacaagg ttattctcgt tggtaatctg ggtcaggacc      240
cggaagtacg ctacatgcca aatggtggcg cagttgccaa cattacgctg gctacttccg      300
aatcctggcg tgataaagcg accggcgaga tgaaagaaca gactgaatgg caccgcgttg      360
tgctgttcgg caaactggca gaagtggcga gcgaatatct gcgtaaaggt tctcaggttt      420
atatcgaagg tcagctgcgt acccgtaaat ggaccgatca atccggtcag gatcgctaca      480
ccacagaagt cgtggtgaac gttggcggca ccatgcagat gctgggtggt cgtcagggtg      540
gtggcgctcc ggcaggtggc aatatcggtg tggtcagcc gcagggcggt tggggtcagc      600
ctcagcagcc gcagggtggc aatcagttca gcggcggcgc gcagtctcgc ccgcagcagt      660
ccgctccggc agcgccgtct aacgagccgc cgatggactt tgatgatgac attccgttct      720
gatttgtcat taaaacaata gctagtgatg cgcagatctt aatcatccac aggaggcgct      780
accatgagta aaggagaaga acttttcact ggagttgtcc caattcttgt tgaattagat      840
ggtgatgtta atgggcacaa attttctgtc agtggagagg gtgaaggtga tgcaacatac      900
ggaaaactta cccttaaatt tatttgcact actggaaaac tacctgttcc atggccaaca      960
cttgtcacta ctttctctta tggtgttcaa tgcttttccc gttatccgga tcatatgaaa     1020
cggcatgact ttttcaagag tgccatgccc gaaggttatg tacaggaacg cactatatct     1080
ttcaaagatg acgggaacta caagacgcgt gctgaagtca gtttgaagg tgataccctt      1140 gttaatcgta tcgagttaaa aggtattgat tttaaagaag atggaaacat tctcggacac      1200
aaactcgagt acaactataa ctcacacaat gtatacatca cggcagacaa acaaaagaat     1260
ggaatcaaag ctaacttcaa aattcgccac aacattgaag atggatccgt tcaactagca     1320
gaccattatc aacaaaatac tccaattggc gatggccctg tccttttacc agacaaccat     1380
tacctgtcga cacaatctgc cctttcgaaa gatcccaacg aaaagcgtga ccacatggtc     1440
cttcttgagt ttgtaactgc tgctgggatt acacatggca tggatgagct ctacaaataa     1500
tgaactanag agcgctcatg tttgacagct tatcatcgat aagctttaat gcggtagttt     1560
atcacagtta aattgctaac gcagtcaggc accgtgtatg aaatctaaca atgcgctcat     1620
cgtcatcctc ggcaccgtca ccctggatgc tgtaggcata ggcttggtta tgccggtact     1680
gccgggcctc ttgcgggata tcgtccattc cgacagcatc gccagtcact atggcgtgct     1740
gctagcgtcg acactagcaa gggcgaattc gagctcggta cccggggatc cttttttaacc    1800 catcacatat acctgccgtt cactattatt tagtgaaatg agatattatg atattttctg     1860
aattgtgatt aaaaaggcaa ctttatgccc atgcaacaga aactataaaa aatacagaga     1920
atgaaaagaa acagatagat tttttagttc tttaggcccg tagtctgcaa atcctttat      1980 gattttctat caaacaaaag aggaaaatag accagttgca atccaaacga gagtctaata     2040
gaatgaggtc gaaaagtaaa tcgcgcgggt ttgttactga taaagcaggc aagacctaaa     2100
atgtgtaaag ggcaaagtgt atactttggc gtcacccctt acatattta ggtcttttt      2160 tattgtgcgt aactaacttg ccatcttcaa acaggagggc tggaagaagc agaccgctaa     2220
cacagtacat aaaaaggag acatgaacga tgaacatcaa aaagtttgca aaacaagcaa     2280
cagtattaac ctttactacc gcactgctgg caggaggcgc aactcaagcg tttgcgaaag     2340
aaacgaacca aaagccatat aaggaaacat acggcatttc ccatattaca cgccatgata     2400
tgctgcaaat ccctgaacag caaaaaaatg aaaaatataa agttcctgaa ttcgattcgt     2460
ccacaattaa aaatatctct tctgcaaaag gcctggacgt ttgggacagc tggccattac     2520
```

-continued

```
aaaacgctga cggcactgtc gcaaactatc acggctacca catcgtctttt gcattagccg    2580
gagatcctaa aaatgcggat gacacatcga tttacatgtt ctatcaaaaa gtcggcgaaa    2640
cttctattga cagctggaaa aacgctggcc gcgtctttaa agacagcgac aaattcgatg    2700
caaatgattc tatcctaaaa gaccaaacac aagaatggtc aggttcagcc acatttacat    2760
ctgacggaaa aatccgttta ttctacactg atttctccgg taaacattac ggcaaacaaa    2820
cactgacaac tgcacaagtt aacgtatcag catcagacac tctctttgaac atcaacggtg   2880
tagaggatta taaatcaatc tttgacggtg acggaaaaac gtatcaaaat gtacagcagt    2940
tcatcgatga aggcaactac agctcaggcg acaaccatac gctgagagat cctcactacg    3000
tagaagataa aggccacaaa tacttagtat ttgaagcaaa cactggaact gaagatggct    3060
accaaggcga agaatcttta tttaacaaag catactatgg caaaagcaca tcattcttcc    3120
gtcaagaaag tcaaaaactt ctgcaaagcg ataaaaaacg cacggctgag ttagcaaacg    3180
gcgctctcgg tatgattgag ctaaacgatg attacacact gaaaaaagtg atgaaaccgc    3240
tgattgcatc taacacagta acagatgaaa ttgaacgcgc gaacgtcttt aaaatgaacg    3300
gcaaatggta cctgttcact gactcccgcg gatcaaaaat gacgattgac ggcattacgt    3360
ctaacgatat ttacatgctt ggttatgttt ctaattcttt aactggccca tacaagccgc    3420
tgaacaaaac tggccttgtg ttaaaaatgg atcttgatcc taacgatgta acctttactt    3480
actcacactt cgctgtacct caagcgaaag gaaacaatgt cgtgattaca agctatatga    3540
caaacagagg attctacgca gacaaacaat caacgtttgc gccaagcttc ctgctgaaca    3600
tcaaaggcaa gaaaacatct gttgtcaaag acagcatcct tgaacaagga caattaacag    3660
ttaacaaata aaaacgcaaa agaaaatgcc gatatcctat tggcatttttc ttttatttct    3720
tatcaacata aggtgaatcc ccatacctcg agcttcacgc tgccgcaagc actcagggcg    3780
caagggctgc taaaggaag cggaacacgt agaaagccag tccgcagaaa cggtgctgac     3840
cccggatgaa tgtcagctac tgggctatct ggacaaggga aaacgcaagc gcaaagagaa    3900
agcaggtagc ttgcagtggg cttacatggc gatagctaga ctgggcggtt ttatggacag    3960
caagcgaacc ggaattgcca gctggggcgc cctctggtaa ggttgggaag ccctgcaaag    4020
taaactggat ggcttttcttg ccgccaagga tctgatggcg cagggatca agatccccca    4080
gcttggctgt tttggcggat gagagaagat tttcagcctg atacagatta aatcagaacg    4140
cagaagcggt ctgataaaac agaatttgcc tggcggcagt agcgcggtgg tcccacctga    4200
ccccatgccg aactcagaag tgaaacgccg tagcgccgat ggtagtgtgg ggtctcccca    4260
tgcgagagta gggaactgcc aggcatcaaa taaaacgaaa ggctcagtcg aaagactggg    4320
cctttcgttt tatctgttgt ttgtcggtga acgctctcct gagtaggaca aatccgccgg    4380
gagcggattt gaacgttgcg aagcaacggc ccggagggtg gcgggcagga cgcccgccat    4440
aaactgccag gcatcaaatt aagcagaagg ccatcctgac ggatggcctt tttgcgtttc    4500
tacaaactct gggctgcag gcatgcaagc ttgctgcatt aatgaatcgg ccaacgcgcg    4560
gggagaggcg gtttgcgtat tggcaccatt ccttgcggcg gcggtgctca acggcctcaa    4620
cctactactg ggctgcttcc taatgcagga gtcgcataag ggagagcgtc gatccccgac    4680
agtaagacgg gtaagcctgt tgatgatacc gctgccttac tgggtgcatt agccagtctg    4740
aatgacctgt cacgggataa tccgaagtgg tcagactgga aaatcagagg gcaggaactg    4800
ctgaacagca aaagtcaga tagcaccaca tagcagaccc gccataaaac gccctgagaa     4860
gcccgtgacg ggcttttctt gtattatggg tagtttcctt gcatgaatcc ataaaaggcg    4920
```

```
cctgtagtgc catttacccc cattcactgc cagagccgtg agcgcagcga actgaatgtc    4980 acgaaaaga cagcgactca ggtgcctgat ggtcggagac aaaaggganta tattcagcga    5040 tttgcccgag cttgcgaggg tgctacttaa gcctttaggg ttttaaggtc tgttttgtag    5100
aggagcaaac agcgtttgcg acatcctttt gtaatactgc ggaactgact aaagtagtga    5160
gttatacaca gggctgggat ctattctttt tatctttttt tattctttct ttattctata    5220
aattataacc acttgaatat aaacaaaaaa aacacacaaa ggtctagcgg aatttacaga    5280
gggtctagca gaatttacaa gttttccagc aaaggtctag cagaatttac agatacccac    5340
aactcaaagg aaaaggacta gtaattatca ttgactagcc catctcaatt ggtatagtga    5400
ttaaaatcac ctagaccaat tgagatgtat gtctgaatta gttgttttca aagcaaatga    5460
actagcgatt agtcgctatg acttaacgga gcatgaaacc aagctaattt tatgctgtgt    5520
ggcactactc aaccccacga ttgaaaaccc tacaaggaaa gaacggacgg tatcgttcac    5580
ttataaccaa tacgctcaga tgatgaacat cagtagggaa aatgcttatg gtgtattagc    5640
taaagcaacc agagagctga tgacgagaac tgtggaaatc aggaatcctt tggttaaagg    5700
ctttgagatt ttccagtgga caaactatgc caagttctca agcgaaaaat tagaattagt    5760
ttttagtgaa gagatattgc cttatctttt ccagttaaaa aaattcataa aatataatct    5820
ggaacatgtt aagtcttttg aaaacaaata ctctatgagg atttatgagt ggttattaaa    5880
agaactaaca caaagaaaaa ctcacaaggc aaatatagag attagccttg atgaatttaa    5940
gttcatgtta atgcttgaaa ataactacca tgagtttaaa aggcttaacc aatgggtttt    6000
gaaaccaata agtaaagatt taaacactta cagcaatatg aaattggtgg ttgataagcg    6060
aggccgcccg actgatacgt tgattttcca agttgaacta gatagacaaa tggatctcgt    6120
aaccgaactt gagaacaacc agataaaaat gaatggtgac aaaataccaa caaccattac    6180
atcagattcc tacctacgta acggactaag aaaaacacta cacgatgctt taactgcaaa    6240
aattcagctc accagttttg aggcaaaatt tttgagtgac atgcaaagta agcatgatct    6300
caatggttcg ttctcatggc tcacgcaaaa acaacgaacc acactagaga acatactggc    6360
taaatacgga aggatctgag gttccttatgg ctccttgtatc tatcagtgaa gcatcaagac    6420
taacaaacaa aagtagaaca actgttcacc gttagatatc aaagggaaaa ctgtccatat    6480
gcacagatga aaacggtgta aaaaagatag atacatcaga gcttttacga gttttttggtg    6540 catttaaagc tgttcaccat gaacagatcg acaatgtaac agatgaacag catgtaacac    6600
ctaatagaac aggtgaaacc agtaaaacaa agcaactaga acatgaaatt gaacacctga    6660
gacaacttgt tacagctcaa cagtcacaca tagacagcct gaaacaggcg atgctgctta    6720
tcgaatcaaa gctgccgaca acacgggagc cagtgacgcc tcccgtgggg aaaaaatcat    6780
ggcaattctg gaagaaatag cgctttcagc cggcaaacct gaagccggat ctgcgattct    6840
gataacaaac tagcaacacc agaacagccc gtttgcgggc agcaaaaccc gtactttgg    6900 acgttccggc ggttttttgt ggcgagtggt gttcggggcgg tgcgcgcaag atccattatg    6960
ttaaacgggc gagtttacat ctcaaaaccg cccgcttaac accatcagaa atcctcagcg    7020 cgatttaag caccaacccc ccccgtaac acccaaatcc atactgaaag tggctttgtt    7080
gaataaatcg aacttttgct gagttgaagg atcagatcac gcatcctccc gacaacacag    7140
accattccgt ggcaaagcaa aagttcagaa tcaccaactg gtccacctac aacaaagctc    7200
tcatcaaccg tggctccctc actttctggc tggatgatga ggcgattcag gcctggtatg    7260
agtcggcaac accttcatca cgaggaaggc cgccctttcg tcttcgaata aatacctgtg    7320
```

```
acggaagatc acttcgcaga ataaataaat cctggtgtcc ctgttgatac cgggaagccc    7380
tgggccaact tttggcgaaa atgagacgtt gatcggcacg taagaggttc aactttcac     7440 cataatgaaa taagatcact accgggcgta ttttttgagt tatcgagatt ttcaggagct    7500
aaggaagcta aaatggagaa aaaaatcact ggatatacca ccgttgatat atcccaatgg    7560
catcgtaaag aacatttttga ggcatttcag tcagttgctc aatgtaccta taaccagacc   7620
gttcagctgg atattacggc cttttttaaag accgtaaaga aaataagca caagttttat    7680 ccggccttta ttcacattct tgcccgcctg atgaatgctc atccggagtt ccgtatggca    7740
atgaaagacg gtgagctggt gatatgggat agtgttcacc cttgttacac cgttttccat    7800
gagcaaactg aaacgttttc atcgctctgg agtgaatacc acgacgattt ccggcagttt    7860
ctacacatat attcgcaaga tgtggcgtgt tacggtgaaa acctggccta tttccctaaa    7920
gggtttattg agaatatgtt tttcgtctca gccaatccct gggtgagttt caccagtttt    7980
gatttaaacg tggccaatat ggacaacttc ttcgccccccg ttttcaccat gggcaaatat    8040
tatacgcaag gcgacaaggt gctgatgccg ctggcgattc aggttcatca tgccgtctgt    8100
gatggcttcc atgtcggcag aatgcttaat gaattacaac agtactgcga tgagtggcag    8160
ggcggggcgt aattttttta aggcagttat tggtgccctt aaacgcctgg tgctacgcct    8220
gaataagtga taataagcgg atgaatggca gaaattcgaa agcaaattcg acccggtcgt    8280
cggttcaggg cagggtcgtt aaatagccgc ttatgtctat tgctggttta ccggtttatt    8340
gactaccgga agcagtgtga ccgtgtgctt ctcaaatgcc tgaggccagt ttgctcaggc    8400
tctccccgtg gaggtaataa ttgacgatat gatcatttat tctgcctccc agagcctgat    8460
aaaaacggtt agcgcttcgt taatacagat gtaggtgttc cacagggtag ccagcagcat    8520
cctgcgatgc agatccggaa cataatggtg cagggcgctt gtttcggcgt gggtatggtg    8580
gcaggccccg tggccggggg actgttgggc gctgccggca cctgtcctac gagttgcatg    8640
ataaagaaga cagtcataag tgcggcgacg atagtcatgc cccgcgccca ccggaaggag    8700
ctaccggaca gcggtgcgga ctgttgtaac tcagaataag aaatgaggcc gctcatggcg    8760
ttg                                                                 8763
```

<210> SEQ ID NO 9
<211> LENGTH: 8028
<212> TYPE: DNA
<213> ORGANISM: Artificial Sequence
<220> FEATURE:
<223> OTHER INFORMATION: chemically synthesized plasmid pGEN222AKS

<400> SEQUENCE: 9

```
gaattctgtg gtagcacaga ataatgaaaa gtgtgtaaag aagggtaaaa aaaaccgaat      60
gcgaggcatc cggttgaaat aggggtaaac agacattcag aaatgaatga cggtaataaa     120
taaagttaat gatgatagcg ggagttattc tagttgcgag tgaaggtttt gttttgacat     180
tcagtgctgt caaatactta agaataagtt attgatttta accttgaatt attattgctt     240
gatgttaggt gcttatttcg ccattccgca ataatcttaa aaagttccct tgcatttaca     300
ttttgaaaca tctatagcga taaatgaaac atcttaaaag ttttagtatc atattcgtgt     360
tggattattc tgcattttttg gggagaatgg acttgccgac tgattaatga gggttaatca    420
gtatgcagtg gcataaaaaa gcaaataaag gcatataaca gatcgatctt aaacatccac     480
aggaggatat ctgatgagta aaggagaaga acttttcact ggagttgtcc caattcttgt     540
tgaattagat ggtgatgtta atgggcacaa attttctgtc agtggagagg gtgaaggtga     600
```

```
tgcaacatac ggaaaactta cccttaaatt tatttgcact actggaaaac tacctgttcc      660
atggccaaca cttgtcacta ctttctctta tggtgttcaa tgcttttccc gttatccgga      720
tcatatgaaa cggcatgact ttttcaagag tgccatgccc gaaggttatg tacaggaacg      780
cactatatct ttcaaagatg acgggaacta caagacgcgt gctgaagtca agtttgaagg      840
tgataccctt gttaatcgta tcgagttaaa aggtattgat tttaagaag atggaaacat       900 tctcggacac aaactcgagt acaactataa ctcacacaat gtatacatca cggcagacaa      960
acaaaagaat ggaatcaaag ctaacttcaa aattcgccac aacattgaag atggatccgt     1020
tcaactagca gaccattatc aacaaaatac tccaattggc gatggccctg tccttttacc     1080
agacaaccat tacctgtcga cacaatctgc cctttcgaaa gatcccaacg aaaagcgtga     1140
ccacatggtc cttcttgagt ttgtaactgc tgctgggatt acacatggca tggatgagct     1200
ctacaaataa tgagctagcc cgcctaatga gcgggctttt ttttctcggc ctaggagata     1260
cttaacaggg aagtgagagg gccgcggcaa agccgttttt ccataggctc cgcccccctg     1320
acaagcatca cgaaatctga cgctcaaatc agtggtggcg aaacccgaca ggactataaa     1380
gataccaggc gtttccccct ggcggctccc tcgtgcgctc tcctgttcct gcctttcggt     1440
ttaccggtgt cattccgctg ttatggccgc gtttgtctca ttccacgcct gacactcagt     1500
tccgggtagg cagttcgctc caagctggac tgtatgcacg aaccccccgt tcagtccgac     1560
cgctgcgcct tatccggtaa ctatcgtctt gagtccaacc cggaaagaca tgcaaaagca     1620
ccactggcag cagccactgg taattgattt agaggagtta gtcttgaagt catgcgccgg     1680
ttaaggctaa actgaaagga caagttttgg tgactgcgct cctccaagcc agttacctcg     1740
gttcaaagag ttggtagctc agagaacctt cgaaaaaccg ccctgcaagg cggttttttc     1800
gttttcagag caagagatta cgcgcagacc aaaacgatct caagaagatc atcttattaa     1860
tcagataaaa tatttctagg atctaaaaca ctaggcccaa gagtttgtag aaacgcaaaa     1920
aggccatccg tcaggatggc cttctgctta atttgatgcc tggcagttta tggcgggcgt     1980
cctgcccgcc accctccggg ccgttgcttc gcaacgttca aatccgctcc cggcggattt     2040
gtcctactca ggagagcgtt caccgacaaa caacagataa aacgaaaggc ccagtctttc     2100
gactgagcct ttcgttttat ttgatgcctg gcagttccct actctcgcat ggggagaccc     2160
cacactacca tcggcgctac ggcgtttcac ttctgagttc ggcatggggt caggtgggac     2220
caccgcgcta ctgccgccag gcaaattctg ttttatcaga ccgcttctgc gttctgattt     2280
aatctgtatc aggctgaaaa tcttctctca tccgccaaaa cagccaagct ggatctggca     2340
aatcgctgaa tattcctttt gtctccgacc atcaggcacc tgagtcgctg tctttttcgt     2400
gacattcagt tcgctgcgct cacggctctg gcagtgaatg ggggtaaatg gcactacagg     2460
cgccttttat ggattcatgc aaggaaacta cccataatac aagaaaagcc cgtcacgggc     2520
ttctcagggc gttttatggc gggtctgcta tgtggtgcta tctgactttt tgctgttcag     2580
cagttcctgc cctctgattt ccagtctga ccacttcgga ttatcccgtg acaggtcatt     2640
cagactggct aatgcaccca gtaaggcagc ggtatcatca acaggcttac ccgtcttact     2700
gtcaaccgga tctaaaacac tagctattgt tttaatgaca aatcagaacg gaatgtcatc     2760
atcaaagtcc atcggcggct cgttagacgg cgctgccgga gcggactgct gcgggcgaga     2820
ctgcgcgccg ccgctgaact gattgccacc ctgcggctgc tgaggctgac cccaaccgcc     2880
ctgcggctga ccaccaccga tattgccacc tgccggagcg ccaccaccct gacgaccacc     2940
cagcatctgc atggtgccgc caacgttcac cacgacttct gtggtgtagc gatcctgacc     3000
```

```
ggattgatcg gtccatttac gggtacgcag ctgaccttcg atataaacct gagaaccttt    3060
acgcagatat tcgctcgcca cttctgccag tttgccgaac agcacaacgc ggtgccattc    3120
agtctgttct ttcatctcgc cggtcgcttt atcacgccag gattcggaag tagccagcgt    3180
aatgttggca actgcgccac catttggcat gtagcgtact tccgggtcct gacccagatt    3240
accaacgaga ataaccttgt ttacgcctct gctggccatg ttcgtgtctc ctgaaaaaaa    3300
tcgttctgaa taagtgtaaa cgcgcgattg taccattacc aatagcgctt ttactatgtt    3360
gtgacctcgg ttccgggaaa caaacctggc cagacattgt tacacaacac tccggataat    3420
gcattccaat actgtatatt cattcaggtc aatcatatga agggcgaatt ctgcagatat    3480
ccatcacact ggcggccgct cgagcatgca tctagttcta gaagcccaac ctttcataga    3540
aggcggcggt ggaatcgaaa tctcgtgatg gcaggttggg cgtcgcttgg tcggtcattt    3600
cgaaccccag agtcccgctc agaagaactc gtcaagaagg cgatagaagg cgatgcgctg    3660
cgaatcggga gcggcgatac cgtaaagcac gaggaagcgg tcagcccatt cgccgccaag    3720
ctcttcagca atatcacggg tagccaacgc tatgtcctga tagcggtccg ccacacccag    3780
ccggccacag tcgatgaatc cagaaaagcg gccattttcc accatgatat tcggcaagca    3840
ggcatcgcca tgggtcacga cgagatcctc gccgtcgggc atgcgcgcct tgagcctggc    3900
gaacagttcg gctggcgcga ccccctgatg ctcttcgtcc agatcatcct gatcgacaag    3960
accggcttcc atccgagtac gtgctcgctc gatgcgatgt ttcgcttggt ggtcgaatgg    4020
gcaggtagcc ggatcaagcg tatgcagccg ccgcattgca tcagccatga tggatacttt    4080
ctcggcagga gcaaggtgag atgacaggag atcctgcccc ggcacttcgc ccaatagcag    4140
ccagtccctt cccgcttcag tgacaacgtc gagcacagct gcgcaaggaa cgcccgtcgt    4200
ggccagccac gatagccgcg ctgcctcgtc ctgcagttca ttcagggcac cggacaggtc    4260
ggtcttgaca aaaagaaccg ggcgcccctg cgctgacagc cggaacacgg cggcatcaga    4320
gcagccgatt gtctgttgtg cccagtcata gccgaatagc ctctccaccc aagcggccgg    4380
agaacctgcg tgcaatccat cttgttcaat catgcgaaac gatcctcatc ctgtctcttg    4440
atcagatctt gatcccctgc gccatcagat ccttggcggc aagaaagcca tccagtttac    4500
tttgcagggc ttcccaacct taccagaggg cgccccagcc gtggcaattc cggttcgctt    4560
ctagactcga ggctagttaa gggattttgg tcatgagatt atcaaaaagg atcttcacct    4620
agatcctttt aaattaaaaa tgaagtttta aatcaatcta agtatatat gagtaaactt    4680 ggtctgacag ttaccaatgc ttaatcagtg aggcacctat ctcagcgatc tgtctatttc    4740
gttcatccat agttgcctga ctccccgtcg tgtagataac tacgatacgg gagggcttac    4800
catctggccc cagtgctgca atgataccgc gagacccacg ctcaccggct ccagatttat    4860
cagcaataaa ccagccagcc ggaagggccg agcgcagaag tggtcctgca actttatccg    4920
cctccatcca gtctattaat tgttgccggg aagctagagt aagtagttcg ccagttaata    4980
gtttgcgcaa cgttgttgcc attgctacag gcatcgtggt gtcacgctcg tcgtttggta    5040
tggcttcatt cagctccggt tcccaacgat caaggcgagt tacatgatcc cccatgttgt    5100
gcaaaaaagc ggttagctcc ttcggtcctc cgatcgttgt cagaagtaag ttggccgcag    5160
tgttatcact catggttatg gcagcactgc ataattctct tactgtcatg ccatccgtaa    5220
gatgcttttc tgtgactggt gagtactcaa ccaagtcatt ctgagaatag tgtatgcggc    5280
gaccgagttg ctcttgcccg gcgtcaacac gggataatac cgcgccacat agcagaactt    5340
taaaagtgct catcattgga aaacgttctt cggggcgaaa actctcaagg atcttaccgc    5400
```

```
tgttgagatc cagttcgatg taacccactc gtgcacccaa ctgatcttca gcatctttta    5460
cttttcaccag cgtttctggg tgagcaaaaa caggaaggca aaatgccgca aaaaagggaa   5520
taagggcgac acggaaatgt tgaatactca tactcttcct ttttcaatat tattgaagca    5580
tttatcaggg ttattgtctc atgagcggat acatatttga atgtatttag aaaaataaac    5640
aaatagggt tccgcgcaca tttccccgaa aagtgccacc tgacgtctaa gaaaccatta     5700
ttatcatgac attaacctat aaaaataggc gtatcacgag gccctttcgt cttctagaca    5760
acatcagcaa ggagaaaggg gctaccggcg aaccagcagc ccctttataa aggcgcttca    5820
gtagtcagac cagcatcagt cctgaaaagg cgggcctgcg cccgcctcca ggttgctact    5880
taccggattc gtaagccatg aaagccgcca cctccctgtg tccgtctctg taacgaatct    5940
cgcacagcga ttttcgtgtc agataagtga atatcaacag tgtgagacac acgatcaaca    6000
cacaccagac aagggaactt cgtggtagtt tcatggcctt cttctccttg cgcaaagcgc    6060
ggtaagaggc tatcctgatg tggactagac atagggatgc ctcgtggtgg ttaatgaaaa    6120
ttaacttact acggggctat cttctttctg ccacacaaca cggcaacaaa ccaccttcac    6180
gtcatgaggc agaaagcctc aagcgccggg cacatcatag cccatatacc tgcacgctga    6240
ccacactcac tttccctgaa aataatccgc tcattcagac cgttcacggg aaatccgtgt    6300
gattgttgcc gcatcacgct gcctcccgga gtttgtctcg agcacttttg ttacccgcca    6360
aacaaaaccc aaaaacaacc catacccaac ccaataaaac accaaaacaa gacaaataat    6420
cattgattga tggttgaaat ggggtaaact tgacaaacaa acccacttaa acccaaaac    6480
atacccaaac acacaccaaa aaaacaccat aaggagtttt ataaatgttg gtattcattg    6540
atgacggttc aacaaacatc aaactacagt ggcaggaaag cgacggaaca attaaacagc    6600
acattagccc gaacagcttc aaacgcgagt gggcagtctc ttttggtgat aaaaaggtct    6660
ttaactacac actgaacggc gaacagtatt catttgatcc aatcagcccg gatgctgtag    6720
tcacaaccaa tatcgcatgg caatacagcg acgttaatgt cgttgcagtg catcacgcct    6780
tactgaccag tggtctgccg gtaagcgaag tggatattgt ttgcacactt cctctgacag    6840
agtattacga cagaaataac caacccaata cggaaaatat tgagcgtaag aaagcaaact    6900
tccggaaaaa aattcatta aatggcgggg atacattcac aataaaagat gtaaagtca     6960
tgcctgaatc tataccggca ggttatgaag ttctacaaga actggatgag ttagattctt    7020
tattaattat agatctcggg ggcaccacat agatatttc tcaggtaatg gggaaattat     7080
cggggatcag taaaatatac ggagactcat ctccttggtgt ctctctggtt acatctgcag   7140
taaaagatgc cctttctctt gcgagaacaa aaggaagtag ctatcttgct gacgatataa    7200
tcattcacag aaaagataat aactatctga agcaacgaat taatgatgag aacaaaatat    7260
caatagtcac cgaagcaatg aatgaagcac ttcgtaaact tgagcaacgt gtattaaata    7320
cgctcaatga attttctggt tatactcatg ttatggttat aggcggtggc gcagaattaa    7380
tatgcgatgc agtaaaaaaa cacacacaga ttcgtgatga acgttttttc aaaaccaata    7440
actctcaata tgatttagtt aacggtatgt atctcatagg taattaatga tggacaagcg    7500
cagaaccatt gccttcaaac taaatccaga tgtaaatcaa acagataaaa ttgtttgtga    7560
tacactggac agtatcccgc aaggggaacg aagccgcctt aaccgggccg cactgacggc    7620
aggtctggcc ttatacagac aagatccccg gaccccttc cttttatgtg agctgctgac    7680
gaaagaaacc acattttcag atatcgtgaa tatattgaga tcgctatttc caaaagagat    7740
ggccgatttt aattcttcaa tagtcactca atcctcttca caacaagagc aaaaaagtga    7800
```

```
tgaagagacc aaaaaaaatg cgatgaagct aataaattaa ttcaattatt attgagttcc    7860
ctttatccac tatcaggctg gataaaggga actcaatcaa gttattttct taccagtcat    7920
tacataatcg ttattatgaa ataatcgttt gcactgtctc tgttattcag gcaatttcaa    7980
taaaggcact tgctcacgct ctgtcatttt ctgaaactct tcatgctg                 8028

<210> SEQ ID NO 10
<211> LENGTH: 4550
<212> TYPE: DNA
<213> ORGANISM: Artificial Sequence
<220> FEATURE:
<223> OTHER INFORMATION: chemically synthesized plasmid pBRmSSB

<400> SEQUENCE: 10
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc gtccattccg acagcatcgc cagtcactat ggcgtgctgc tagcgctata     240
tgcgttgatg caatttctat gcgcacccgt tctcggagca ctgtccgacc gctttggccg     300
ccgcccagtc ctgctcgctt cgctacttgg agccactatc gactacgcga tcatggcgac     360 cacaccgtc ctgtggatcc tctacgccgg acgcatcgtg gccggcatca ccggcgccac      420
aggtgcggtt gctggcgcct atatcgccga catcaccgat ggggaagatc gggctcgcca     480
cttcgggctc atgagcgctt gtttcggcgt gggtatggtg caggccccg tggccggggg      540 actgttgggc gccatctcct tgcatgcacc attccttgcg gcggcggtgc tcaacggcct     600
caacctacta ctgggctgct tcctaatgca ggagtcgcat aagggagagc gtcgaccgat     660
gcccttgaga gccttcaacc cagtcagctc cttccggtgg gcgcggggca tgactatcgt     720
cgccgcactt atgactgtct tctttatcat gcaactcgta ggacaggtgc cggcagcgct     780
ctgggtcatt ttcggcgagg accgctttcg ctggagcgcg acgatgatcg gcctgtcgct     840
tgcggtattc ggaatcttgc acgccctcgc tcaagccttc gtcactggtc ccgccaccaa     900
acgtttcggc gagaagcagg ccattatcgc cggcatggcg gccgacgcgc tgggctacgt     960
cttgctggcg ttcgcgacgc gaggctggat ggccttcccc attatgattc ttctcgcttc    1020
cggcggcatc gggatgcccg cgttgcaggc catgctgtcc aggcaggtag atgacgacca    1080
tcagggacag cttcaaggat cgctcgcggc tcttaccagc ctaacttcga tcactggacc    1140
gctgatcgtc acggcgattt atgccgcctc ggcgagcaca tggaacgggt tggcatggat    1200
tgtaggcgcc gccctatacc ttgtctgcct ccccgcgttg cgtcgcggtg catggagccg    1260
ggccacctcg acctgaatgg aagccggcgg cacctcgcta acggattcac cactccaaga    1320
attggagcca atcaattctt gcggagaact gtgaatgcgc aaaccaaccc ttggcagaac    1380
atatccatcg cgtccgccat ctccagcagc cgcacgcggc gcatctcggg cagcgttggg    1440
tcctggccac gggtgcgcat gatcgtgctc ctgtcgttga ggacccggct aggctggcgg    1500
ggttgcctta ctggttagca gaatgaatca ccgatacgcg agcgaacgtg aagcgactgc    1560
tgctgcaaaa cgtctgcgac ctgagcaaca acatgaatgg tcttcggttt ccgtgtttcg    1620
taaagtctgg aaacgcggaa gtcagcgccc tgcaccatta tgttccggat ctgcatcgca    1680
ggatgctgct ggctaccctg tggaacacct acatctgtat taacgaagcg ctggcattga    1740
ccctgagtga ttttttctctg gtcccgccgc atccataccg ccagttgttt accctcacaa    1800
cgttccagta accgggcatg ttcatcatca gtaacccgta tcgtgagcat cctctctcgt    1860
```

```
ttcatcggta tcattacccc catgaacaga atccccctt acacggaggc atcagtgacc    1920
aaacaggaaa aaaccgccct aacatggcc cgctttatca gaagccagac attaacgctt    1980
ctggagaaac tcaacgagct ggacgcggat gaacaggcag acatctgtga atcgcttcac    2040
gaccacgctg atgagcttta ccgcagctgc ctcgcgcgtt tcggtgatga cggtgaaaac    2100
ctctgacaca tgcagctccc ggagacggtc acagcttgtc tgtaagcgga tgccgggagc    2160
agacaagccc gtcagggcgc gtcagcgggt gttggcgggt gtcggggcgc agccatgacc    2220
cagtcacgta gcgatagcgg agtgtatact ggcttaacta tgcggcatca gagcagattg    2280
tactgagagt gcaccatatg cggtgtgaaa taccgcacag atgcgtaagg agaaaatacc    2340
gcatcaggcg ctcttccgct tcctcgctca ctgactcgct gcgctcggtc gttcggctgc    2400
ggcgagcggt atcagctcac tcaaaggcgg taatacggtt atccacagaa tcaggggata    2460
acgcaggaaa gaacatgtga gcaaaaggcc agcaaaaggc caggaaccgt aaaaaggccg    2520
cgttgctggc gttttccat aggctccgcc cccctgacga gcatcacaaa aatcgacgct    2580
caagtcagag gtggcgaaac ccgacaggac tataaagata ccaggcgttt ccccctggaa    2640
gctccctcgt gcgctctcct gttccgaccc tgccgcttac cggatacctg tccgcctttc    2700
tcccttcggg aagcgtggcg ctttctcata gctcacgctg taggtatctc agttcggtgt    2760
aggtcgttcg ctccaagctg ggctgtgtgc acgaaccccc cgttcagccc gaccgctgcg    2820
ccttatccgg taactatcgt cttgagtcca acccggtaag acacgactta tcgccactgg    2880
cagcagccac tggtaacagg attagcagag cgaggtatgt aggcggtgct acagagttct    2940
tgaagtggtg gcctaactac ggctacacta aaggacagt atttggtatc tgcgctctgc    3000
tgaagccagt taccttcgga aaagagttg gtagctcttg atccggcaaa caaaccaccg    3060
ctggtagcgg tggtttttt gtttgcaagc agcagattac gcgcagaaaa aaaggatctc    3120
aagaagatcc tttgatcttt tctacggggt ctgacgctca gtggaacgaa aactcacgtt    3180
aagggatttt ggtcatgaga ttatcaaaaa ggatcttcac ctagatcctt ttaaattaaa    3240
aatgaagttt taaatcaatc taaagtatat atgagtaaac ttggtctgac agttaccaat    3300
gcttaatcag tgaggcacct atctcagcga tctgtctatt tcgttcatcc atagttgcct    3360
gactccccgt cgtgtagata actacgatac gggagggctt accatctggc cccagtgctg    3420
caatgatacc gcgagaccca cgctcaccgg ctccagattt atcagcaata aaccagccag    3480
ccggaagggc cgagcgcaga agtggtcctg caactttatc cgcctccatc cagtctatta    3540
attgttgccg ggaagctaga gtaagtagtt cgccagttaa tagtttgcgc aacgttgttg    3600
ccattgcatt attgaagcat ttatcagggt tattgtctca tgagcggata catatttgaa    3660
tgtatttaga aaataaaca aatagggtt ccgcgcacat ttccccgaaa agtgccacct    3720
gacgtctaag aaaccattat tatcatgaca ttaacctata aaaataggcg tatcacgagg    3780
ccctttcgtc ttcaagaatt cgcccttgct agctattgtt ttaatgacaa atcagaacgg    3840
aatgtcatca tcaaagtcca tcggcggctc gttagacggc gctgccggag cggactgctg    3900
cgggcgagac tgcgcgccgc cgctgaactg attgccaccc tgcggctgct gaggctgacc    3960
ccaaccgccc tgcggctgac caccaccgat attgccacct gccggagcgc caccaccctg    4020
acgaccaccc agcatctgca tggtgccgcc aacgttcacc acgacttctg tggtgtagcg    4080
atcctgaccg gattgatcgg tccatttacg ggtacgcagc tgaccttcga tataaacctg    4140 agaacctta cgcagatatt cgctcgccac ttctgccagt ttgccgaaca gcacaacgcg    4200
gtgccattca gtctgttctt tcatctcgcc ggtcgcttta tcacgccagg attcggaagt    4260
```

-continued

```
agccagcgta atgttggcaa ctgcgccacc atttggcatg tagcgtactt ccgggtcctg    4320
acccagatta ccaacgagaa taaccttgtt tacgcctctg ctggccatgt tcgtgtctcc    4380
tgtcgttctg aataagtgta aacgcgcgat tgtaccatta ccaatagcgc ttttactatg    4440
ttgtgacctc ggttccggga aacaaacctg gccagacatt gttacacaac actccggata    4500
atgcattcca atactgtata ttcattcagg tcaatcatat gaagggcgaa               4550

<210> SEQ ID NO 11
<211> LENGTH: 30
<212> TYPE: DNA
<213> ORGANISM: Artificial Sequence
<220> FEATURE:
<223> OTHER INFORMATION: chemically synthesized amplification primer

<400> SEQUENCE: 11
catatgaata tcctccttag ttcctattcc                                       30

<210> SEQ ID NO 12
<211> LENGTH: 36
<212> TYPE: DNA
<213> ORGANISM: Artificial Sequence
<220> FEATURE:
<223> OTHER INFORMATION: chemically synthesized amplification primer

<400> SEQUENCE: 12
gctagcgtgt aggctggagc tgcttcgaag ttccta                                36

<210> SEQ ID NO 13
<211> LENGTH: 35
<212> TYPE: DNA
<213> ORGANISM: Artificial Sequence
<220> FEATURE:
<223> OTHER INFORMATION: chemically synthesized amplification primer

<400> SEQUENCE: 13
catatgttat attgttttaa ggtggatgat taaag                                 35

<210> SEQ ID NO 14
<211> LENGTH: 30
<212> TYPE: DNA
<213> ORGANISM: Artificial Sequence
<220> FEATURE:
<223> OTHER INFORMATION: chemically synthesized amplification primer

<400> SEQUENCE: 14
ggaaagatcg cagacttcgc catcaatacg                                       30

<210> SEQ ID NO 15
<211> LENGTH: 54
<212> TYPE: DNA
<213> ORGANISM: Artificial Sequence
<220> FEATURE:
<223> OTHER INFORMATION: chemically synthesized amplification primer

<400> SEQUENCE: 15
catatgttat tattattagc tagctactgt atattcattc aggtcaattt gtgt            54

<210> SEQ ID NO 16
<211> LENGTH: 30
<212> TYPE: DNA
<213> ORGANISM: Artificial Sequence
<220> FEATURE:
<223> OTHER INFORMATION: chemically synthesized amplification primer

<400> SEQUENCE: 16
```

```
gaagcgatca accaccactt caatggtatg                                        30
```

<210> SEQ ID NO 17
<211> LENGTH: 42
<212> TYPE: DNA
<213> ORGANISM: Artificial Sequence
<220> FEATURE:
<223> OTHER INFORMATION: chemically synthesized amplification primer

<400> SEQUENCE: 17

```
ctcgagacta gttctgtaca gcaataaaag tcacggccta at                          42
```

<210> SEQ ID NO 18
<211> LENGTH: 30
<212> TYPE: DNA
<213> ORGANISM: Artificial Sequence
<220> FEATURE:
<223> OTHER INFORMATION: chemically synthesized amplification primer

<400> SEQUENCE: 18

```
ctacaggaat gcagaggcgg cgggaagata                                        30
```

<210> SEQ ID NO 19
<211> LENGTH: 30
<212> TYPE: DNA
<213> ORGANISM: Artificial Sequence
<220> FEATURE:
<223> OTHER INFORMATION: chemically synthesized amplification primer

<400> SEQUENCE: 19

```
ttcggcggat cggagagatc gcagacttcg                                        30
```

<210> SEQ ID NO 20
<211> LENGTH: 30
<212> TYPE: DNA
<213> ORGANISM: Artificial Sequence
<220> FEATURE:
<223> OTHER INFORMATION: chemically synthesized amplification primer

<400> SEQUENCE: 20

```
agacatcaat tattgcacta actatatctt                                        30
```

<210> SEQ ID NO 21
<211> LENGTH: 30
<212> TYPE: DNA
<213> ORGANISM: Artificial Sequence
<220> FEATURE:
<223> OTHER INFORMATION: chemically synthesized amplification primer

<400> SEQUENCE: 21

```
cttgccagat tttccagcgt tttggtgtgt                                        30
```

<210> SEQ ID NO 22
<211> LENGTH: 54
<212> TYPE: DNA
<213> ORGANISM: Artificial Sequence
<220> FEATURE:
<223> OTHER INFORMATION: chemically synthesized amplification primer

<400> SEQUENCE: 22

```
catatgttat tattattagc tagctactgt atattcaaac aggttaaatt gtgt             54
```

<210> SEQ ID NO 23
<211> LENGTH: 36
<212> TYPE: DNA
<213> ORGANISM: Artificial Sequence
<220> FEATURE:

<223> OTHER INFORMATION: chemically synthesized amplification primer

<400> SEQUENCE: 23
catatgcatt tcgctatag ttctcgtctg ctgaaa                                36

<210> SEQ ID NO 24
<211> LENGTH: 42
<212> TYPE: DNA
<213> ORGANISM: Artificial Sequence
<220> FEATURE:
<223> OTHER INFORMATION: chemically synthesized amplification primer

<400> SEQUENCE: 24
ctcgagacta gttagctaat cattgaaact ctaaatcatt tt                        42

<210> SEQ ID NO 25
<211> LENGTH: 7568
<212> TYPE: DNA
<213> ORGANISM: Artificial Sequence
<220> FEATURE:
<223> OTHER INFORMATION: Chemically-synthesized plasmid pPA83

<400> SEQUENCE: 25
gaattctgtg gtagcacaga ataatgaaaa gtgtgtaaag aagggtaaaa aaaaccgaat      60
gcgaggcatc cggttgaaat aggggtaaac agacattcag aaatgaatga cggtaataaa    120
taaagttaat gatgatagcg ggagttattc tagttgcgag tgaaggtttt gttttgacat    180
tcagtgctgt caaatactta agaataagtt attgatttta accttgaatt attattgctt    240
gatgttaggt gcttatttcg ccattccgca ataatcttaa aaagttccct tgcatttaca    300
ttttgaaaca tctatagcga taatgaaac atcttaaaag ttttagtatc atattcgtgt     360
tggattattc tgcatttttg gggagaatgg acttgccgac tgattaatga gggttaatca    420
gtatgcagtg gcataaaaaa gcaaataaag gcatataaca gatcgatctt aaacatccac    480
aggaggatgg gatccaaaat aaggaggaaa aaaaatgac tagcgaagtt aaacaggaga    540
accgtctgct gaatgaaagc gaaagcagca gccagggcct gctgggctat tattttagcg    600
atctgaattt tcaggcaccg atggtggtta ccagcagcac caccggcgat ctgagcattc    660
cgagcagcga gctggaaaat attccgagcg aaaaccagta ttttcagagc gccatttgga    720
gcggctttat caaagttaag aaaagcgatg aatataccct tgccaccagc gccgataatc    780
atgttaccat gtgggttgat gaccaggaag ttatcaacaa agcgagcaat agcaacaaaa    840
tccgtctcga gaaggccgt ctgtatcaga ttaaaattca gtatcagcgt gaaaatccga    900
ccgaaaaagg cctggatttt aagctgtatt ggaccgatag ccagaataaa aagaagtga    960 ttagcagcga taacctgcaa ttgccggaac tgaaacagaa aagcagcaac agccgtaaaa   1020
aacgtagtac tagtgccggc ccgaccgttc cggaccgtga caatgatggc atcccggata   1080
gcctggaggt tgaaggctat accgttgatg ttaaaaataa acgtacccttt ctgagcccat   1140 ggattagcaa tattcatgaa aaaaaaggcc tgaccaaata taaagcagc ccggaaaaat    1200 ggagcaccgc cagcgatccg tatagcgatt ttgaaaagt taccgccgt attgataaaa    1260 atgttagccc ggaggcacgt catccgctgg tggcagccta tccgattgtt catgttgata   1320
tggagaatat tatcctgagc aaaaatgagg atcagagcac ccagaatacc gatagcgaaa   1380
cccgtaccat tagcaaaaat accagcacca gccgtaccca taccagcgaa gttcatggca   1440
atgcagaagt gcatgcgagc ttctttgata ttggtggcag cgtttctgca ggatttagca   1500
attcgaattc aagcaccgtg gcgattgatc atagcctgag cctggcaggc gaacgtacct   1560

```
gggccgaaac gatgggtctg aataccgccg ataccgcacg tctgaatgcc aatattcgtt    1620
atgttaatac cggcaccgcc ccgatctata acgtgctgcc gaccaccagc ctggtgctgg    1680
gcaaaaatca gaccctcgcg acaattaaag ccaagaaaaa ccagctgagc cagattctgg    1740
caccgaataa ctattatccg agcaaaaact tggcgccaat cgcactgaat gcacaggacg    1800
attttagcag caccccgatt accatgaatt ataatcagtt tctggagctg aaaaaaacca    1860
aacagctgcg tctggatacc gatcaggttt atggcaatat tgcaacctat aattttgaaa    1920
atggccgtgt gcgtgtggat accggcagca actggagcga agtgctgccg cagattcagg    1980
aaaccaccgc acgtatcatt tttaatggca aagatttaaa tctggttgaa cgtcgtattg    2040
cggccgttaa tccgagcgat ccgctggaaa ccaccaaacc ggatatgacc ctgaaagaag    2100
ccctgaaaat tgcatttggc tttaacgaac cgaatggcaa ccttcagtat cagggcaaag    2160
acattaccga atttgatttt aattttgacc agcagaccag ccagaatatc aaaaatcagc    2220
tggcggagct caacgcgacc aacatttata ccgttctgga taaaatcaaa ctgaatgcaa    2280
aaatgaatat tctgattcgt gataaacgtt ttcattatga tcgtaataac attgcagttg    2340
gcgcggatga gagcgttgtg aaagaggccc atcgtgaagt tattaatagc agcaccgagg    2400
gcctgctgct gaatattgat aaagatattc gtaaaattct gagcggttat attgttgaaa    2460
ttgaagatac cgaaggcctg aaagaagtta ttaacgaccg ttatgatatg ctgaatatta    2520
gcagcctgcg tcaggatggc aaaacccttta ttgatttttaa gaaatataat gataagcttc    2580
cgctgtatat tagcaatccg aattataaag ttaatgttta tgccgttacc aaagaaaaca    2640
ccattatcaa tccgagcgag aatggcgata ccagcaccaa cggcatcaag aaaattctga    2700
tctttagcaa aaaaggctat gagattggct aatgacctag cgtcgacact agcccgccta    2760
atgagcgggc ttttttttct cggcctagga gatacttaac agggaagtga gagggccgcg    2820
gcaaagccgt ttttccatag gctccgcccc cctgacaagc atcacgaaat ctgacgctca    2880
aatcagtggt ggcgaaaccc gacaggacta taaagatacc aggcgtttcc ccctggcggc    2940
tccctcgtgc gctctcctgt tcctgccttt cggtttaccg gtgtcattcc gctgttatgg    3000
ccgcgtttgt ctcattccac gcctgacact cagttccggg taggcagttc gctccaagct    3060
ggactgtatg cacgaacccc ccgttcagtc cgaccgctgc gccttatccg gtaactatcg    3120
tcttgagtcc aacccggaaa gacatgcaaa agcaccactg gcagcagcca ctggtaattg    3180
atttagagga gttagtcttg aagtcatgcg ccggttaagg ctaaactgaa aggacaagtt    3240
ttggtgactg cgctcctcca agccagttac ctcggttcaa agagttggta gctcagagaa    3300
ccttcgaaaa accgccctgc aaggcggttt tttcgttttc agagcaagag attacgcgca    3360
gaccaaaacg atctcaagaa gatcatctta ttaatcagat aaaatatttc taggatctaa    3420
aacactaggc ccaagagttt gtagaaacgc aaaaaggcca tccgtcagga tggccttctg    3480
cttaatttga tgcctggcag tttatggcgg gcgtcctgcc cgccaccctc cgggccgttg    3540
cttcgcaacg ttcaaatccg ctcccggcgg atttgtccta ctcaggagag cgttcaccga    3600
caaacaacag ataaaacgaa aggcccagtc tttcgactga gcctttcgtt ttatttgatg    3660
cctggcagtt ccctactctc gcatggggag accccacact accatcggcg ctacggcgtt    3720
tcacttctga gttcggcatg gggtcaggtg ggaccaccgc gctactgccg ccaggcaaat    3780
tctgttttat cagaccgctt ctgcgttctg atttaatctg tatcaggctg aaaatcttct    3840
ctcatccgcc aaaacagcca agctggatct ggcaaatcgc tgaatattcc ttttgtctcc    3900
gaccatcagg cacctgagtc gctgtctttt tcgtgacatt cagttcgctg cgctcacggc    3960
```

```
tctggcagtg aatgggggta aatggcacta caggcgcctt ttatggattc atgcaaggaa    4020
actacccata atacaagaaa agcccgtcac gggcttctca gggcgtttta tggcgggtct    4080
gctatgtggt gctatctgac tttttgctgt tcagcagttc ctgccctctg attttccagt    4140
ctgaccactt cggattatcc cgtgacaggt cattcagact ggctaatgca cccagtaagg    4200
cagcggtatc atcaacaggc ttacccgtct tactgtcaac cggatctaaa acactagccc    4260
aacctttcat agaaggcggc ggtggaatcg aaatctcgtg atggcaggtt gggcgtcgct    4320
tggtcggtca tttcgaaccc cagagtcccg ctcagaagaa ctcgtcaaga aggcgataga    4380
aggcgatgcg ctgcgaatcg ggagcggcga taccgtaaag cacgaggaag cggtcagccc    4440
attcgccgcc aagctcttca gcaatatcac gggtagccaa cgctatgtcc tgatagcggt    4500
ccgccacacc cagccggcca cagtcgatga atccagaaaa gcggccattt tccaccatga    4560
tattcggcaa gcaggcatcg ccatgggtca cgacgagatc ctcgccgtcg gcatgcgcg    4620 ccttgagcct ggcgaacagt tcggctggcg cgagccctg atgctcttcg tccagatcat    4680
cctgatcgac aagaccggct tccatccgag tacgtgctcg ctcgatgcga tgtttcgctt    4740
ggtggtcgaa tgggcaggta gccggatcaa gcgtatgcag ccgccgcatt gcatcagcca    4800
tgatggatac tttctcggca ggagcaaggt gagatgacag gagatcctgc cccggcactt    4860
cgcccaatag cagccagtcc cttcccgctt cagtgacaac gtcgagcaca gctgcgcaag    4920
gaacgcccgt cgtggccagc cacgatagcc gcgctgcctc gtcctgcagt tcattcaggg    4980
caccggacag gtcggtcttg acaaaaagaa ccgggcgccc ctgcgctgac agccggaaca    5040
cggcggcatc agagcagccg attgtctgtt gtgcccagtc atagccgaat agcctctcca    5100
cccaagcggc cggagaacct gcgtgcaatc catcttgttc aatcatgcga acgatcctc    5160 atcctgtctc ttgatcagat cttgatcccc tgcgccatca gatccttggc ggcaagaaag    5220
ccatccagtt tactttgcag ggcttcccaa ccttaccaga gggcgcccca gccgtggcaa    5280
ttccggttcg ctgctagaca acatcagcaa ggagaaaggg gctaccggcg aaccagcagc    5340
ccctttataa aggcgcttca gtagtcgac cagcatcagt cctgaaaagg cgggcctgcg    5400
cccgcctcca ggttgctact taccggattc gtaagccatg aaagccgcca cctccctgtg    5460
tccgtctctg taacgaatct cgcacagcga ttttcgtgtc agataagtga atatcaacag    5520
tgtgagacac acgatcaaca cacaccgac aagggaactt cgtggtagtt tcatggcctt    5580
cttctccttg cgcaaagcgc ggtaagaggc tatcctgatg tggactagac atagggatgc    5640
ctcgtggtgg ttaatgaaaa ttaacttact acggggctat cttctttctg ccacacaaca    5700
cggcaacaaa ccaccttcac gtcatgaggc agaaagcctc aagcgccggg cacatcatag    5760
cccatatacc tgcacgctga ccacactcac tttccctgaa aataatccgc tcattcagac    5820
cgttcacggg aaatccgtgt gattgttgcc gcatcacgct gcctcccgga gtttgtctcg    5880
agcacttttg ttacccgcca aacaaaaccc aaaaacaacc catacccaac ccaataaaac    5940
accaaaacaa gacaaataat cattgattga tggttgaaat ggggtaaact tgacaaacaa    6000
acccacttaa aacccaaaac atacccaaac acacaccaaa aaacaccat aaggagtttt    6060 ataaatgttg gtattcattg atgacggttc aacaaacatc aaactacagt ggcaggaaag    6120
cgacggaaca attaaacagc acattagccc gaacagcttc aaacgcgagt gggcagtctc    6180
ttttggtgat aaaaaggtct ttaactacac actgaacggc gaacagtatt catttgatcc    6240
aatcagcccg gatgctgtag tcacaaccaa tatcgcatgg caatacagcg acgttaatgt    6300
cgttgcagtg catcacgcct tactgaccag tggtctgccg gtaagcgaag tggatattgt    6360
```

```
ttgcacactt cctctgacag agtattacga cagaaataac caacccaata cggaaaatat    6420
tgagcgtaag aaagcaaact tccggaaaaa aattacatta aatggcgggg atacattcac    6480
aataaaagat gtaaaagtca tgcctgaatc tataccggca ggttatgaag ttctacaaga    6540
actggatgag ttagattctt tattaattat agatctcggg ggcaccacat tagatatttc    6600
tcaggtaatg gggaaattat cggggatcag taaaatatac ggagactcat ctcttggtgt    6660
ctctctggtt acatctgcag taaaagatgc cctttctctt gcgagaacaa aaggaagtag    6720
ctatcttgct gacgatataa tcattcacag aaaagataat aactatctga agcaacgaat    6780
taatgatgag aacaaaatat caatagtcac cgaagcaatg aatgaagcac ttcgtaaact    6840
tgagcaacgt gtattaaata cgctcaatga attttctggt tatactcatg ttatggttat    6900
aggcggtggc gcagaattaa tatgcgatgc agtaaaaaaa cacacacaga ttcgtgatga    6960
acgttttttc aaaaccaata actctcaata tgatttagtt aacggtatgt atctcatagg    7020
taattaatga tggacaagcg cagaaccatt gccttcaaac taaatccaga tgtaaatcaa    7080
acagataaaa ttgtttgtga tacactggac agtatcccgc aaggggaacg aagccgcctt    7140
aaccgggccg cactgacggc aggtctggcc ttatacagac aagatccccg gaccccttc     7200 cttttatgtg agctgctgac gaaagaaacc acattttcag atatcgtgaa tatattgaga    7260
tcgctatttc caaagagat ggccgatttt aattcttcaa tagtcactca atcctcttca     7320
caacaagagc aaaaaagtga tgaagagacc aaaaaaaatg cgatgaagct aataaattaa    7380
ttcaattatt attgagttcc ctttatccac tatcaggctg ataaaggga actcaatcaa     7440 gttattttct taccagtcat tacataatcg ttattatgaa ataatcgttt gcactgtctc    7500
tgttattcag gcaatttcaa taaaggcact tgctcacgct ctgtcatttt ctgaaactct    7560
tcatgctg                                                             7568
```

<210> SEQ ID NO 26
<211> LENGTH: 738
<212> TYPE: PRT
<213> ORGANISM: Bacillus anthracis

<400> SEQUENCE: 26

```
Met Thr Ser Glu Val Lys Gln Glu Asn Arg Leu Leu Asn Glu Ser
1               5                   10                  15

Ser Ser Ser Gln Gly Leu Leu Gly Tyr Tyr Phe Ser Asp Leu Asn Phe
                20                  25                  30

Gln Ala Pro Met Val Val Thr Ser Ser Thr Gly Asp Leu Ser Ile
                35                  40                  45

Pro Ser Ser Glu Leu Glu Asn Ile Pro Ser Glu Asn Gln Tyr Phe Gln
            50                  55                  60

Ser Ala Ile Trp Ser Gly Phe Ile Lys Val Lys Lys Ser Asp Glu Tyr
65                  70                  75                  80

Thr Phe Ala Thr Ser Ala Asp Asn His Val Thr Met Trp Val Asp Asp
                85                  90                  95

Gln Glu Val Ile Asn Lys Ala Ser Asn Ser Asn Lys Ile Arg Leu Glu
            100                 105                 110

Lys Gly Arg Leu Tyr Gln Ile Lys Ile Gln Tyr Gln Arg Glu Asn Pro
        115                 120                 125

Thr Glu Lys Gly Leu Asp Phe Lys Leu Tyr Trp Thr Asp Ser Gln Asn
    130                 135                 140

Lys Lys Glu Val Ile Ser Ser Asp Asn Leu Gln Leu Pro Glu Leu Lys
145                 150                 155                 160
```

-continued

```
Gln Lys Ser Ser Asn Ser Arg Lys Lys Arg Ser Thr Ser Ala Gly Pro
                165                 170                 175

Thr Val Pro Asp Arg Asp Asn Asp Gly Ile Pro Asp Ser Leu Glu Val
            180                 185                 190

Glu Gly Tyr Thr Val Asp Val Lys Asn Lys Arg Thr Phe Leu Ser Pro
        195                 200                 205

Trp Ile Ser Asn Ile His Glu Lys Lys Gly Leu Thr Lys Tyr Lys Ser
    210                 215                 220

Ser Pro Glu Lys Trp Ser Thr Ala Ser Asp Pro Tyr Ser Asp Phe Glu
225                 230                 235                 240

Lys Val Thr Gly Arg Ile Asp Lys Asn Val Ser Pro Glu Ala Arg His
                245                 250                 255

Pro Leu Val Ala Ala Tyr Pro Ile Val His Val Asp Met Glu Asn Ile
            260                 265                 270

Ile Leu Ser Lys Asn Glu Asp Gln Ser Thr Gln Asn Thr Asp Ser Glu
        275                 280                 285

Thr Arg Thr Ile Ser Lys Asn Thr Ser Thr Ser Arg Thr His Thr Ser
    290                 295                 300

Glu Val His Gly Asn Ala Glu Val His Ala Ser Phe Phe Asp Ile Gly
305                 310                 315                 320

Gly Ser Val Ser Ala Gly Phe Ser Asn Ser Asn Ser Ser Thr Val Ala
                325                 330                 335

Ile Asp His Ser Leu Ser Leu Ala Gly Glu Arg Thr Trp Ala Glu Thr
            340                 345                 350

Met Gly Leu Asn Thr Ala Asp Thr Ala Arg Leu Asn Ala Asn Ile Arg
        355                 360                 365

Tyr Val Asn Thr Gly Thr Ala Pro Ile Tyr Asn Val Leu Pro Thr Thr
    370                 375                 380

Ser Leu Val Leu Gly Lys Asn Gln Thr Leu Ala Thr Ile Lys Ala Lys
385                 390                 395                 400

Glu Asn Gln Leu Ser Gln Ile Leu Ala Pro Asn Asn Tyr Tyr Pro Ser
                405                 410                 415

Lys Asn Leu Ala Pro Ile Ala Leu Asn Ala Gln Asp Asp Phe Ser Ser
            420                 425                 430

Thr Pro Ile Thr Met Asn Tyr Asn Gln Phe Leu Glu Leu Glu Lys Thr
        435                 440                 445

Lys Gln Leu Arg Leu Asp Thr Asp Gln Val Tyr Gly Asn Ile Ala Thr
    450                 455                 460

Tyr Asn Phe Glu Asn Gly Arg Val Arg Val Asp Thr Gly Ser Asn Trp
465                 470                 475                 480

Ser Glu Val Leu Pro Gln Ile Gln Glu Thr Thr Ala Arg Ile Ile Phe
                485                 490                 495

Asn Gly Lys Asp Leu Asn Leu Val Glu Arg Arg Ile Ala Ala Val Asn
            500                 505                 510

Pro Ser Asp Pro Leu Glu Thr Thr Lys Pro Asp Met Thr Leu Lys Glu
        515                 520                 525

Ala Leu Lys Ile Ala Phe Gly Phe Asn Glu Pro Asn Gly Asn Leu Gln
    530                 535                 540

Tyr Gln Gly Lys Asp Ile Thr Glu Phe Asp Phe Asn Phe Asp Gln Gln
545                 550                 555                 560

Thr Ser Gln Asn Ile Lys Asn Gln Leu Ala Glu Leu Asn Ala Thr Asn
                565                 570                 575

Ile Tyr Thr Val Leu Asp Lys Ile Lys Leu Asn Ala Lys Met Asn Ile
            580                 585                 590
```

Leu Ile Arg Asp Lys Arg Phe His Tyr Asp Arg Asn Asn Ile Ala Val
    595                 600                 605

Gly Ala Asp Glu Ser Val Val Lys Glu Ala His Arg Glu Val Ile Asn
610                 615                 620

Ser Ser Thr Glu Gly Leu Leu Asn Ile Asp Lys Asp Ile Arg Lys
625                 630                 635                 640

Ile Leu Ser Gly Tyr Ile Val Glu Ile Glu Asp Thr Glu Gly Leu Lys
            645                 650                 655

Glu Val Ile Asn Asp Arg Tyr Asp Met Leu Asn Ile Ser Ser Leu Arg
            660                 665                 670

Gln Asp Gly Lys Thr Phe Ile Asp Phe Lys Lys Tyr Asn Asp Lys Leu
            675                 680                 685

Pro Leu Tyr Ile Ser Asn Pro Asn Tyr Lys Val Asn Val Tyr Ala Val
            690                 695                 700

Thr Lys Glu Asn Thr Ile Ile Asn Pro Ser Glu Asn Gly Asp Thr Ser
705                 710                 715                 720

Thr Asn Gly Ile Lys Lys Ile Leu Ile Phe Ser Lys Lys Gly Tyr Glu
            725                 730                 735

Ile Gly

<210> SEQ ID NO 27
<211> LENGTH: 921
<212> TYPE: DNA
<213> ORGANISM: Salmonella typhi

<400> SEQUENCE: 27
atgactagta ttttgcaga acaaactgta gaggtagtta aaagcgcgat cgaaaccgca      60 gatgggcat tagatcttta taacaaatac ctcgaccagg tcatcccctg gaagaccttt     120
gatgaaacca taaagagtt aagccgtttt aaacaggagt actcgcagga agcttctgtt     180
ttagttggtg atattaaagt tttgcttatg acagccagg acaagtattt tgaagcgaca     240
caaactgttt atgaatggtg tggtgtcgtg acgcaattac tctcagcgta tattttacta     300
tttgatgaat ataatgagaa aaaagcatca gcccagaaag acattctcat taggatatta     360
gatgatggtg tcaagaaact gaatgaagcg caaaaatctc tcctgacaag ttcacaaagt     420
ttcaacaacg cttccggaaa actgctggca ttagatagcc agttaactaa tgatttttcg     480
gaaaaaagta gttatttcca gtcacaggtg gatagaattc gtaaggaagc ttatgccggt     540
gctgcagccg gcatagtcgc cggtccgttt ggattaatta tttcctattc tattgctgcg     600
ggcgtgattg aagggaaatt gattccagaa ttgaataaca ggctaaaaac agtgcaaaat     660
ttctttacta gcttatcagc tacagtgaaa caagcgaata agatatcga tgcggcaaaa     720 ttgaaattag ccactgaaat agcagcaatt ggggagataa aaacggaaac cgaaacaacc     780
agattctacg ttgattatga tgatttaatg ctttctttat taaaaggagc tgcaaagaaa     840
atgattaaca cctgtaatga ataccaacaa cgtcatggta agaagacgct tttcgaggtt     900
cctgacgtcg ctagctgata a                                              921

<210> SEQ ID NO 28
<211> LENGTH: 1347
<212> TYPE: DNA
<213> ORGANISM: Artificial Sequence
<220> FEATURE:
<223> OTHER INFORMATION: Chemically-synthesized clyA::d4 fusion
      construct

<400> SEQUENCE: 28

```
atgactagta tttttgcaga acaaactgta gaggtagtta aaagcgcgat cgaaaccgca      60
gatgggcat  tagatcttta taacaaatac ctcgaccagg tcatcccctg gaagaccttt     120
gatgaaacca taaagagagtt aagccgtttt aaacaggagt actcgcagga agcttctgtt    180
ttagttggtg atattaaagt tttgcttatg gacagccagg acaagtattt tgaagcgaca     240
caaactgttt atgaatggtg tggtgtcgtg acgcaattac tctcagcgta tattttacta    300
tttgatgaat ataatgagaa aaaagcatca gcccagaaag acattctcat taggatatta    360
gatgatggtg tcaagaaact gaatgaagcg caaaaatctc tcctgacaag ttcacaaagt    420
ttcaacaacg cttccggaaa actgctggca ttagatagcc agttaactaa tgattttcg     480
gaaaaaagta gttatttcca gtcacaggtg gatagaattc gtaaggaagc ttatgccggt    540
gctgcagccg gcatagtcgc cggtccgttt ggattaatta tttcctattc tattgctgcg    600
ggcgtgattg aagggaaatt gattccagaa ttgaataaca ggctaaaaac agtgcaaaat    660
ttctttacta gcttatcagc tacagtgaaa caagcgaata agatatcga tgcggcaaaa    720
ttgaaattag ccactgaaat agcagcaatt ggggagataa aaacggaaac cgaaacaacc    780
agattctacg ttgattatga tgatttaatg ctttctttat aaaaggagc tgcaaagaaa    840
atgattaaca cctgtaatga ataccaacaa cgtcatggta agaagacgct tttcgaggtt    900
cctgacgtcg ctagtaaacg ttttcattat gatcgtaata acatcgcagt tggggcggat    960
gagtcagtag ttaaggaggc tcatcgtgaa gtaattaatt cgtcaacaga gggattattg   1020
ttaaatattg ataaggatat ccgtaaaatc ttatccggat atattgtaga aattgaagat   1080
actgaagggc ttaaagaagt tatcaatgac cgttatgata tgttgaatat ttctagttta   1140
cgtcaagatg gaaaaacatt tatcgatttt aaaaaatata atgataaatt accgttatat   1200
atcagtaatc cgaattataa ggtaaatgta tatgctgtta ctaaagaaaa cactattatt   1260
aatcctagtg agaatgggga taccagcacc aacgggatca agaaaattt aatcttttct    1320
aaaaaaggct atgagatcgg ataatga                                        1347
```

<210> SEQ ID NO 29
<211> LENGTH: 301
<212> TYPE: DNA
<213> ORGANISM: Escherichia coli

<400> SEQUENCE: 29

```
gctagcgggc accccaggct ttccacttta tgcttccggc tcgtataatg tgtggaatct     60
agaaaataag gaggaaaaaa aaatgagtta taaaaaactg taccaattga cggctatatt    120
tagtttacct cttactatct tattggtttc actttcatcc cttcggattg ttggcgaagg    180
gaattcttat gttgacgttt ttctaagctt tataatattt cttggtttta ttgagctgat    240
tcatgggatt cgaaagattt tggtctggtc aggctggaaa aacggaagtt aataggctag    300
c                                                                    301
```

<210> SEQ ID NO 30
<211> LENGTH: 69
<212> TYPE: PRT
<213> ORGANISM: Escherichia coli

<400> SEQUENCE: 30

```
Met Ser Tyr Lys Lys Leu Tyr Gln Leu Thr Ala Ile Phe Ser Leu Pro
1               5                   10                  15

Leu Thr Ile Leu Leu Val Ser Leu Ser Ser Leu Arg Ile Val Gly Glu
            20                  25                  30
```

Gly Asn Ser Tyr Val Asp Val Phe Leu Ser Phe Ile Ile Phe Leu Gly
           35                  40                  45

Phe Ile Glu Leu Ile His Gly Ile Arg Lys Ile Leu Val Trp Ser Gly
    50                  55                  60

Trp Lys Asn Gly Ser
65

<210> SEQ ID NO 31
<211> LENGTH: 6394
<212> TYPE: DNA
<213> ORGANISM: Artificial Sequence
<220> FEATURE:
<223> OTHER INFORMATION: Chemically-synthesized plasmid pGEN222Kh47

<400> SEQUENCE: 31

```
gaattaattc tgtggtagca cagaataatg aaaagtgtgt aaagaagggt aaaaaaaacc      60
gaatgcgagg catccggttg aaataggggt aaacagacat tcagaaatga atgacggtaa     120
taaataaagt taatgatgat agcgggagtt attctagttg cgagtgaagg ttttgttttg     180
acattcagtg ctgtcaaata cttaagaata agttattgat tttaaccttg aattattatt     240
gcttgatgtt aggtgcttat ttcgccattc cgcaataatc ttaaaaagtt cccttgcatt     300
tacattttga acatctata gcgataaatg aaacatctta aaagttttag tatcatattc      360
gtgttggatt attctgcatt tttggggaga atggacttgc cgactgatta atgagggtta     420
atcagtatgc agtggcataa aaaagcaaat aaaggcatat aacagatcga tcttaaacat     480
ccacaggagg atgggatcca aaataaggag gaaaaaaaaa tgactagcat gagtaaagga     540
gaagaacttt tcactggagt tgtcccaatt cttgttgaat tagatggtga tgttaatggg     600
cacaaatttt ctgtcagtgg agagggtgaa ggtgatgcaa catacggaaa acttacccct     660
aaatttattt gcactactgg aaaactacct gttccatggc caacacttgt cactactttc     720
tcttatggtg ttcaatgctt ttcccgttat ccggatcata tgaaacggca tgactttttc     780
aagagtgcca tgcccgaagg ttatgtacag gaacgcacta tatctttcaa agatgacggg     840
aactacaaga cgcgtgctga agtcaagttt gaaggtgata cccttgttaa tcgtatcgag     900
ttaaaggta ttgattttaa agaagatgga acattctcg acacaaaact cgagtacaac     960
tataactcac acaatgtata catcacggca gacaaacaaa agaatggaat caaagctaac    1020
ttcaaaattc gccacaacat tgaagatgga tccgttcaac tagcagacca ttatcaacaa    1080
aatactccaa ttggcgatgg ccctgtcctt ttaccagaca accattacct gtcgacacaa    1140
tctgcccttt cgaaagatcc caacgaaaag cgtgaccaca tggtccttct tgagtttgta    1200
actgctgctg ggattacaca tggcatggat gagctctaca ataatgaac tagttctagc    1260
tgataaccta gcgtcgacac tagcccgcct aatgagcggg ctttttttc tcggcctagc    1320
ctattaactt ccgttttcc agcctgacca gaccaaaatc tttcgaatcc catgaatcag    1380
ctcaataaaa ccaagaaata ttataaagct tagaaaaacg tcaacataag aattcccttc    1440
gccaacaatc gaagggatg aaagtgaaac caataagata gtaagaggta aactaaatat    1500
agccgtcaat tggtacagtt ttttataact cattttttt tcctccttat tttctagatt    1560
ccacacatta tacgagccgg aagcataaag tggaaagcct ggggtgcccg ctaggagata    1620
cttaacaggg aagtgagagg gccgcggcaa agccgttttt ccataggctc cgcccccctg    1680
acaagcatca cgaaatctga cgctcaaatc agtggtggcg aaacccgaca ggactataaa    1740
gataccaggc gtttccccct ggcggctccc tcgtgcgctc tcctgttcct gcctttcggt    1800
```

```
ttaccggtgt cattccgctg ttatggccgc gtttgtctca ttccacgcct gacactcagt    1860
tccgggtagg cagttcgctc caagctggac tgtatgcacg aaccccccgt tcagtccgac    1920
cgctgcgcct tatccggtaa ctatcgtctt gagtccaacc cggaaagaca tgcaaaagca    1980
ccactggcag cagccactgg taattgattt agaggagtta gtcttgaagt catgcgccgg    2040
ttaaggctaa actgaaagga caagttttgg tgactgcgct cctccaagcc agttacctcg    2100
gttcaaagag ttggtagctc agagaacctt cgaaaaaccg ccctgcaagg cggttttttc    2160
gttttcagag caagagatta cgcgcagacc aaaacgatct caagaagatc atcttattaa    2220
tcagataaaa tatttctagg atctaaaaca ctaggcccaa gagtttgtag aaacgcaaaa    2280
aggccatccg tcaggatggc cttctgctta atttgatgcc tggcagttta tggcgggcgt    2340
cctgcccgcc accctccggg ccgttgcttc gcaacgttca aatccgctcc cggcggattt    2400
gtcctactca ggagagcgtt caccgacaaa caacagataa aacgaaaggc ccagtctttc    2460
gactgagcct tcgtttttat ttgatgcctg gcagttccct actctcgcat ggggagaccc    2520
cacactacca tcggcgctac ggcgtttcac ttctgagttc ggcatggggt caggtgggac    2580
caccgcgcta ctgccgccag gcaaattctg ttttatcaga ccgcttctgc gttctgattt    2640
aatctgtatc aggctgaaaa tcttctctca tccgccaaaa cagccaagct ggatctggca    2700
aatcgctgaa tattccttt gtctccgacc atcaggcacc tgagtcgctg tcttttttcgt    2760 gacattcagt tcgctgcgct cacggctctg gcagtgaatg ggggtaaatg gcactacagg    2820
cgccttttat ggattcatgc aaggaaacta cccataatac aagaaaagcc cgtcacgggc    2880
ttctcagggc gttttatggc gggtctgcta tgtggtgcta tctgactttt tgctgttcag    2940
cagttcctgc cctctgattt tccagtctga ccacttcgga ttatcccgtg acaggtcatt    3000
cagactggct aatgcaccca gtaaggcagc ggtatcatca acaggcttac ccgtcttact    3060
gtcaaccgga tctaaaacac tagcccaacc tttcatagaa ggcggcggtg gaatcgaaat    3120
ctcgtgatgg caggttgggc gtcgcttggt cggtcatttc gaaccccaga gtcccgctca    3180
gaagaactcg tcaagaaggc gatagaaggc gatgcgctgc gaatcgggag cggcgatacc    3240
gtaaagcacg aggaagcggt cagcccattc gccgccaagc tcttcagcaa tatcacgggc    3300
agccaacgct atgtcctgat agcggtccgc cacacccagc cggccacagt cgatgaatcc    3360
agaaaagcgg ccattttcca ccatgatatt cggcaagcag gcatcgccat gggtcacgac    3420
gagatcctcg ccgtcgggca tgcgcgcctt gagcctggcg aacagttcgg ctggcgcgag    3480
cccctgatgc tcttcgtcca gatcatcctg atcgacaaga ccggcttcca tccgagtacg    3540
tgctcgctcg atgcgatgtt tcgcttggtg gtcgaatggg caggtagccg gatcaagcgt    3600
atgcagccgc cgcattgcat cagccatgat ggatactttc tcggcaggag caaggtgaga    3660
tgacaggaga tcctgccccg gcacttcgcc caatagcagc cagtcccttc ccgcttcagt    3720
gacaacgtcg agcacagctg cgcaaggaac gcccgtcgtg gccagccacg atagccgcgc    3780
tgcctcgtcc tgcagttcat tcagggcacc ggacaggtcg gtcttgacaa aaagaaccgg    3840
gcgcccctgc gctgacagcc ggaacacggc ggcatcagag cagccgattg tctgttgtgc    3900
ccagtcatag ccgaatagcc tctccaccca gcggccgga gaacctgcgt gcaatccatc    3960
ttgttcaatc atgcgaaacg atcctcatcc tgtctcttga tcagatcttg atcccctgcg    4020
ccatcagatc cttggcggca agaaagccat ccagtttact ttgcagggct tcccaacctt    4080
accagagggc gccccagccg tgcaattcc ggttcgctgc tagacaacat cagcaaggag    4140
aaaggggcta ccggcgaacc agcagcccct ttataaaggc gcttcagtag tcagaccagc    4200
```

```
atcagtcctg aaaaggcggg cctgcgcccg cctccaggtt gctacttacc ggattcgtaa    4260
gccatgaaag ccgccacctc cctgtgtccg tctctgtaac gaatctcgca cagcgatttt    4320
cgtgtcagat aagtgaatat caacagtgtg agacacacga tcaacacaca ccagacaagg    4380
gaacttcgtg gtagtttcat ggccttcttc tccttgcgca aagcgcggta agaggctatc    4440
ctgatgtgga ctagacatag ggatgcctcg tggtggttaa tgaaaattaa cttactacgg    4500
ggctatcttc tttctgccac acaacacggc aacaaaccac cttcacgtca tgaggcagaa    4560
agcctcaagc gccgggcaca tcatagccca tatacctgca cgctgaccac actcactttc    4620
cctgaaaata atccgctcat tcagaccgtt cacgggaaat ccgtgtgatt gttgccgcat    4680
cacgctgcct cccggagttt gtctcgagca cttttgttac ccgccaaaca aacccaaaa    4740
acaacccata cccaacccaa taaaacacca aacaagaca ataatcatt gattgatggt    4800
tgaaatgggg taaacttgac aaacaaaccc acttaaaacc caaaacatac ccaaacacac    4860
accaaaaaaa caccataagg agttttataa atgttggtat tcattgatga cggttcaaca    4920
aacatcaaac tacagtggca ggaaagcgac ggaacaatta aacagcacat tagcccgaac    4980
agcttcaaac gcgagtgggc agtctctttt ggtgataaaa aggtctttaa ctacacactg    5040
aacggcgaac agtattcatt tgatccaatc agcccggatg ctgtagtcac aaccaatatc    5100
gcatggcaat acagcgacgt taatgtcgtt gcagtgcatc acgccttact gaccagtggt    5160
ctgccggtaa gcgaagtgga tattgtttgc acacttcctc tgacagagta ttacgacaga    5220
aataaccaac ccaatacgga aaatattgag cgtaagaaag caaacttccg gaaaaaaatt    5280
acattaaatg gcgggatac attcacaata aaagatgtaa aagtcatgcc tgaatctata    5340
ccggcaggtt atgaagttct acaagaactg gatgagttag attctttatt aattatagat    5400
ctcgggggca ccacattaga tatttctcag gtaatgggga aattatcggg gatcagtaaa    5460
atatacggag actcatctct tggtgtctct ctggttacat ctgcagtaaa agatgccctt    5520
tctcttgcga gaacaaaagg aagtagctat cttgctgacg atataatcat tcacagaaaa    5580
gataataact atctgaagca acgaattaat gatgagaaca aaatatcaat agtcaccgaa    5640
gcaatgaatg aagcacttcg taaacttgag caacgtgtat taaatacgct caatgaattt    5700
tctggtttata ctcatgttat ggttataggc ggtggcgcag aattaatatg cgatgcagta    5760
aaaaaacaca cacagattcg tgatgaacgt ttttttcaaaa ccaataactc tcaatatgat    5820
ttagttaacg gtatgtatct cataggtaat taatgatgga caagcgcaga accattgcct    5880
tcaaactaaa tccagatgta aatcaaacag ataaaattgt ttgtgataca ctggacagta    5940
tcccgcaagg ggaacgaagc cgccttaacc gggccgcact gacggcaggt ctggccttat    6000
acagacaaga tccccggacc cctttccttt tatgtgagct gctgacgaaa gaaaccacat    6060
tttcagatat cgtgaatata ttgagatcgc tatttccaaa agagatggcc gattttaatt    6120
cttcaatagt cactcaatcc tcttcacaac aagagcaaaa aagtgatgaa gagaccaaaa    6180
aaaatgcgat gaagctaata aattaattca attattattg agttccctt atccactatc    6240
aggctggata aagggaactc aatcaagtta ttttcttacc agtcattaca taatcgttat    6300
tatgaaataa tcgtttgcac tgtctctgtt attcaggcaa tttcaataaa ggcacttgct    6360
cacgctctgt cattttctga aactcttcat gctg                               6394
```

<210> SEQ ID NO 32
<211> LENGTH: 8474
<212> TYPE: DNA
<213> ORGANISM: Artificial Sequence
<220> FEATURE:

<223> OTHER INFORMATION: Chemically-synthesized plasmid pSEC91-83

<400> SEQUENCE: 32

```
gaattctgtg gtagcacaga ataatgaaaa gtgtgtaaag aagggtaaaa aaaaccgaat      60
gcgaggcatc cggttgaaat aggggtaaac agacattcag aaatgaatga cgtaataaaa     120
taaagttaat gatgatagcg ggagttattc tagttgcgag tgaaggtttt gttttgacat     180
tcagtgctgt caaatactta agaataagtt attgatttta accttgaatt attattgctt     240
gatgttaggt gcttatttcg ccattccgca ataatcttaa aaagttccct tgcatttaca     300
ttttgaaaca tctatagcga taaatgaaac atcttaaaag ttttagtatc atattcgtgt     360
tggattattc tgcatttttg gggagaatgg acttgccgac tgattaatga gggttaatca     420
gtatgcagtg gcataaaaaa gcaaataaag gcatataaca gatcgatctt aaacatccac     480
aggaggatgg gatccaaaat aaggaggaaa aaaaaatgac tagtattttt gcagaacaaa     540
ctgtagaggt agttaaaagc gcgatcgaaa ccgcagatgg ggcattagat ctttataaca     600
aataccctcga ccaggtcatc ccctggaaga cctttgatga aaccataaaa gagttaagcc     660
gttttaaaca ggagtactcg caggaagctt ctgttttagt tggtgatatt aaagttttgc     720
ttatggacag ccaggacaag tattttgaag cgacacaaac tgtttatgaa tggtgtggtg     780
tcgtgacgca attactctca gcgtatattt tactatttga tgaatataat gagaaaaaag     840
catcagccca gaaagacatt ctcattagga tattagatga tggtgtcaag aaactgaatg     900
aagcgcaaaa atctctcctg acaagttcac aaagtttcaa caacgcttcc ggaaaactgc     960
tggcattaga tagccagtta actaatgatt tttcggaaaa aagtagttat ttccagtcac    1020
aggtggatag aattcgtaag gaagcttatg ccggtgctgc agccggcata gtcgccggtc    1080
cgtttggatt aattattttcc tattctattg ctgcgggcgt gattgaaggg aaattgattc    1140
cagaattgaa taacaggcta aaaacagtgc aaaatttctt tactagctta tcagctacag    1200
tgaaacaagc gaataaagat atcgatgcgg caaaattgaa attagccact gaaatagcag    1260
caattgggga gataaaaacg gaaaccgaaa caaccagatt ctacgttgat tatgatgatt    1320
taatgctttc tttattaaaa ggagctgcaa agaaaatgat taacacctgt aatgaatacc    1380
aacaacgtca tggtaagaag acgcttttcg aggttcctga cgtcgctagc gaagttaaac    1440
aggagaaccg tctgctgaat gaaagcgaaa gcagcagcca gggcctgctg ggctattatt    1500
ttagcgatct gaattttcag gcaccgatgg tggttaccag cagcaccacc ggcgatctga    1560
gcattccgag cagcgagctg gaaaatattc cgagcgaaaa ccagtatttt cagagcgcca    1620
tttggagcgg ctttatcaaa gttaagaaaa gcgatgaata cctttgcc accagcgccg    1680
ataatcatgt taccatgtgg gttgatgacc aggaagttat caacaaagcg agcaatagca    1740
acaaaatccg tctcgagaaa ggccgtctgt atcagattaa aattcagtat cagcgtgaaa    1800
atccgaccga aaaggcctg gattttaagc tgtattggac cgatagccag aataaaaaag    1860
aagtgattag cagcgataac ctgcaattgc cggaactgaa acagaaaagc agcaacagcc    1920
gtaaaaaacg tagtactagt gccggcccga ccgttccgga ccgtgacaat gatggcatcc    1980
cggatagcct ggaggttgaa ggctataccg ttgatgttaa aaataaacgt acctttctga    2040
gcccatggat tagcaatatt catgaaaaaa aaggcctgac caaatataaa agcagcccgg    2100
aaaaatggag caccgccagc gatccgtata gcgattttga aaagttacc ggccgtattg    2160
ataaaaatgt tagcccggag gcacgtcatc cgctggtggc agcctatccg attgttcatg    2220
ttgatatgga gaatattatc ctgagcaaaa atgaggatca gagcacccag aataccgata    2280
```

```
gcgaaacccg taccattagc aaaaatacca gcaccagccg tacccatacc agcgaagttc    2340
atggcaatgc agaagtgcat gcgagcttct ttgatattgg tggcagcgtt tctgcaggat    2400
ttagcaattc gaattcaagc accgtggcga ttgatcatag cctgagcctg caggcgaac     2460 gtacctgggc cgaaacgatg ggtctgaata ccgccgatac cgcacgtctg aatgccaata    2520
ttcgttatgt taataccggc accgccccga tctataacgt gctgccgacc accagcctgg    2580
tgctgggcaa aaatcagacc ctcgcgacaa ttaaagccaa agaaaaccag ctgagccaga    2640
ttctggcacc gaataactat tatccgagca aaaacttggc gccaatcgca ctgaatgcac    2700
aggacgattt tagcagcacc ccgattacca tgaattataa tcagtttctg gagctggaaa    2760
aaaccaaaca gctgcgtctg gataccgatc aggtttatgg caatattgca acctataatt    2820
ttgaaaatgg ccgtgtgcgt gtggataccg gcagcaactg gagcgaagtg ctgccgcaga    2880
ttcaggaaac caccgcacgt atcattttta atggcaaaga tttaaatctg gttgaacgtc    2940
gtattgcggc cgttaatccg agcgatccgc tggaaaccac caaaccggat atgaccctga    3000
aagaagccct gaaaattgca tttggcttta cgaaccgaa tggcaacctt cagtatcagg     3060
gcaaagacat taccgaattt gattttaatt ttgaccagca gaccagccag aatatcaaaa    3120
atcagctggc ggagctcaac gcgaccaaca tttataccgt tctggataaa atcaaactga    3180
atgcaaaaat gaatattctg attcgtgata acgttttca ttatgatcgt aataacattg     3240
cagttggcgc ggatgagagc gttgtgaaag aggcccatcg tgaagttatt aatagcagca    3300
ccgagggcct gctgctgaat attgataaag atattcgtaa aattctgagc ggttatattg    3360
ttgaaattga agataccgaa ggcctgaaag aagttattaa cgaccgttat gatatgctga    3420
atattagcag cctgcgtcag gatggcaaaa cctttattga ttttaagaaa tataatgata    3480
agcttccgct gtatattagc aatccgaatt ataaagttaa tgtttatgcc gttaccaaag    3540
aaaacaccat tatcaatccg agcgagaatg gcgataccag caccaacggc atcaagaaaa    3600
ttctgatctt tagcaaaaaa ggctatgaga ttggctaatg acctagcgtc gacactagcc    3660
cgcctaatga gcgggctttt ttttctcggc ctaggagata cttaacaggg aagtgagagg    3720
gccgcggcaa agccgttttt ccataggctc cgcccccctg acaagcatca cgaaatctga    3780
cgctcaaatc agtggtggcg aaacccgaca ggactataaa gataccaggc gtttccccct    3840
ggcggctccc tcgtgcgctc tcctgttcct gcctttcggt ttaccggtgt cattccgctg    3900
ttatggccgc gtttgtctca ttccacgcct gacactcagt tccgggtagg cagttcgctc    3960
caagctggac tgtatgcacg aaccccccgt tcagtccgac cgctgcgcct tatccggtaa    4020
ctatcgtctt gagtccaacc cggaaagaca tgcaaaagca ccactggcag cagccactgg    4080
taattgattt agaggagtta gtcttgaagt catgcgccgg ttaaggctaa actgaaagga    4140
caagttttgg tgactgcgct cctccaagcc agttacctcg gttcaaagag ttggtagctc    4200
agagaacctc gaaaaaccg ccctgcaagg cggttttttc gttttcagag caagagatta     4260
cgcgcagacc aaaacgatct caagaagatc atcttattaa tcagataaaa tatttctagg    4320
atctaaaaca ctaggcccaa gagtttgtag aaacgcaaaa aggccatccg tcaggatggc    4380
cttctgctta atttgatgcc tggcagttta tggcgggcgt cctgcccgcc accctccggg    4440
ccgttgcttc gcaacgttca aatccgctcc cggcggattt gtcctactca ggagagcgtt    4500
caccgacaaa caacagataa aacgaaaggc ccagtctttc gactgagcct ttcgttttat    4560
ttgatgcctg gcagttccct actctcgcat ggggagaccc cacactacca tcggcgctac    4620
ggcgtttcac ttctgagttc ggcatggggt caggtgggac caccgcgcta ctgccgccag    4680
```

```
gcaaattctg ttttatcaga ccgcttctgc gttctgattt aatctgtatc aggctgaaaa    4740
tcttctctca tccgccaaaa cagccaagct ggatctggca aatcgctgaa tattcctttt    4800
gtctccgacc atcaggcacc tgagtcgctg tcttttcgt gacattcagt tcgctgcgct     4860
cacggctctg gcagtgaatg ggggtaaatg gcactacagg cgccttttat ggattcatgc    4920
aaggaaacta cccataatac aagaaaagcc cgtcacgggc ttctcagggc gttttatggc    4980
gggtctgcta tgtggtgcta tctgactttt tgctgttcag cagttcctgc cctctgattt    5040
tccagtctga ccacttcgga ttatcccgtg acaggtcatt cagactggct aatgcaccca    5100
gtaaggcagc ggtatcatca acaggcttac ccgtcttact gtcaaccgga tctaaaacac    5160
tagcccaacc tttcatagaa ggcggcggtg aatcgaaat ctcgtgatgg caggttgggc     5220
gtcgcttggt cggtcatttc gaaccccaga gtcccgctca aagaactcg tcaagaaggc     5280 gatagaaggc gatgcgctgc gaatcgggag cggcgatacc gtaaagcacg aggaagcggt    5340
cagcccattc gccgccaagc tcttcagcaa tatcacgggt agccaacgct atgtcctgat    5400
agcggtccgc cacacccagc cggccacagt cgatgaatcc agaaaagcgg ccattttcca    5460
ccatgatatt cggcaagcag gcatcgccat gggtcacgac gagatcctcg ccgtcgggca    5520
tgcgcgcctt gagcctggcg aacagttcgg ctggcgcgag cccctgatgc tcttcgtcca    5580
gatcatcctg atcgacaaga ccggcttcca tccgagtacg tgctcgctcg atgcgatgtt    5640
tcgcttggtg gtcgaatggg caggtagccg gatcaagcgt atgcagccgc cgcattgcat    5700
cagccatgat ggatactttc tcggcaggag caaggtgaga tgacaggaga tcctgccccg    5760
gcacttcgcc caatagcagc cagtcccttc ccgcttcagt gacaacgtcg agcacagctg    5820
cgcaaggaac gcccgtcgtg gccagccacg atagccgcgc tgcctcgtcc tgcagttcat    5880
tcagggcacc ggacaggtcg gtcttgacaa aaagaaccgg gcgcccctgc gctgacagcc    5940
ggaacacggc ggcatcagag cagccgattg tctgttgtgc ccagtcatag ccgaatagcc    6000
tctccaccca gcggccgga gaacctgcgt gcaatccatc ttgttcaatc atgcgaaacg      6060
atcctcatcc tgtctcttga tcagatcttg atcccctgcg ccatcagatc cttggcggca    6120
agaaagccat ccagtttact ttgcagggct tcccaacctt accagagggc gccccagccg    6180
tggcaattcc ggttcgctgc tagacaacat cagcaaggag aaaggggcta ccggcgaacc    6240
agcagcccct ttataaaggc gcttcagtag tcagaccagc atcagtcctg aaaaggcggg    6300
cctgcgcccg cctccaggtt gctacttacc ggattcgtaa gccatgaaag ccgccacctc    6360
cctgtgtccg tctctgtaac gaatctcgca cagcgatttt cgtgtcagat aagtgaatat    6420
caacagtgtg agacacacga tcaacacaca ccagacaagg gaacttcgtg gtagtttcat    6480
ggccttcttc tccttgcgca aagcgcggta agaggctatc ctgatgtgga ctagacatag    6540
ggatgcctcg tggtggttaa tgaaaattaa cttactacgg ggctatcttc tttctgccac    6600
acaacacggc aacaaaccac cttcacgtca tgaggcagaa agcctcaagc gccgggcaca    6660
tcatagccca tatacctgca cgctgaccac actcactttc cctgaaaata atccgctcat    6720
tcagaccgtt cacgggaaat ccgtgtgatt gttgccgcat cacgctgcct cccggagttt    6780
gtctcgagca cttttgttac ccgccaaaca aacccaaaa acaaacccata cccaacccaa     6840 taaaacacca aaacaagaca aataatcatt gattgatggt tgaaatgggg taaacttgac    6900
aaacaaaccc acttaaaacc caaaacatac ccaaacacac accaaaaaaa caccataagg    6960
agttttataa atgttggtat tcattgatga cggttcaaca aacatcaaac tacagtggca    7020
ggaaagcgac ggaacaatta aacagcacat tagcccgaac agcttcaaac gcgagtgggc    7080
```

```
agtctctttt ggtgataaaa aggtctttaa ctacacactg aacggcgaac agtattcatt    7140
tgatccaatc agcccggatg ctgtagtcac aaccaatatc gcatggcaat acagcgacgt    7200
taatgtcgtt gcagtgcatc acgccttact gaccagtggt ctgccggtaa gcgaagtgga    7260
tattgtttgc acacttcctc tgacagagta ttacgacaga aataaccaac ccaatacgga    7320
aaatattgag cgtaagaaag caaacttccg gaaaaaaatt acattaaatg gcggggatac    7380
attcacaata aaagatgtaa aagtcatgcc tgaatctata ccggcaggtt atgaagttct    7440
acaagaactg gatgagttag attctttatt aattatagat ctcggggca ccacattaga    7500
tatttctcag gtaatgggga aattatcggg gatcagtaaa atatacgag actcatctct    7560
tggtgtctct ctggttacat ctgcagtaaa agatgcccct tctcttgcga gaacaaaagg    7620
aagtagctat cttgctgacg atataatcat tcacagaaaa gataataact atctgaagca    7680
acgaattaat gatgagaaca aaatatcaat agtcaccgaa gcaatgaatg aagcacttcg    7740
taaacttgag caacgtgtat taaatacgct caatgaattt tctggttata ctcatgttat    7800
ggttataggc ggtggcgcag aattaatatg cgatgcagta aaaaaacaca cacagattcg    7860
tgatgaacgt ttttttcaaaa ccaataactc tcaatatgat ttagttaacg gtatgtatct    7920
cataggtaat taatgatgga caagcgcaga accattgcct tcaaactaaa tccagatgta    7980
aatcaaacag ataaaattgt ttgtgataca ctggacagta tcccgcaagg ggaacgaagc    8040
cgccttaacc gggccgcact gacggcaggt ctggccttat acagacaaga tccccggacc    8100
cctttccttt tatgtgagct gctgacgaaa gaaaccacat tttcagatat cgtgaatata    8160
ttgagatcgc tatttccaaa agagatggcc gattttaatt cttcaatagt cactcaatcc    8220
tcttcacaac aagagcaaaa aagtgatgaa gagaccaaaa aaaatgcgat gaagctaata    8280
aattaattca attattattg agttcccttt atccactatc aggctggata aagggaactc    8340
aatcaagtta ttttcttacc agtcattaca taatcgttat tatgaaataa tcgtttgcac    8400
tgtctctgtt attcaggcaa tttcaataaa ggcacttgct cacgctctgt cattttctga    8460
aactcttcat gctg                                                      8474
```

<210> SEQ ID NO 33
<211> LENGTH: 1040
<212> TYPE: PRT
<213> ORGANISM: Artificial Sequence
<220> FEATURE:
<223> OTHER INFORMATION: Chemically-synthesized ClyA-PA83 fusion protein

<400> SEQUENCE: 33

Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
                20                  25                  30

Gln Val Ile Pro Trp Lys Thr Phe Asp Glu Thr Ile Lys Glu Leu Ser
            35                  40                  45

Arg Phe Lys Gln Glu Tyr Ser Gln Glu Ala Ser Val Leu Val Gly Asp
        50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn

```
            115                 120                 125
Glu Ala Gln Lys Ser Leu Leu Thr Ser Ser Gln Ser Phe Asn Asn Ala
130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Gly Ile Val Ala Gly Pro Phe Gly Leu
                180                 185                 190

Ile Ile Ser Tyr Ser Ile Ala Ala Gly Val Ile Glu Gly Lys Leu Ile
                195                 200                 205

Pro Glu Leu Asn Asn Arg Leu Lys Thr Val Gln Asn Phe Phe Thr Ser
210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
                260                 265                 270

Leu Leu Lys Gly Ala Ala Lys Lys Met Ile Asn Thr Cys Asn Glu Tyr
                275                 280                 285

Gln Gln Arg His Gly Lys Lys Thr Leu Phe Glu Val Pro Asp Val Ala
290                 295                 300

Ser Glu Val Lys Gln Glu Asn Arg Leu Leu Asn Glu Ser Glu Ser Ser
305                 310                 315                 320

Ser Gln Gly Leu Leu Gly Tyr Tyr Phe Ser Asp Leu Asn Phe Gln Ala
                325                 330                 335

Pro Met Val Val Thr Ser Ser Thr Thr Gly Asp Leu Ser Ile Pro Ser
                340                 345                 350

Ser Glu Leu Glu Asn Ile Pro Ser Glu Asn Gln Tyr Phe Gln Ser Ala
                355                 360                 365

Ile Trp Ser Gly Phe Ile Lys Val Lys Lys Ser Asp Glu Tyr Thr Phe
370                 375                 380

Ala Thr Ser Ala Asp Asn His Val Thr Met Trp Val Asp Asp Gln Glu
385                 390                 395                 400

Val Ile Asn Lys Ala Ser Asn Ser Asn Lys Ile Arg Leu Glu Lys Gly
                405                 410                 415

Arg Leu Tyr Gln Ile Lys Ile Gln Tyr Gln Arg Glu Asn Pro Thr Glu
                420                 425                 430

Lys Gly Leu Asp Phe Lys Leu Tyr Trp Thr Asp Ser Gln Asn Lys Lys
                435                 440                 445

Glu Val Ile Ser Ser Asp Asn Leu Gln Leu Pro Glu Leu Lys Gln Lys
                450                 455                 460

Ser Ser Asn Ser Arg Lys Lys Arg Ser Thr Ser Ala Gly Pro Thr Val
465                 470                 475                 480

Pro Asp Arg Asp Asn Asp Gly Ile Pro Asp Ser Leu Glu Val Glu Gly
                485                 490                 495

Tyr Thr Val Asp Val Lys Asn Lys Arg Thr Phe Leu Ser Pro Trp Ile
                500                 505                 510

Ser Asn Ile His Glu Lys Lys Gly Leu Thr Lys Tyr Lys Ser Ser Pro
                515                 520                 525

Glu Lys Trp Ser Thr Ala Ser Asp Pro Tyr Ser Asp Phe Glu Lys Val
530                 535                 540
```

```
                              -continued

Thr Gly Arg Ile Asp Lys Asn Val Ser Pro Glu Ala Arg His Pro Leu
545                 550                 555                 560

Val Ala Ala Tyr Pro Ile Val His Val Asp Met Glu Asn Ile Ile Leu
                565                 570                 575

Ser Lys Asn Glu Asp Gln Ser Thr Gln Asn Thr Asp Ser Glu Thr Arg
            580                 585                 590

Thr Ile Ser Lys Asn Thr Ser Thr Ser Arg Thr His Thr Ser Glu Val
        595                 600                 605

His Gly Asn Ala Glu Val His Ala Ser Phe Phe Asp Ile Gly Gly Ser
    610                 615                 620

Val Ser Ala Gly Phe Ser Asn Ser Asn Ser Thr Val Ala Ile Asp
625                 630                 635                 640

His Ser Leu Ser Leu Ala Gly Glu Arg Thr Trp Ala Glu Thr Met Gly
                645                 650                 655

Leu Asn Thr Ala Asp Thr Ala Arg Leu Asn Ala Asn Ile Arg Tyr Val
                660                 665                 670

Asn Thr Gly Thr Ala Pro Ile Tyr Asn Val Leu Pro Thr Thr Ser Leu
            675                 680                 685

Val Leu Gly Lys Asn Gln Thr Leu Ala Thr Ile Lys Ala Lys Glu Asn
        690                 695                 700

Gln Leu Ser Gln Ile Leu Ala Pro Asn Asn Tyr Tyr Pro Ser Lys Asn
705                 710                 715                 720

Leu Ala Pro Ile Ala Leu Asn Ala Gln Asp Asp Phe Ser Ser Thr Pro
                725                 730                 735

Ile Thr Met Asn Tyr Asn Gln Phe Leu Glu Leu Glu Lys Thr Lys Gln
                740                 745                 750

Leu Arg Leu Asp Thr Asp Gln Val Tyr Gly Asn Ile Ala Thr Tyr Asn
            755                 760                 765

Phe Glu Asn Gly Arg Val Arg Val Asp Thr Gly Ser Asn Trp Ser Glu
        770                 775                 780

Val Leu Pro Gln Ile Gln Glu Thr Thr Ala Arg Ile Ile Phe Asn Gly
785                 790                 795                 800

Lys Asp Leu Asn Leu Val Glu Arg Arg Ile Ala Ala Val Asn Pro Ser
                805                 810                 815

Asp Pro Leu Glu Thr Thr Lys Pro Asp Met Thr Leu Lys Glu Ala Leu
                820                 825                 830

Lys Ile Ala Phe Gly Phe Asn Glu Pro Asn Gly Asn Leu Gln Tyr Gln
            835                 840                 845

Gly Lys Asp Ile Thr Glu Phe Asp Phe Asn Phe Asp Gln Gln Thr Ser
        850                 855                 860

Gln Asn Ile Lys Asn Gln Leu Ala Glu Leu Asn Ala Thr Asn Ile Tyr
865                 870                 875                 880

Thr Val Leu Asp Lys Ile Lys Leu Asn Ala Lys Met Asn Ile Leu Ile
                885                 890                 895

Arg Asp Lys Arg Phe His Tyr Asp Arg Asn Asn Ile Ala Val Gly Ala
                900                 905                 910

Asp Glu Ser Val Val Lys Glu Ala His Arg Glu Val Ile Asn Ser Ser
            915                 920                 925

Thr Glu Gly Leu Leu Leu Asn Ile Asp Lys Asp Ile Arg Lys Ile Leu
        930                 935                 940

Ser Gly Tyr Ile Val Glu Ile Glu Asp Thr Glu Gly Leu Lys Glu Val
945                 950                 955                 960

Ile Asn Asp Arg Tyr Asp Met Leu Asn Ile Ser Ser Leu Arg Gln Asp
                965                 970                 975
```

```
Gly Lys Thr Phe Ile Asp Phe Lys Lys Tyr Asn Asp Lys Leu Pro Leu
            980                 985                 990

Tyr Ile Ser Asn Pro Asn Tyr Lys  Val Asn Val Tyr Ala  Val Thr Lys
        995                 1000                1005

Glu Asn  Thr Ile Ile Asn Pro  Ser Glu Asn Gly Asp  Thr Ser Thr
    1010                1015                1020

Asn Gly  Ile Lys Lys Ile Leu  Ile Phe Ser Lys Lys  Gly Tyr Glu
    1025                1030                1035

Ile Gly
    1040

<210> SEQ ID NO 34
<211> LENGTH: 447
<212> TYPE: PRT
<213> ORGANISM: Artificial Sequence
<220> FEATURE:
<223> OTHER INFORMATION: Chemically-synthesized ClyA::D4 fusion protein

<400> SEQUENCE: 34

Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
            85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
            165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
            245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285
```

Gln Gln Arg His Gly Lys Lys Thr Leu Phe Glu Val Pro Asp Val Ala
            290                 295                 300

Ser Lys Arg Phe His Tyr Asp Arg Asn Asn Ile Ala Val Gly Ala Asp
305                 310                 315                 320

Glu Ser Val Val Lys Glu Ala His Arg Glu Val Ile Asn Ser Ser Thr
            325                 330                 335

Glu Gly Leu Leu Leu Asn Ile Asp Lys Asp Ile Arg Lys Ile Leu Ser
            340                 345                 350

Gly Tyr Ile Val Glu Ile Glu Asp Thr Glu Gly Leu Lys Glu Val Ile
            355                 360                 365

Asn Asp Arg Tyr Asp Met Leu Asn Ile Ser Ser Leu Arg Gln Asp Gly
            370                 375                 380

Lys Thr Phe Ile Asp Phe Lys Lys Tyr Asn Asp Lys Leu Pro Leu Tyr
385                 390                 395                 400

Ile Ser Asn Pro Asn Tyr Lys Val Asn Val Tyr Ala Val Thr Lys Glu
            405                 410                 415

Asn Thr Ile Ile Asn Pro Ser Glu Asn Gly Asp Thr Ser Thr Asn Gly
            420                 425                 430

Ile Lys Lys Ile Leu Ile Phe Ser Lys Lys Gly Tyr Glu Ile Gly
            435                 440                 445

<210> SEQ ID NO 35
<211> LENGTH: 453
<212> TYPE: DNA
<213> ORGANISM: Bacillus anthracis

<400> SEQUENCE: 35
tagtaatgaa ctagtaaacg ttttcattat gatcgtaata acatcgcagt tggggcggat      60
gagtcagtag ttaaggaggc tcatcgtgaa gtaattaatt cgtcaacaga gggattattg     120
ttaaatattg ataaggatat ccgtaaaatc ttatccggat atattgtaga aattgaagat     180
actgaagggc ttaagaagt tatcaatgac cgttatgata tgttgaatat ttctagttta     240
cgtcaagatg gaaaaacatt tatcgatttt aaaaaatata atgataaatt accgttatat     300
atcagtaatc cgaattataa ggtaaatgta tatgctgtta ctaaagaaaa cactattatt     360
aatcctagtg agaatgggga taccagcacc aacgggatca gaaaatttt aatctttct     420 aaaaaaggct atgagatcgg ataatgacct agg                                  453

<210> SEQ ID NO 36
<211> LENGTH: 144
<212> TYPE: PRT
<213> ORGANISM: Bacillus anthracis

<400> SEQUENCE: 36

Thr Ser Lys Arg Phe His Tyr Asp Arg Asn Asn Ile Ala Val Gly Ala
1               5                   10                  15

Asp Glu Ser Val Val Lys Glu Ala His Arg Glu Val Ile Asn Ser Ser
            20                  25                  30

Thr Glu Gly Leu Leu Leu Asn Ile Asp Lys Asp Ile Arg Lys Ile Leu
        35                  40                  45

Ser Gly Tyr Ile Val Glu Ile Glu Asp Thr Glu Gly Leu Lys Glu Val
    50                  55                  60

Ile Asn Asp Arg Tyr Asp Met Leu Asn Ile Ser Ser Leu Arg Gln Asp
65                  70                  75                  80

Gly Lys Thr Phe Ile Asp Phe Lys Lys Tyr Asn Asp Lys Leu Pro Leu
                85                  90                  95

-continued

```
Tyr Ile Ser Asn Pro Asn Tyr Lys Val Asn Val Tyr Ala Val Thr Lys
            100                 105                 110

Glu Asn Thr Ile Ile Asn Pro Ser Glu Asn Gly Asp Thr Ser Thr Asn
            115                 120                 125

Gly Ile Lys Lys Ile Leu Ile Phe Ser Lys Lys Gly Tyr Glu Ile Gly
            130                 135                 140
```

MICROCIN H47 PLASMID SELECTION SYSTEM

This invention was made with support pursuant to National Institute of Health Grant Nos. A1057168 and A1025461. The U.S. government has certain rights in this invention.

BACKGROUND OF THE INVENTION

Bacterial live vector vaccines represent a vaccine development strategy that offers exceptional flexibility. With this approach, genes that encode protective antigens of unrelated bacterial, viral or parasitic pathogens are expressed in an attenuated bacterial vaccine strain that delivers these foreign antigens to the immune system, thereby eliciting a relevant immune response.

With the advent of powerful recombinant bioengineering techniques, it is now possible to genetically attenuate pathogenic bacteria to create safe and immunogenic live oral vaccines. Bacterial live vectors include attenuated enteric pathogens (e.g., *Salmonella enterica, Shigella, Vibrio cholerae*)[2, 20, 21, 64, 84, 89], commensals (e.g., *Lactobacillus, Streptococcus gordonii*)[62, 113] and licensed vaccine strains (e.g., BCG)[29].

Such vaccines can be additionally engineered to express protective antigens from unrelated human pathogens, creating multivalent live vector vaccine strains. Typically, these foreign proteins are expressed within live vectors from multicopy expression plasmids that do not encode transfer functions and are not considered to be self-transmissible. Two fundamental lessons are becoming clear in live vector vaccinology: 1) multicopy expression plasmids can provide a gene dosage effect to enhance the level of expression of foreign antigens, and 2) in order to achieve enhanced immunogenicity from a gene dosage effect in live vectors, these multicopy plasmids must be genetically stabilized, particularly if expression of the foreign antigens metabolically stresses the live vector.

Antibiotic resistance markers are usually inserted into expression plasmids for selection purposes after introduction of plasmids into live vectors. Until recently, these resistance markers were considered to pose no risk for complicating or causing failure of clinical antimicrobial treatments for three important reasons: 1) the expression plasmids (and accompanying resistance markers) could not be efficiently mobilized from live vector donors to a recipient[52], 2) the plasmid markers used encoded resistance to antibiotics not in widespread medical use, and 3) with no relevant antibiotic selective pressure, even rare plasmid transfers would not lead to de novo resistance becoming established within a new bacterial population[52].

However, a growing body of evidence now clearly points to an inherent plasticity in the bacterial genome of intestinal microbes that allows rapid adaptation to environmental pressures using a striking variety of genetic mechanisms[13, 43, 86]. Indeed, intestinal bacteria have been proposed to act as a reservoir for mobile resistance cassettes and associated genes of metabolic importance, which cannot only be exchanged and maintained between resident flora of intestinal biofilms[55], but might also be acquired or horizontally transferred to various genera of bacteria passing through the colon[87]. Examples of unexpected gene mobilization have recently been documented that challenge conventional thinking in bacterial genetics.

In elegant experiments designed to examine plasmid dynamics in biofilms, Maeda et al.[58, 59] demonstrated the rapid transfer of a common multicopy pUC-like plasmid from a laboratory *Escherichia coli* K-12 DH5α strain to a recipient *E. coli* strain in the absence of antibiotic selection or any known fertility factors, R-factors, or other recognized conjugation or transduction functions. It was hypothesized that in situ horizontal transfer of plasmids occurred as DNA was released from dead and lysing "donor" bacteria and transferred into recipient bacteria by an unknown mechanism. Another unexpected example of in situ horizontal transfer was described by Ferguson et al.[31], where conjugative plasmids were observed to be mobilized intracellularly at high frequency between *Salmonella enterica* strains residing within epithelial cell membrane-bound vacuoles. The frequency of plasmid transfer by conjugation was shown to be dependent on the probability of coinfection of the same epithelial cell by both donor and recipient; intracellular recombinants appeared by three hours after donor invasion and accumulated steadily over time. The authors posed the intriguing possibility of horizontal gene transfer between unrelated species of intracellular bacteria residing in the same target cell. Such examples clearly reveal the unexpected mobility of plasmids within a bacterial community, even in the absence of recognized selective pressures.

Genes encoding resistance to kanamycin (and the closely related antibiotic neomycin) have become the markers of choice for selection of recombinant plasmid DNA intended for use in human vaccines. These antimicrobials are used only occasionally in treatments of the gastrointestinal tract prior to elective colon surgery to avoid post-operative infection[54, 88]. Therefore, lack of routine clinical use of these antibiotics argues against selection and propagation of recombinant plasmids amongst intestinal bacteria. However, such reasoning does not hold up when applied to other bacterial ecosystems where sustained drug selection of resistance markers is not expected, such as amongst soil-borne microorganisms. A surprising diversity of stable resistance genes has now been documented in soil-dwelling bacteria with no obvious environmental exposure to antimicrobials[25]. It has been suggested that plasmid maintenance functions accompanying resistance genes provide a mechanism for persistence of these and other unrelated genes in the absence of selection[91]. Indeed, such maintenance systems have been intentionally engineered into expression plasmids carried by live vectors to enhance plasmid stability in vivo in the absence of drug selection[37]. Given the inherent unpredictability of plasmid mobilization between enteric strains, and the possibility of stable propagation in the absence of selection, the prospect of unintended and unforeseen genetic events compromising critical antimicrobial therapies cannot be formally excluded. Such risk is therefore unacceptable if alternatives to antibiotic selection can be developed.

Thus, there exists a need for non-antibiotic selection systems for live vector expression plasmids.

SUMMARY OF THE INVENTION

The present invention relates generally to stabilized expression plasmid systems. The stabilized expression plasmid systems comprise an expression vector that includes a plasmid maintenance system (PMS) and, optionally, one or both of a polynucleotide encoding a selected antigen under control of a promoter, and a polynucleotide encoding a selectable marker under control of a promoter. The PMS includes (a) an origin of replication, (b) at least one post-segregational killing function, and (c) at least one partitioning function.

In one embodiment, the present invention includes an expression vector comprising a nucleotide sequence encoding:

(a) a restricted-copy-number origin of replication cassette comprising a nucleotide sequence encoding an origin of replication,
(b) at least one post-segregational killing cassette comprising a nucleotide sequence encoding at least one post-segregational killing locus,
(c) at least one partitioning cassette comprising a nucleotide sequence encoding at least one partitioning function; and
(d) at least one selectable marker cassette comprising a nucleotide sequence encoding at least one selectable marker.

In a preferred embodiment, the nucleotide sequence (a) encoding an origin of replication limits the expression vector to an average plasmid copy number of about 2 to 75 copies per cell. Further, a first unique restriction enzyme cleavage site is located 5' of the nucleotide sequence encoding the origin of replication, and a second unique restriction enzyme cleavage site is located 3' of the nucleotide sequence encoding the origin of replication.

Also in the preferred embodiment, the nucleotide sequence (b) encoding at least one post-segregational killing locus comprises a third unique restriction enzyme cleavage site located 5' of the nucleotide sequence encoding the at least one post-segregational killing locus, and a fourth unique restriction enzyme cleavage site located 3' of the nucleotide sequence encoding the at least one post-segregational killing locus.

Further in the preferred embodiment, the nucleotide sequence encoding at least one partitioning function comprises a fifth unique restriction enzyme cleavage site 5' of the nucleotide sequence encoding the at least one partitioning function, and a sixth unique restriction enzyme cleavage site located 3' of the nucleotide sequence encoding the at least one partitioning function.

Additionally in the preferred embodiment, the nucleotide sequence encoding at least one selectable marker is a nucleotide sequence encoding the *E. coli* polypeptide mchI having the amino acid sequence set forth in SEQ ID NO:30. Furthermore, a seventh unique restriction enzyme cleavage site is located 5' of the nucleotide sequence encoding the at least one selectable marker, and an eighth unique restriction enzyme cleavage site is located 3' of the nucleotide sequence encoding the at least one selectable marker, wherein the at least one selectable markers is a mchI protein In a preferred embodiment, the present invention includes an expression vector comprising a nucleotide sequence encoding:
(a) a restricted-copy-number origin of replication cassette comprising
  (i) a nucleotide sequence encoding an origin of replication that limits the expression vector to an average plasmid copy number of about 2 to 75 copies per cell,
  (ii) a first unique restriction enzyme cleavage site located 5' of the nucleotide sequence encoding the origin of replication, and
  (iii) a second unique restriction enzyme cleavage site located 3' of the nucleotide sequence encoding the origin of replication;
(b) at least one post-segregational killing cassette comprising
  (i) a nucleotide sequence encoding at least one post-segregational killing locus,
  (ii) a third unique restriction enzyme cleavage site located 5' of the nucleotide sequence encoding the at least one post-segregational killing locus, and
  (iii) a fourth unique restriction enzyme cleavage site located 3' of the nucleotide sequence encoding the at least one post-segregational killing locus;
(c) at least one partitioning cassette comprising
  (i) a nucleotide sequence encoding at least one partitioning function,
  (ii) a fifth unique restriction enzyme cleavage site 5' of the nucleotide sequence encoding the at least one partitioning function, and
  (iii) a sixth unique restriction enzyme cleavage site located 3' of the nucleotide sequence encoding the at least one partitioning function; and
(d) at least one selectable marker cassette comprising
  (i) a nucleotide sequence encoding at least one selectable marker, wherein the selectable marker is the *E. coli* polypeptide mchI having the amino acid sequence set forth in SEQ ID NO:30
  (ii) a seventh unique restriction enzyme cleavage site located 5' of the nucleotide sequence encoding the at least one selectable marker, and
  (iii) a eighth unique restriction enzyme cleavage site located 3' of the nucleotide sequence encoding the at least one selectable marker, wherein the at least one selectable markers is a mchI protein.

In preferred embodiments of the expression vectors of the present invention, the nucleotide sequence encoding an origin of replication is a nucleotide sequence selected from the group consisting of the oriE1 sequence set forth in SEQ ID NO:1, the ori101 sequence set forth in SEQ ID NO:3, and the ori15A sequence set forth in SEQ ID NO:2.

In preferred embodiments of the expression vectors of the present invention, the nucleotide sequence encoding at least one post-segregational killing locus is a nucleotide sequence selected from the group consisting of a nucleotide sequence encoding the ssb post-segregational killing locus, a nucleotide sequence encoding the asd balanced-lethal system, a nucleotide sequence encoding the phd-doc proteic system, and a nucleotide sequence encoding the hok-sok antisense system. More preferably, the nucleotide sequence encoding at least one post-segregational killing locus is a nucleotide sequence encoding the ssb post-segregational killing locus.

In preferred embodiments of the expression vectors of the present invention, the ssb post-segregational killing locus comprises a ssb inducible promoter, a ssb constitutive promoter and a ssb coding region, and the ssb post-segregational killing locus is the ssb post-segregational killing locus from *Shigella flexneri, Salmonella* Typhi or *E. coli*.

In a preferred embodiment of the expression vectors of the present invention, the ssb post-segregational killing locus comprises the ssb inducible promoter, the ssb constitutive promoter and the ssb coding region of *Shigella flexneri* 2a strain CVD 1208s as set forth in SEQ ID NO:4.

In preferred embodiments of the expression vectors of the present invention, the nucleotide sequence encoding the at least one post-segregational killing locus is a homolog of a ssb post-segregational killing locus, wherein the homolog has at least 90% identity over its entire length to the ssb post-segregational killing locus set forth in SEQ ID NO:4, wherein both the inducible and constitutive promoters of the homolog have promoter activity, and wherein the SSB polypeptide encoded by the homolog has DNA binding and DNA replication activity.

In preferred embodiments of the expression vectors of the present invention, the partitioning function is an active partitioning function.

In preferred embodiments of the expression vectors of the present invention, the nucleotide sequence encoding at least one partitioning function comprises *Escherichia coli* parA set forth in SEQ ID NO:5.

In preferred embodiments of the expression vectors of the present invention, the nucleotide sequence encoding at least one partitioning function is the par locus of *Escherichia coli* pSC101 set forth in SEQ ID NO:6.

In preferred embodiments of the expression vectors of the present invention, the average plasmid copy-number is about 5 to about 60 copies per cell.

In preferred embodiments of the expression vectors of the present invention, the expression further comprises an expression cassette comprising a nucleotide sequence encoding a promoter. The expression cassette may have a ninth unique restriction enzyme cleavage site located 5' of the nucleotide sequence encoding the promoter, and a tenth unique restriction enzyme cleavage site located 3' of the nucleotide sequence encoding the promoter. Preferably the promoter is an inducible promoter, more preferably the promoter is an ompC promoter, even more preferably the promoter is the ompC promoter set forth in SEQ ID NO:7.

In preferred embodiments of the expression vectors of the present invention where the expression vector further comprises an expression cassette, the expression cassette further comprises a nucleotide sequence encoding an antigen positioned at the 3' end of the nucleotide sequence encoding the promoter of the expression cassette, wherein expression of the antigen is under control of the promoter of the expression cassette. Preferably the antigen is a viral antigen, a bacterial antigen, a cancer antigen, or an auto-immune antigen. More preferably, the antigen is a domain of the anthrax toxin Protective Antigen PA83 moiety, full-length PA83 or the 63 kDa biologically active form of PA83. Even more preferably, the antigen is domain 4 of the anthrax toxin Protective Antigen PA83 set forth in SEQ ID NO: 36.

In other preferred embodiments the antigen may be one or more fragments of a *Clostridium botulinum* neurotoxin eukaryotic cell-binding heavy chain, wherein the heavy chain is a heavy chain of a *Clostridium botulinum* serotype selected from the group consisting of *Clostridium botulinum* serotypes A, B, C, D, E, F and G.

The present invention further includes a cell comprising one or more of the expression vectors described herein. Preferably, the cell is an isolated cell, and is a bacterial cell. Preferably the bacterial cell is a *Salmonella Typhi* cell or a cell of a bacterial strain selected from the group consisting of *Shigella flexneri* 2a strain CVD 1208s, *Salmonella enterica* serovar Typhi strain CVD 908-htrA, *Salmonella enterica* serovar Typhi strain CVD 909, and *E. coli* strain DH5 alpha.

In preferred embodiments, the endogenous ssb gene of the cell comprising one or more of the expression vectors of the present invention is inactivated or deleted. Preferably, the cell is a bacterial cell where the endogenous ssb gene is inactivated or deleted. More preferably, the cell is a *Salmonella Typhi* cell where the endogenous ssb gene is inactivated or deleted. Even more preferably, the cell is *Salmonella enterica* serovar Typhi strain CVD 908-htrAssb.

DETAILED DESCRIPTION OF THE INVENTION

Figure 1:
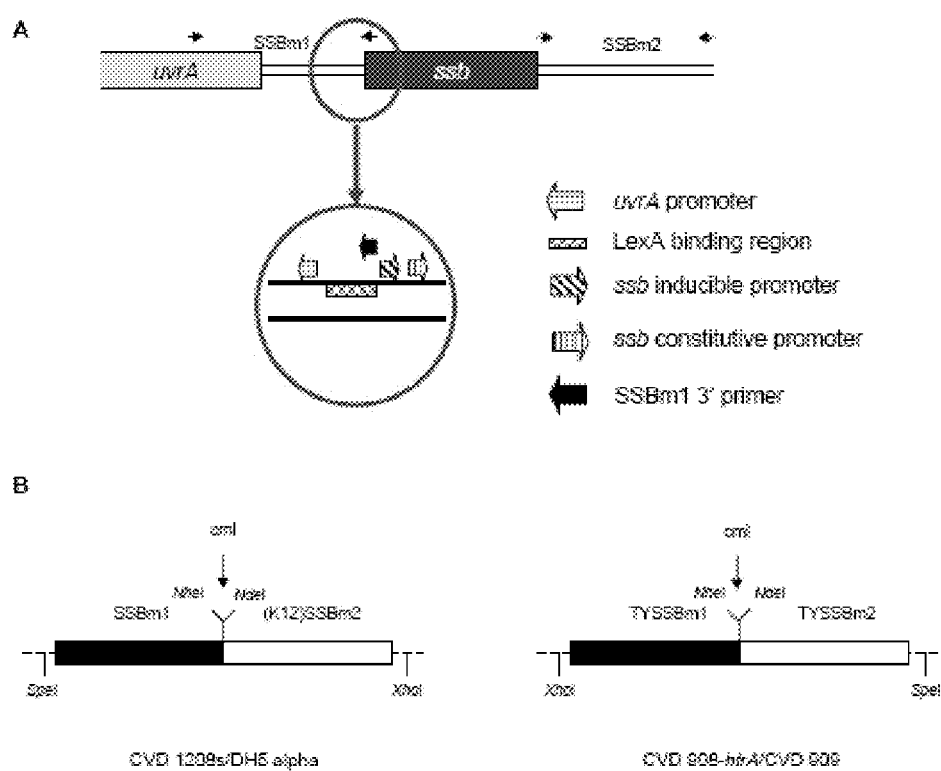
FIG. 1A: diagrammatic representation of the uvrA and ssb genes and control regions.
FIG. 1B: ligated products from amplification of control and coding regions of ssb gene.
Figure 2:
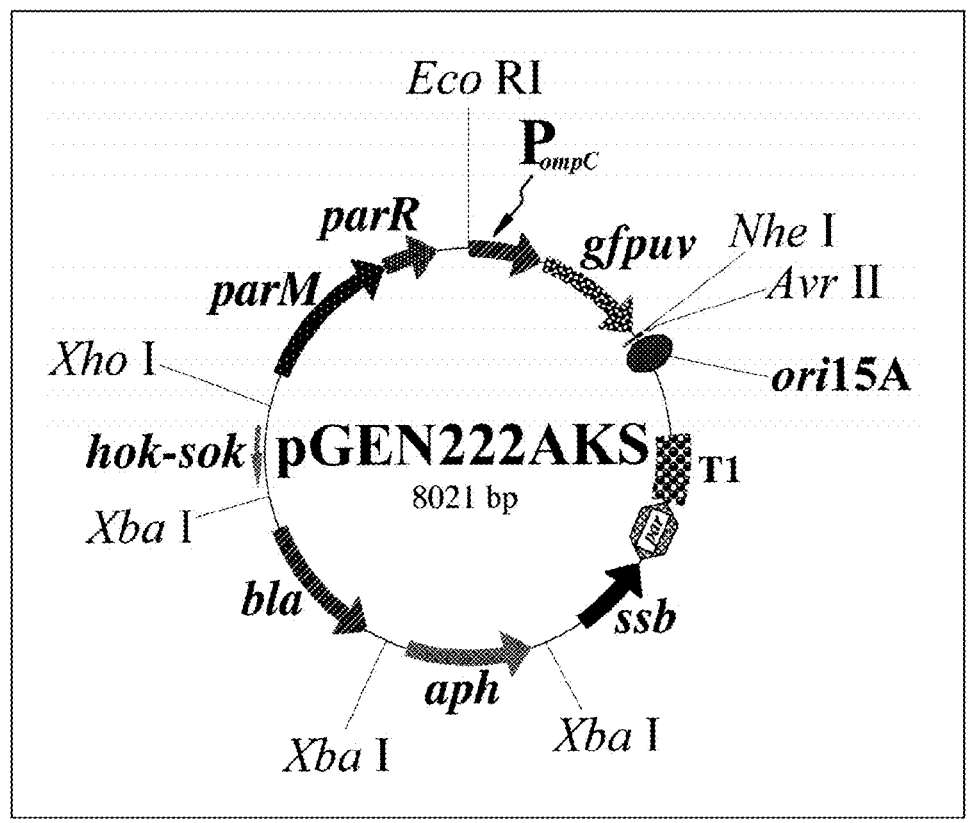
FIG. 2: genetic map of pGEN222AKS

The present invention relates generally to stabilized expression plasmid systems. The stabilized expression plasmid systems comprise an expression vector that includes a plasmid maintenance system (PMS) which serves to optimize the maintenance of the expression vector in bacteria at two independent levels by: (1) removing dependence on balanced lethal maintenance systems that utilize enzymes with catalytic activity; and (2) incorporating a plasmid partition system to prevent random segregation of expression vectors, thereby enhancing inheritance and stability of the plasmids.

Embodiments of the stabilized expression plasmid systems of the present invention include expression vectors comprising a polynucleotide encoding a selected antigen under control of a promoter, in addition to the PMS.

In another embodiment, the expression vector comprises a polynucleotide encoding a selectable marker, such as a temperature sensitive marker, a drug resistance marker or an antimicrobial peptide, in addition to the PMS. In an equally preferred embodiment, the expression vector comprises both (i) a polynucleotide encoding a selected antigen under control of a promoter and (ii) a polynucleotide encoding a selectable marker, in addition to the PMS.

The PMS includes (a) an origin of replication, (b) at least one post-segregational killing function, and (c) at least one partitioning function.

The present invention also generally relates to bacterial live vector vaccines, comprising bacteria transfected with a stabilized expression plasmid system of the present invention, and methods of making and using bacterial live vector vaccines. The bacterial live vector vaccines of the present invention can be used to induce an immune response to the bacteria itself, or to induce an immune response to the selected antigen expressed by the bacteria, or both.

A. Stabilized Expression Plasmid System

The stabilized expression plasmid systems of the present invention are based on expression vectors genetically engineered to comprise a PMS, and optionally a polynucleotide encoding a selected antigen under control of a promoter, or a polynucleotide encoding a selectable marker, or both.

The PMS includes (a) an origin of replication, (b) at least one post-segregational killing function, and (c) at least one partitioning function.

1. Origin of Replication

The PMS includes a restricted-copy-number origin of replication that limits the expression vector to a range of plasmid copies per cell. Due to varying degrees of toxicity associated with different selected antigens (e.g., higher toxicity for antigens derived from parasitic organisms such *Plasmodium fal-*

*ciparum* versus virtually no toxicity for the fragment C of tetanus toxin), the stabilized expression plasmid system of the present invention is based on either a low or medium copy number expression vector (plasmid). It will be appreciated by one skilled in the art that the selection of an origin of replication will depend on the degree of toxicity, i.e., the copy number should go down as toxicity to the bacterial strain goes up.

The origins of replication of the present invention includes both naturally-occurring origins of replication, as well as origins of replication encoded by nucleotide sequences which are substantially homologous to nucleotide sequences encoding naturally-occurring origins of replication, and which retain the function and activity exhibited by the naturally-occurring origins of replication.

It is preferable for the origin of replication to confer an average copy number which is between about 2 and about 75 copies per cell, between about 5 and about 60 copies per cell, between about 5 to about 30 copies per cell, or between about 5 to about 15 copies per cell. Preferred origins of replication include those of *E. coli* plasmid pAT153 (oriE1, ~60 copies per chromosomal equivalent), the *E. coli* plasmid pACYC184 (ori15A, ~15 copies per chromosomal equivalent), and the *Salmonella* Typhimurium plasmid pSC101 (ori101, ~5 copies per chromosomal equivalent). Substantial homologs of oriE1, ori15A and ori101 having the same function and activity as the unaltered origins of replication may also be used.

In preferred embodiments, the nucleotide sequence encoding the origin of replication is a nucleotide sequence selected from the group consisting of the oriE1 sequence of SEQ ID NO:1, the ori101 sequence of SEQ ID NO:3, and the ori15A sequence of SEQ ID NO:2. Substantial homologs of the origins of replication of SEQ ID NOs:1-3, having the same function and activity as the origins of replication of SEQ ID NOs:1-3, may also be used.

In a further preferred embodiment, the origin of replication is the oriE1 locus from pSC101, conferring a copy number of approximately 5 copies per genome equivalent, set forth in SEQ ID NO:1.

2. Partitioning Function

The PMS also includes a partitioning function, also known in the art and herein as a "segregating system" and a "partitioning system." The partitioning function is any plasmid stability-enhancing function that operates to increase the frequency of successful delivery of a plasmid to each newly divided bacterial cell, as compared to the frequency of delivery of a corresponding plasmid without such a function. Partitioning systems include, for example, equi-partitioning systems, pair-site partitioning systems, and the systems provided in Table 1 of Chapter 5, Partition Systems of Bacterial Plasmids. B. E. Funnell and R. A. Slavcev. In Plasmid Biology. 2004. B E Funnell and G J Phillips, eds. ASM Press, Washington, D.C.

The partitioning systems of the present invention includes both naturally-occurring partitioning systems, as well as partitioning systems encoded by nucleotide sequences which are substantially homologous to nucleotide sequences encoding naturally-occurring partitioning systems, and which retain the function and activity exhibited by the naturally-occurring partitioning systems.

Exemplary partitioning functions include, without limitation, those provided by systems of pSC101, the F factor, the P1 prophage, and IncFII drug resistance plasmids.

In particular, the par passive partitioning locus can be used. The function of the par locus appears to be related to increasing plasmid supercoiling at the origin of replication, which is also the binding site for DNA gyrase. An exemplary par sequence is that of *E. coli*, set forth in SEQ ID NO:6 (Miller et al., Nucleotide sequence of the partition locus of *Escherichia coli* plasmid pSC101, *Gene* 24:309-15 (1983); GenBank accession no. X01654, nucleotides 4524-4890)).

The active partitioning parA locus may also be used. An exemplary parA locus sequence is set forth in SEQ ID NO:5. Substantial homologs of the partitioning loci of SEQ ID NOs:5 and 6, having the same function and activity as the partitioning loci of SEQ ID NOs:5 and 6, may also be used.

3. Post-Segregational Killing Function

The PMS further includes at least one post-segregational killing (PSK) function. The PSK function is a function which results in the death of any newly divided bacterial cell which does not inherit the plasmid of interest, and specifically includes balanced-lethal systems such as asd or ssb, proteic systems such as phd-doc, antisense systems such as hok-sok, and polynucleotides encoding antimicrobial peptides such as colicins and microcins.

The PSK function of the present invention includes both naturally-occurring PSK functions, as well as PSK functions encoded by nucleotide sequences which are substantially homologous to nucleotide sequences encoding naturally-occurring PSK functions, and which retain the function and activity exhibited by the naturally-occurring PSK functions.

In preferred embodiments, the PSK function is the ssb balanced lethal system. The single-stranded binding protein (SSB) from *Salmonella* Typhi is used to trans-complement an otherwise lethal mutation introduced into the chromosomal ssb gene. The biochemistry and metabolic roles of the *E. coli* SSB protein have been extensively reviewed in Lohman et al., *Annual Reviews in Biochemistry* 63:527, 1994 and Chase et al., *Annual Reviews in Biochemistry* 55:103, 1986 (the disclosures of which are incorporated herein by reference) and are briefly summarized here.

SSB is a non-catalytic 177 amino acid protein, with a relative molecular weight of 19 kDa, that binds with high affinity to single-stranded DNA (ssDNA), and plays an essential role as an accessory protein in DNA replication, recombination, and repair. The biologically relevant form of SSB involved in binding to ssDNA is a tetramer. Spontaneously occurring temperature-sensitive point mutations within ssb, affecting stable tetramer formation, have been characterized at the biochemical, physiological, and nucleotide level. One such mutant, ssb-1, contains the point mutation His 55 to Tyr, and is unable to assemble correctly into tetramers at non-permissive temperatures[110]. ssb-1 mutant strains exhibit temperature-sensitive lethal defects in DNA replication and recombination. Interestingly, over-expression of the SSB-1 mutant protein from the plasmid pACYC184 has been shown to remove the temperature-sensitive conditional lethality of chromosomal ssb-1[17], presumably through the formation of the required tetramers at higher protein concentrations[110]. In addition, it was reported by Carlini et al.[14] that the temperature-sensitive phenotype of a tryptophan 54-to-serine substitution (i.e., adjacent to the His 55 mutation in ssb-1) was again suppressed when $ssb^{W54S}$ was present on high copy number pUC plasmids.

The stability of plasmids carrying ssb to complement chromosomal ssb mutations in *E. coli* bacteria was examined by Porter et al.[79]. They observed that in experiments involving bioreactors, the frequency of plasmid loss in strains grown in continuous culture under non-selective conditions for over 6 days was less than $1\times10^{-7}$; this frequency was independent of copy number, as both lower copy number pACYC184 plasmids and very high copy number pUC19 plasmids were both maintained efficiently.

In the bacterial strains used as bacterial live vector vaccines of the present invention, comprising a stabilized expression plasmid system wherein the PSK function is the ssb balanced lethal system, the native ssb locus of the bacteria is inactivated. The native ssb locus may be inactivated by any means known in the art, such as a suicide vector comprising a temperature sensitive origin of replication or Lambda Red-mediated mutagenesis (Datsenko and Wanner, *PNAS USA* 97:6640-6645 (2000)). In a preferred aspect, Lambda Red-mediated mutagenesis is used to inactivate the ssb locus of the bacterial strain used as the bacterial live vector vaccine of the present invention.

In another aspect of the invention, the PSK function is the ssb locus where both the inducible and the constitutive ssb gene promoters are used as the promoters of the ssb PSK function. In a preferred embodiment, the PSK function comprises a ssb inducible promoter, a ssb constitutive promoter and a ssb coding region. Preferably, the ssb locus is the ssb locus of any one of *Shigella flexneri*, *Salmonella* Typhi and *E. coli*. In one embodiment the ssb locus is the ssb locus of *S. flexneri* 2a strain CVD 1208s set forth in SEQ ID NO:4. A substantial homolog of the ssb locus of SEQ ID NO:4, having the same function and activity as the ssb locus of SEQ ID NO:4, may also be used.

In a related aspect of the invention, mutated alleles such as ssb-1 (or any mutation functionally equivalent to this allele, such as W54S; Carlini et al. *Mol. Microbiol.* 10:1067-1075 (1993)) may be incorporated into the stabilized expression plasmid system to enhance higher copy number plasmids by over-expression of SSB1-like proteins to form the required biologically active tetramers of SSB.

In a further embodiment, the PMS comprises two PSK functions.

4. Selected Antigen

The stabilized expression plasmid system may also comprise a polynucleotide encoding selected antigen under control of a promoter.

a. Promoter

The promoter is preferably an environmentally regulatable promoter, controlled by a biologically relevant signal such as osmolarity. In a preferred embodiment, the promoter is the ompC promoter. The ompC gene encodes a porin protein which inserts as a trimer into the outer membrane of a bacterial cell. Expression and control of ompC has been reviewed in considerable detail in Pratt et al., *Molecular Microbiology* 20:911, 1996 and Egger et al., Genes to Cells 2:167, 1997. In a preferred embodiment the ompC promoter fragment from *E. coli* is used, set forth in SEQ ID NO:7. See U.S. Pat. No. 6,703,233, which is incorporated herein by reference in its entirety. Transcription of a selected antigen under control of a promoter may be terminated in the 3'-distal region by a trpA transcriptional terminator. A substantial homolog of the ompC promoter of SEQ ID NO:7, having the same function and activity as the ompC promoter of SEQ ID NO:7, may also be used.

In one aspect, the inducible promoter is the mutated $P_{ompC1}$, or the $P_{ompC3}$ promoter. The promoter may be used to exclusively control the transcription of the downstream selected antigen.

In another aspect, the ompC promoter may be the ompC promoter from pAT153 (~60 copies per chromosomal equivalent), pACYC184 (~15 copies), or pSC101 (~5 copies).

b. Selected Antigen

The selected antigen may be any antigen which does not kill the bacterial live vector vaccine expressing it, and which elicits an immune response when the bacterial live vector vaccine expressing the antigen is administered to the subject.

In certain embodiments, the selected antigen is permitted to harm or inhibit the bacterial host of the bacterial live vector vaccine. The selected antigen may be homologous (from bacteria used as the bacterial live vector vaccine) or heterologous.

Non-limiting examples of the selected antigen include: Shiga toxin 1 (Stx1) antigen, Shiga toxin 2 (Stx2) antigen, and proteins of hepatitis B, *Haemophilus influenzae* type b, hepatitis A, acellular pertussis ($_{ac}$P), varicella, rotavirus, *Streptococcus pneumoniae* (pneumococcal), and *Neisseria meningitidis* (meningococcal). See Ellis et al., *Advances in Pharm.*, 39: 393-423, 1997 (incorporated herein by reference). Where the antigen is a Shiga toxin 2 antigen, the Shiga toxin 2 antigen can, for example, be either a B subunit pentamer or a genetically detoxified Stx 2. Further antigens of relevance to biodefense and included herewith for use as the selected antigen include: 1) one or more domains of the anthrax toxin (*Bacillus anthracis*) Protective Antigen PA83 moiety, including but not limited to domain 4 (the eukaryotic cell-binding domain; D4), the processed 63 kDa biologically active form of PA83, or full-length PA83; and 2) *Clostridium botulinum* antigens comprising the eukaryotic cell-binding heavy chain fragment of any neurotoxin serotype A, B, C, D, E, F, or G, in any combination. Other selected antigens include each of those disclosed in U.S. Pat. No. 6,190,669, incorporated herein by reference.

In a preferred embodiment, the selected antigen is domain 4 of the anthrax toxin Protective Antigen PA83 set forth in SEQ ID NO:36. Preferably, the polynucleotide sequence encoding domain 4 is set fort in SEQ ID NO:35.

Further in regard to anthrax toxin, it is noted that anthrax toxin is a primary virulence determinant responsible, in part, for the clinical effects of infection with *Bacillus anthracis*. Anthrax toxin is comprised of two catalytic protein domains, lethal factor (LF) and edema factor (EF), which competitively bind to three equivalent binding sites atop a heptameric ring of 63 kDa cell-binding protective antigen (PA63) monomers, the biologically processed and active form of the full-length precursor PA83 anthrax toxin subunit[22]. Aggregate in vitro results using tissue culture monolayers and purified toxin components suggest that upon intoxication of a target cell, PA63 undergoes an acid-induced conformational change which results in translocation of the LF catalytic domain into the cell cytoplasm, followed either by rapid cell death or cytokine release at sub-lethal levels of intoxication[23]. Crystallographic analysis of full-length PA83 has revealed a four domain structure in which the eukaryotic cell-binding domain resides within the carboxyl terminus of the protein (D4; residues 596-735)[105]. Genetic deletion of D4 from the chromosomal locus encoding PA83, within an otherwise fully virulent *B. anthracis* strain, resulted in a 4 log increase in the $LD_{50}$ of the resulting strain. Since mice immunized with spores from this attenuated strain were only partially protected in a spore challenge with 40 $LD_{50}$ of the fully virulent encapsulated parent, it was hypothesized that D4 contains immunodominant epitopes required to induce a strong protective humoral immune response against anthrax toxin[12].

In one aspect, the selected antigen is an antigen that induces an immune response to cancer. In another aspect, the selected antigen is designed to provoke an immune response to autoantigens, B cell receptors and/or T cell receptors which are implicated in autoimmune or immunological diseases. For example, where inappropriate immune responses are raised against body tissues or environmental antigens, the immunizing compositions of the present invention may be used to induce an immune response to the autoantigens, B cell receptors and/or T cell receptors to modulate the responses and ameliorate the diseases. For example, such techniques can be efficacious in treating myasthenia gravis, lupus erythematosis, rheumatoid arthritis, multiple sclerosis, allergies and asthma.

c. Extracellular Antigen Export System

In addition to, or in place of, a polynucleotide encoding a selected antigen under control of a promoter, the expression vector of the stabilized expression plasmid system of the present invention may include a polynucleotide encoding a selected antigen in the context of an extracellular antigen export system.

The extracellular antigen export system is derived from a cryptic hemolysin encoded by clyA within the chromosome of *Salmonella* Typhi CVD 908-htrA[35]. Cytolysin A (ClyA) from *Salmonella* Typhi was first described by Wallace et al.[107] who also reported the crystal structure for the homologous HlyE hemolysin from *E. coli*. HlyE is a kinked rod-shaped 35 kDa molecule with a hydrophobic 27-residue transmembrane region comprising one terminus of the folded molecule. HlyE is exported into the surrounding medium, and assembles into a 13-meric pore upon contact with target eukaryotic membranes, ultimately leading to cell lysis[30]. Wai et al.[106] showed that ClyA is not secreted by any of the known secretion pathways, but is instead exported via outer membrane vesicles. Such a mechanism for vesicle formation raised the intriguing possibility of engineering ClyA to export heterologous domains from live vectors that are otherwise potentially toxic when expressed cytoplasmically; these vesicles may also carry immunomodulatory lipopolysaccharide (LPS) to improve the immunogenicity of a foreign antigen.

The promoter used in conjunction with a polynucleotide encoding a selected antigen in the context of an extracellular antigen export system may be any of the promoters described herein or other suitable promoters known in the art. Preferred promoters include a variant of the lac UV5 promoter from the plasmid pML33C, designated herein as $P_{33C}$, as described by Kobayashi et al., *Nucleic Acids Res.* 18:7367-7372 (1990). A further preferred promoter is the ompC promoter fragment from *E. coli* set forth in SEQ ID NO:7.

A polynucleotide encoding a fusion protein comprising ClyA and a selected antigen, under control of a promoter, may be used The expression vector of the stabilized expression plasmid system of the present invention may thus include a polynucleotide encoding a fusion protein comprising full-length ClyA and a selected antigen, under control of a promoter, as an extracellular antigen export system. The polynucleotide sequence encoding clyA of CVD 908-htrA is set forth in SEQ ID NO:27.

In one embodiment, a ClyA-D4 protein fusion may be engineered wherein a synthetic gene (d4) encoding protective antigen domain 4 is genetically fused in-frame to the carboxyl terminus of clyA (clyA::d4)[35], and used as an extracellular antigen export system to be included in the expression vector of the stabilized expression plasmid system of the present invention. The sequence of clyA::d4 is shown in SEQ ID NO:28. In a preferred embodiment, clyA:: d4 is under control of ompC promoter.

5. Selectable Marker

In another aspect of the present invention, the stabilized expression plasmid system may also comprise a polynucleotide encoding a selectable marker, such as a temperature sensitive marker, drug resistance marker or an antimicrobial polypeptide.

While selectable markers can be used to help maintain stabilized expression plasmid systems in vitro in the bacterial live vector vaccines, selectable markers are primarily used for in vitro passage and maintenance of vectors in bacteria during construction of such vectors for use in stabilized expression plasmid systems. Drug resistance markers are well-known for such purposes. A non-limiting example of a drug resistance marker includes aph which is known in the art to confer resistance to aminoglycosides kanamycin and/or neomycin. Other resistance markers available for routine selection of plasmids include bla, tet and cam, encoding resistance to ampicillin/carbenicillin, tetracycline, and chloramphenicol, respectively.

Antimicrobial polypeptides are an alternative to the use of drug resistance markers, allowing conventional, drug-based antibiotic-free maintenance of vectors in bacteria during vector construction, and in animal hosts after administration of bacterial live vector vaccines. These polypeptides are synthesized by a wide variety of mammals, amphibians, insects, plants, and bacteria[63, 68]. Antimicrobial peptides synthesized by both Gram-positive and Gram-negative bacteria are called bacteriocins, which are further classified either as colicins (often larger than 20 kDa) or microcins (typically less than 10 kDa). While the antimicrobial activity of colicins is generally genus-specific for *Escherichia*, microcins have a broader spectrum of activity against Enterobacteriaceae including *Escherichia, Salmonella, Shigella, Citrobacter, Klebsiella* and *Enterobacter*[68]. The 10 known microcins (Mcc) can be further grouped into post-translationally modified peptides (including MccB17, C7, D93, and J25)[28] and unmodified peptides (such as MccV, E492, McCH47, L, M, and 24)[69, 78]. Patzer et al.[69] recently reported that McCH47 inhibited the growth of *Salmonella Typhimurium* strain LT2. McCH47 has been confirmed to inhibit the growth of CVD 908-htrA and McCH47 has been demonstrated to function as a selectable marker.

Synthesis of McCH47 is encoded within a ~10.5 kb mch47 operon (GenBank accession number AJ009631; Dec. 19, 2005 report)[77] that was recovered from a human *E. coli* fecal strain. The operon also encodes an ATP-binding cassette (ABC) export system specific for McCH47[4]. A catecholate siderophore production system is proposed to enhance McCH47 uptake by target bacteria[3, 77], and an immunity protein is required for bacterial self-immunity[33, 82]. McCH47, encoded by mchB, is a bactericidal peptide synthesized as a 75 residue precursor that is processed during secretion to a 60 residue 4.9 kDa mature extracellular peptide[81]. The extracellular target of McCH47 is the proton channel of the $F_0F_1$ ATP synthase complex[83, 102] necessary for generating the critical proton-motive force required for transport of nutrients across bacterial plasma membranes. Immunity to this peptide is conferred by a 69 amino acid highly hydrophobic protein encoded by mchI (SEQ ID NO:29). The mchI protein (SEQ ID NO:30) is anchored within the cytoplasmic membrane by two transmembrane regions[82], and binds to McCH47 to prevent cell death.

The promoter used in conjunction with a polynucleotide encoding a selectable marker may be any of the promoters described herein or other suitable promoters known in the art. Preferred promoters include a variant of the lac UV5 promoter from the plasmid pML33C, as described by Kobayashi et al., *Nucleic Acids Res.* 18:7367-7372 (1990), designated here as $P_{33C}$. A further preferred promoter is the ompC promoter fragment from *E. coli* set forth in SEQ ID NO:7.

In one embodiment of the present invention, the mchI protein is a selectable marker and stabilized expression plasmid systems containing mchI can be selected for on solid medium containing microcin H47 after introduction into bacteria, such as CVD 908-htrA. In a preferred embodiment, the mchI polynucleotide (SEQ ID NO:29) is used as the selectable marker, under control of the $P_{33C}$ promoter. Other examples of selection systems based on ribosomally synthesized antimicrobial peptides could, in theory, be based upon the use of any such peptides demonstrating antibacterial activity against *Salmonella* species, including but not limited to microcin 24 (Patzer et al. 2003. Microbiology. 149: 2557-2570), microcin J25 (Vincent et al. 2004. FEMS Micro. 236: 103-107.), microcin L (Pons et al. 2004. Antimicrob. Agents Chemother. 48: 505-513.), and colicin 24 (O'Brien and Mahanty. 1994. Plasmid. 31: 288-296).

The present invention also encompasses a PMS wherein mchI is used as the PSK function.

6. Cassettes

Each of the noted elements of the expression vectors of the stabilized expression plasmid systems of the present invention may be present in the expression vector as individual cassettes. Each of the cassettes may comprise unique restriction enzyme cleavage sites located at the 5' and 3' ends of the cassettes to facilitate construction of the expression vector.

Preferably, each of the origins of replication present within the expression vectors of the stabilized expression plasmid systems of the present invention are transcriptionally sequestered to block interference from transcription originating from any other cassette, and avoid fluctuations of intended copy number. One, some or all of the origins may be flanked at one end by the highly efficient T1 terminator from the *E. coli* rrnB ribosomal RNA operon; the distal terminus of the origin may be separated from encoded polypeptide by a trpA terminator.

7. Homologs

The term "substantially homologous" or "substantial homolog," in reference to a nucleotide sequence or amino acid sequence herein, indicates that the nucleic acid sequence or amino acid sequence has sufficient homology as compared to a reference sequence (e.g., a native or naturally-occurring sequence) to permit the sequence to perform the same basic function and have equivalent activity as the corresponding reference sequence. A substantially homologous sequence typically has at least about 70% sequence identity as compared to the reference sequence, typically at least about 85% sequence identity, preferably at least about 90 or 95% sequence identity, and most preferably about 96, 97, 98 or 99% sequence identity, as compared to the reference sequence. It will be appreciated that throughout the specification, where reference is made to specific nucleotide sequences and/or amino acid sequences, that such nucleotide sequences and/or amino acid sequences may be replaced by substantially homologous sequences.

8. Expression Vectors

While specific expression vectors for use in the stabilized expression plasmid systems of the present invention are described herein, any expression vector minimally comprised of (i) an origin of replication functional within *Salmonella* Typhi and (ii) a selectable marker may be used as a template from which the expression vectors for use in the stabilized expression plasmid systems of the present invention are constructed. In a preferred embodiment, expression vectors described herein are engineered as a set of independently functioning cassettes assembled in such a way as to permit replacement of a given module as required for a given application. For example, implementation of the selection system based on use of microcin H47 would ultimately require replacement of current drug resistance marker such as aph with the mchI allele, without influencing proper expression or function of any other gene cassettes within the expression plasmid.

B. Bacteria

As noted above, the present invention also generally relates to bacterial live vector vaccines, comprising bacteria transfected with a stabilized expression plasmid system of the present invention. Suitable bacteria are those into which the stabilized expression plasmid system may be introduced, that can propagate while maintaining the stabilized expression plasmid system in successive generations, and that express the selected antigen when such an antigen is included within the stabilized expression plasmid system.

Suitable bacteria for use as bacterial live vector vaccines include enteric pathogens (e.g., *Salmonella enterica, Salmonella* Typhi, *Salmonella* Paratyphi A, *Salmonella* Paratyphi B, *Shigella* sp., *Vibrio cholerae*), commensals (e.g., *Lactobacillus* sp., *Streptococcus gordonii*) and licensed vaccine strains (e.g., BCG). Specific examples of suitable bacteria include, but are not limited to, *Salmonella* Typhi strains CVD908 and CVD 909, as well as the *Shigella flexneri* 2a strain CVD 1208s, and the *E. coli* strain DH5 alpha.

1. Attenuated Bacteria

In a preferred embodiment, the bacterial used in the production of the bacterial live vector vaccines are attenuated strains of bacteria. Such attenuated strains may be used to induce an immune response in a subject without causing disease in the subject.

As used herein, attenuated bacterial strains are those that have a reduced, decreased, or suppressed ability to cause disease in a subject, or those completely lacking in the ability to cause disease in a subject. Attenuated strains may exhibit reduced or no expression of one or more genes, may express one or more proteins with reduced or no activity, may exhibit a reduced ability to grow and divide, or a combination of two or more of these characteristics. The attenuated strains of the present invention may be living or dead.

Suitable attenuated bacterial strains include attenuated strains of enteric pathogens (e.g., *Salmonella enterica, Salmonella* Typhi, *Salmonella* Paratyphi A, *Salmonella* Paratyphi B, *Shigella* sp., *Vibrio cholerae*), commensals (e.g., *Lactobacillus* sp., *Streptococcus gordonii*) and licensed vaccine strains (e.g., BCG). Specific examples of suitable bacteria that may be attenuated include, but are not limited to, *Salmonella* Typhi strains CVD908, CVD 908-htrA, and CVD 909, as well as the *Shigella flexneri* 2a strain CVD 1208s, and the *E. coli* strain DH5 alpha.

The attenuated bacterial strains may be attenuated though the mutation of one or more loci and/or genes within the bacteria. The attenuating mutations may be any mutation, such as one or more nucleic acid deletions, insertions or substitutions. The mutations may be any nucleic acid deletion, insertion or substitution of a loci or gene that results in a reduction or absence of expression from the loci or gene, or a reduction or absence of activity of a polypeptide encoded by a loci or gene. The mutations may be in the coding or non-coding regions of the loci or gene.

When a *Salmonella* spp. is used as the bacteria in the bacterial live vector vaccines of the present invention, the *Salmonella* spp. may be attenuated through mutation in a number of different genes. While an extensive discussion of attenuating mutations of *Salmonella* spp. is provide in U.S. Pat. No. 6,682,729, exemplary genes include those encoding various biochemical pathways, global regulatory systems, heat shock proteins, other regulatory genes, and putative virulence properties. Specific examples of such attenuating mutations include, but are not limited to: (i) auxotrophic and related mutations affecting metabolism, such as guaA, guaB, guaBA loci, aro (aroC, aroD), gua, nad, thy, clpX, clpP, and asd mutations; (ii) mutations that inactivate global regulatory functions, such as cya, crp, phoP/phoQ, phoP$^c$ and ompR mutations; (iii) mutations that modify the stress response, such as recA, htrA, htpR, hsp and groEL mutations; (iv) mutations in specific virulence factors, such as pag and prg (v) mutations that affect DNA topology, such as topA mutations; (vi) mutations that block biogenesis of surface polysaccharides, such as rfb, galE and via mutations; (vii) mutations that modify suicide systems, such as sacB, nuc, hok, gef, kil, and phlA mutations; (viii) mutations that introduce suicide systems, such as lysogens encoded by P22, λ murein transglycosylase and S-gene; and (ix) mutations that disrupt or modify the correct cell cycle, such as minB mutations. The skilled artisan will understand that one or more of these mutations can also be made in species other than *Salmonella* spp. as most of the noted genes are common to numerous genera of bacteria.

Deletions can be made in any of the loci or genes included herein by using convenient restriction sites located within the loci or genes, or by site-directed mutagenesis with oligonucleotides (Sambrook et al, In: Molecular Cloning, A Laboratory Manual, Eds., Cold Spring Harbor Publications (1989)).

Inactivation of the loci or genes can also be carried out by an insertion of foreign DNA using any convenient restriction site, or by site-directed mutagenesis with oligonucleotides (Sambrook et al, supra) so as to interrupt the correct transcription of the loci or genes. The typical size of an insertion that can inactivate the loci or genes is from 1 base pair to 100 kbp, although insertions smaller than 100 kbp are preferable. The insertion can be made anywhere inside the loci or gene coding regions or between the coding regions and the promoters.

Other methods for the inactivation of the loci and genes include the transfer into the selected bacterial strain of mutated versions of native loci or genes, transposon-generated deletions, and imprecise excision of DNA insertions.

Preferably, the bacterial loci and genes are mutated using Lambda Red-mediated mutagenesis (Datsenko and Wanner, *PNAS USA* 97:6640-6645 (2000)). Briefly, in step 1 host bacteria targeted for mutation are transformed with a temperature sensitive plasmid encoding λ Red recombinase. These bacteria are grown in the presence of arabinose to induce λ Red production. Chromosomal mutagenesis of a target sequence is accomplished by electroporation of the host with linear DNA in which the target gene is replaced with an antibiotic resistance marker. This DNA also encodes short regions of flanking chromosomal sequences to allow for chromosomal integration of the resistance marker by λ Red-mediated homologous recombination. Recombinants are selected for on solid media containing the appropriate antibiotic, and incubated at a temperature facilitating the loss of the plasmid encoding λ Red recombinase. For step 2, removal of the chromosomal resistance marker is facilitated by transforming the bacteria with a temperature sensitive plasmid encoding FLP recombinase, which targets unique sequences within the antibiotic resistance marker now present in the host chromosome. Transformants are grown at temperatures permissive for the presence of the FLP recombinase which is expressed constitutively. Mutants are screened via PCR, grown at a temperature to facilitate loss of the plasmid encoding FLP recombinase, and selected for storage.

In a preferred embodiment, *Salmonella* Typhi CVD 908-htrA is used as the bacterial strain in the bacterial live vector vaccine of the present invention. *Salmonella* Typhi CVD 908-htrA is an attenuated strain of *Salmonella* Typhi where the htrA gene, encoding a stress-induced serine protease responsible for degradation of mis-folded periplasmic proteins[67], is inactivated. htrA mutants in *Salmonella Typhimurium* were shown to be less virulent in mice[19], and were shown in vitro to be less able to withstand the oxidative burst following phagocytosis into macrophages[7]. The resulting vaccine strain CVD 908-htrA was found to be well tolerated at doses up to 5×10$^9$ with no positive blood cultures detected. In addition, CVD 908-htrA elicited a broad immune response to *Salmonella* Typhi antigens that included intestinal secretory IgA antibodies, serum IgG antibodies, and cellular immune responses[85, 98, 99]. The ability of CVD 908-htrA to successfully deliver foreign antigens to the human immune system was demonstrated by Tacket et al[95]. In this study, volunteers were orally immunized with 10$^9$ cfu of the CVD 908-htrA(pTETlpp) live vector constitutively expressing fragment C of tetanus toxin within the cytoplasm. One of three volunteers, who were initially seronegative for tetanus antitoxin, developed a significant rise in serum neutralizing antibodies after vaccination.

Having now successfully completed both Phase I and Phase II clinical trials, CVD 908-htrA is considered a safe and highly immunogenic oral vaccine against typhoid fever, and expected to be an excellent candidate as a live vector for delivering heterologous antigens[99].

2. Introduction of the Stabilized Expression Plasmid System into Bacteria

The stabilized expression plasmid systems of the present invention may be introduced into bacterial using any of the conventional methods know in the art. Preferably, the stabilized expression plasmid systems are introduced into bacteria either by chemical transformation (for routine laboratory strains of bacteria derived from human commensal bacteria such as *E. coli*) or by electroporation.(for both common laboratory strains and strains used exclusively with attenuated vaccine candidates derived from *Salmonella* Typhi and *Shigella flexneri* 2a.

C. Methods of Inducing an Immune Response

The present invention also includes methods of inducing an immune response in a subject. The immune response may be to the bacterial strain used as the bacterial live vector vaccine itself, a selected antigen expressed by the bacterial live vector vaccine, or both.

In one embodiment, the method of inducing an immune response comprises administering one or more of the bacterial live vector vaccines of the present invention to a subject in an amount sufficient to induce an immune response in the subject (an immunologically-effective amount).

In a further embodiment, the method of inducing an immune response comprises administering a pharmaceutical formulation comprising one or more of the bacterial live vector vaccines of the present invention to a subject in an immunologically-effective amount.

For the sake of convenience, the bacterial live vector vaccines of the present invention and pharmaceutical formulations comprising the bacterial live vector vaccines are referred to herein as "immunizing compositions." The skilled artisan will appreciate that the immunizing compositions are synonymous with vaccines.

As used herein, an "immune response" is the physiological response of the subject's immune system to the immunizing composition. An immune response may include an innate immune response, an adaptive immune response, or both.

In a preferred embodiment of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

The subject to which the immunizing compositions may be administered is preferably a human, but may also be another mammal such as a simian, dog, cat, horse, cow or pig, or a bird, such as a chicken.

In one embodiment, the subject is a subject at risk for developing an infection to a particular bacteria. In another embodiment, the subject is immunologically naïve or, alternatively, exhibits pre-existing immunity to the particular bacteria.

D. Formulations, Dosages, and Modes of Administration

The bacterial live vector vaccines of the present invention may be administered to a subject to induce an immune response such as a protective immune response. In a preferred embodiment, the bacterial live vector vaccines of the present invention are administered in a pharmaceutical formulation.

The pharmaceutical formulations of the present invention may include pharmaceutically acceptable carriers, excipients, and other ingredients, such as adjuvants. Pharmaceutically acceptable carriers, excipients, other ingredients are those compounds, solutions, substances or materials that are compatible with the strains of the present invention and are not unduly deleterious to the recipient thereof. In particular, carriers, excipients, other ingredients of the present invention are those useful in preparing a pharmaceutical formulation that is generally safe, non-toxic and neither biologically nor otherwise undesirable, and that may present pharmacologically favorable profiles, and includes carriers, excipients, and other ingredients that are acceptable for veterinary use as well as human pharmaceutical use.

Suitable pharmaceutically acceptable carriers and excipients are well known in art and can be determined by those of skill in the art as the clinical situation warrants. The skilled artisan will understand that diluents are included within the scope of the terms carriers and excipients. Examples of suitable carriers and excipients include saline, buffered saline, dextrose, water, glycerol, ethanol, more particularly: (1) Dulbecco's phosphate buffered saline, pH about 7.4, containing about 1 mg/ml to 25 mg/ml human serum albumin, (2) 0.9% saline (0.9% w/v NaCl), (3) 5% (w/v) dextrose, and (4) water.

The mode of administration of the immunizing compositions of the present invention may be any suitable delivery means and/or methods that results in the induction of an immune response in the subject. Delivery means may include, without limitation, parenteral administration methods, such as subcutaneous (SC) injection, intravenous (IV) injection, transdermal, intramuscular (IM), intradermal (ID), as well as non-parenteral, e.g., oral, nasal, intravaginal, pulmonary (inhalation), ophthalmic, rectal administration, or by any other mode that results in the immunogenic composition contacting mucosal tissues. Preferably, administration is orally.

In one embodiment of the present invention, the immunizing compositions exists as an atomized dispersion for delivery by inhalation. Various liquid and powder formulations can be prepared by conventional methods for inhalation into the lungs of the subject to be treated. The atomized dispersion of the immunizing compositions typically contains carriers common for atomized or aerosolized dispersions, such as buffered saline and/or other compounds well known to those of skill in the art. The delivery of the immunogenic compositions via inhalation has the effect of rapidly dispersing the immunizing compositions to a large area of mucosal tissues as well as quick absorption by the blood for circulation of the immunizing compositions.

Additionally, immunizing compositions also exist in a liquid form. The liquid can be for oral dosage, for ophthalmic or nasal dosage as drops, or for use as an enema or douche. When the immunizing composition is formulated as a liquid, the liquid can be either a solution or a suspension of the immunizing composition. There are a variety of suitable formulations for the solution or suspension of the immunizing composition that are well know to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the immunizing compositions, wetting agents, sweeteners, and coloring and flavoring agents.

Delivery of the described immunizing compositions in liquid form via oral dosage exposes the mucosa of the gastrointestinal and urogenital tracts to the immunizing compositions. A suitable dose, stabilized to resist the pH extremes of the stomach, delivers the immunizing composition to all parts of the gastrointestinal tract, especially the upper portions thereof. Any methods of stabilizing the immunizing composition in a liquid oral dosage such that the effective delivery of the composition is distributed along the gastrointestinal tract are contemplated for use with the immunizing compositions described herein, including capsules and a resuspended buffer solution to protect the attenuated bacteria against the acidic pH. The particular pharmaceutically acceptable carriers or diluents employed are not critical to the present invention, and are conventional in the art. Examples of diluents include: buffers for buffering against gastric acid in the stomach, such as citrate buffer (pH 7.0) containing sucrose, bicarbonate buffer (pH 7.0) alone or bicarbonate buffer (pH 7.0) containing ascorbic acid, lactose, and optionally aspartame (Levine et al, Lancet, II:467-470 (1988)). Examples of carriers include: proteins, e.g., as found in skim milk; sugars, e.g., sucrose; or polyvinylpyrrolidone.

Delivery of the described immunizing compositions in liquid form via ophthalmic drops exposes the mucosa of the eyes and associated tissues to the immunizing compositions. A typical liquid carrier for eye drops is buffered and contains other compounds well known and easily identifiable to those of skill in the art.

Delivery of the described immunizing compositions in liquid form via nasal drops or aerosol exposes the mucosa of the nose and sinuses and associated tissues to the immunizing compositions. Liquid carriers for nasal drops are typically various forms of buffered saline.

Injectable formulations of the immunizing compositions may contain various carriers such as vegetable oils, dimethylacetamide, dimethylformamide, ethyl lactate, ethyl carbonate, isopropyl myristate, ethanol, polyols (glycerol, propylene glycol, and liquid polyethylene glycol) and the like. Physiologically acceptable excipients may include, for example, 5% dextrose, 0.9% saline, Ringer's solution or other suitable excipients. Intramuscular preparations can be dissolved and administered in a pharmaceutical excipient such as Water-for-Injection, 0.9% saline, or 5% glucose solution.

The bacterial live vector vaccines of the present invention may be administered to a subject in conjunction with other suitable pharmacologically or physiologically active agents, e.g., antigenic and/or other biologically active substances.

The bacterial live vector vaccines comprising a stabilized expression plasmid system may be administered to a subject prior to, concurrent with, or after expression of the selected antigen has begun. For example, bacterial live vector vaccines comprising a stabilized expression plasmid system may be cultured for a period of time prior to administration to a subject to enable the bacteria to produce sufficient amounts of the selected antigen, such that an immune response will be raised to the selected antigen upon administration of the bacteria.

The amount and rate of administration of the immunizing compositions of the present invention may be readily determined by those of ordinary skill in the art without undue experimentation, such as by use of conventional antibody titer determination techniques and conventional bioefficacy/biocompatibility protocols. The amount and rate of administration will vary based on factors such as the weight and health of the subject, the identity of the bacteria being administered to the subject, the identity of the polypeptide being expressed in those stains engineered to express a selected antigen, the desired therapeutic effect, the desired time span of bioactivity, and the mode of administration of the immunizing composition.

In general, the amount of an immunizing composition administered to a subject is an amount sufficient to induce an immune response in the subject to a bacterial live vector vaccine or to the selected antigen being expressed by the bacterial live vector vaccine (an immunologically-effective amount). Preferably, the immune response is a protective immune response.

Generally, the dosage employed will contain about $10^2$ cfu to $10^{10}$ cfu of the bacterial live vector vaccine, preferably about $10^2$ cfu to $10^7$ cfu, or about $10^6$ cfu to $10^9$ cfu. Formulations for oral administration comprise about $10^2$ cfu to $10^{10}$ cfu of the bacterial live vector vaccine, preferably about $10^6$ cfu to $10^9$ cfu, and the formulation is in a capsule or resuspended in a buffer solution to protect the attenuated bacteria against the acidic pH in the stomach. Formulations for nasal administration comprise about $10^2$ cfu to $10^{10}$ cfu of the bacterial live vector vaccine, preferably about $10^2$ cfu to $10^7$ cfu, and are used for intranasal administration in which the bacteria is given in drops or in aerosol.

The immunizing compositions may be administered in a single dose, or in multiple doses over prolonged periods of time. In particular, the immunizing compositions may be administered over a period of one week, two weeks, three weeks, one month, six weeks, two months, ten weeks, three months, four months, six months, one year, or for extended periods longer than one year.

The immunizing compositions may be provided in dosage unit for uniform dosage and ease of administration. Each dosage unit form contains a predetermined quantity of the bacterial live vector vaccine of the present invention calculated to produce a desired immune response, in association with a pharmaceutically acceptable carrier, excipient, or other ingredient.

The present invention also includes a kit comprising one or more of the immunizing compositions of the present invention, and optionally means for administering the compositions, and instructions for administering the compositions.

E. Examples

1. Bacterial Strains and Culturing Conditions

*Escherichia coli* strain DH5 alpha was used for all plasmid constructions. Live attenuated *Salmonella* Typhi strain CVD 908-htrA harbors deletion mutations in aroC and aroD, interrupting the aromatic compound biosynthesis pathway, and htrA, which encodes a stress response protein (see Infect Immun. 60:2 (1992), pp. 536-541 and J. Biotechnol. 44:1-3 (1996), pp. 193-196).

*E. coli* DH5 alpha was grown using Luria Bertani (LB) liquid medium or agar (Difco, Detroit, Mich.) supplemented with antibiotics carbenicillin (carb; 50 μg/ml), kanamycin (kan; 50 μg/ml) or chloramphenicol (cml; 25 μg/ml), where necessary. CVD 908-htrA was grown in LB media supplemented with 2,3-dihydroxybenzoic acid (DHB) as previously described[36, 45]. Liquid cultures were incubated at 30° C. or 37° C. at 250 rpm for 16-24 hrs unless stated otherwise.

Modified minimal medium (MMM) used for complementation analysis was composed of M9 salts (K2HPO4, 7 g/l; KH2PO4, 3 g/l; (NH4)2SO4, 1 g/l (pH7.5)), 0.5% (w/v) casamino acids (Difco), 0.5% (w/v) glucose, 0.01% (w/v) MgSO4.7H2O, 15 g of granulated agar (Difco) per liter and 1 μg/ml vitamin B1.

2. Plasmids and Molecular Genetic Techniques

Standard techniques were used for the construction of the plasmids represented here (see, for example, Sambrook et al., 1989 (supra) which is herein incorporated by reference in its entirety). Plasmid extraction and gel purification of DNA fragments were performed using QIAprep Spin Miniprep and QIAquick Gel Extraction kits, respectively, as directed by the manufacturer (Qiagen Inc., Valencia, Calif.). Plasmids pCR-Blunt II-TOPO (Invitrogen, Carlsbad, Calif.), pGEM®-T or pGEM®-T Easy (Promega, Madison, Wis.) were used as intermediates for cloning blunt ended polymerase chain reaction (PCR) products generated with Vent™ DNA Polymerase (New England Biolabs, Ipswich, Mass.). Plasmid pLowBlu 184 (E. M. Barry, unpublished data; CVD, University of Maryland, Baltimore) is a low copy number plasmid based on pACYC184 (ATCC) but containing the lactose operon sequence from pGEM®-5Zf(+) (2767-273 bp; Promega, Madison, Wis.) in place of the tetracycline resistance gene between AvaI and HindIII. Taq-Pro™ DNA Polymerase (Denville Sci., Metuchen, N.J.) was used for lambda Red-mediated mutagenesis, and for diagnostic PCR using 5 ul of a single bacterial colony diluted in 20 μl of sterile water. Taq-Pro™ DNA Polymerase was also used to add to pre-treat PCR fragments generated by Vent™ DNA Polymerase prior to cloning into pGEM®-T or pGEM®-T Easy. All restriction enzymes were purchased from New England Biolabs. T4 DNA polymerase (NEB) was used to create blunt ended DNA fragments. Electroporation of strains was performed in a Gene Pulser apparatus (Bio-Rad) set at 2.5 kV, 200Ω, and 25 μF. Molecular weight markers used in DNA gel electrophoresis are O'GeneRuler™ 1 kb DNA Ladder, ready-to-use (#SM1163, Fermentas, Hanover, Md.).

3. Lambda Red-Mediated Mutagenesis

This technique was performed as described by Datsenko and Wanner (Proc Natl Acad Sci USA. 2000 Jun. 6; 97(12): 6640-50), with certain modifications. Briefly, 10 colonies of bacteria carrying Red helper plasmid pKD46 (reader is directed to the Datsenko and Wanner reference for more information about this plasmid) were added to 20 ml of 2× soy media supplemented with carbenicillin and L-arabinose (0.2%) and grown at 30° C., 250 rpm for 3 hrs (OD 600 nm of ~0.6). Bacteria were made electrocompetent by washing 3 times with cold sterile water and concentrating 100 fold. Competent cells were electroporated with 100 ηg-1 μg of gel-purified PCR product. Following electroporation, bacteria were repaired using 2× soy medium with or without guanine. Cells were incubated in 2× soy media at 37° C. for 3 hrs prior to plating on 2× soy agar containing guanine and cml overnight. Antibiotic resistant colonies were selected and screened via PCR for alterations in the chromosomal regions of interest. Positive colonies were re-streaked onto 2× soy media containing cml, but lacking carbenicillin, to ensure loss of pKD46. Removal of the cml resistance cassette was performed as described by Datsenko and Wanner and involved using pCP20. Colonies exhibiting the desired genotype were re-streaked on 2× soy media lacking antibiotics to ensure the loss of the antibiotic resistance phenotype. Those selected for storage were re-screened via PCR prior to freezing at −70° C. in 2× soy media containing 20% (v/v) glycerol.

4. Rationale for Construction and Use of SSB-Deleted Strains

It has been observed that it is extremely difficult to select for ligated plasmid constructs after introduction by electroporation into attenuated *Salmonella* Typhi vaccine strains. The engineering and recovery of SSB-encoding plasmids was therefore carried out in *E. coli* prior to introduction into ssb-deleted *Salmonella* Typhi. To accomplish this, Lambda Red-mediated mutagenesis was utilized as described above to delete ssb from the chromosome of *E. coli* DH5α, as well as from *Salmonella* Typhi CVD 908-htrA (described below in sections 5.1 and 5.2 respectively).

Figure 5:
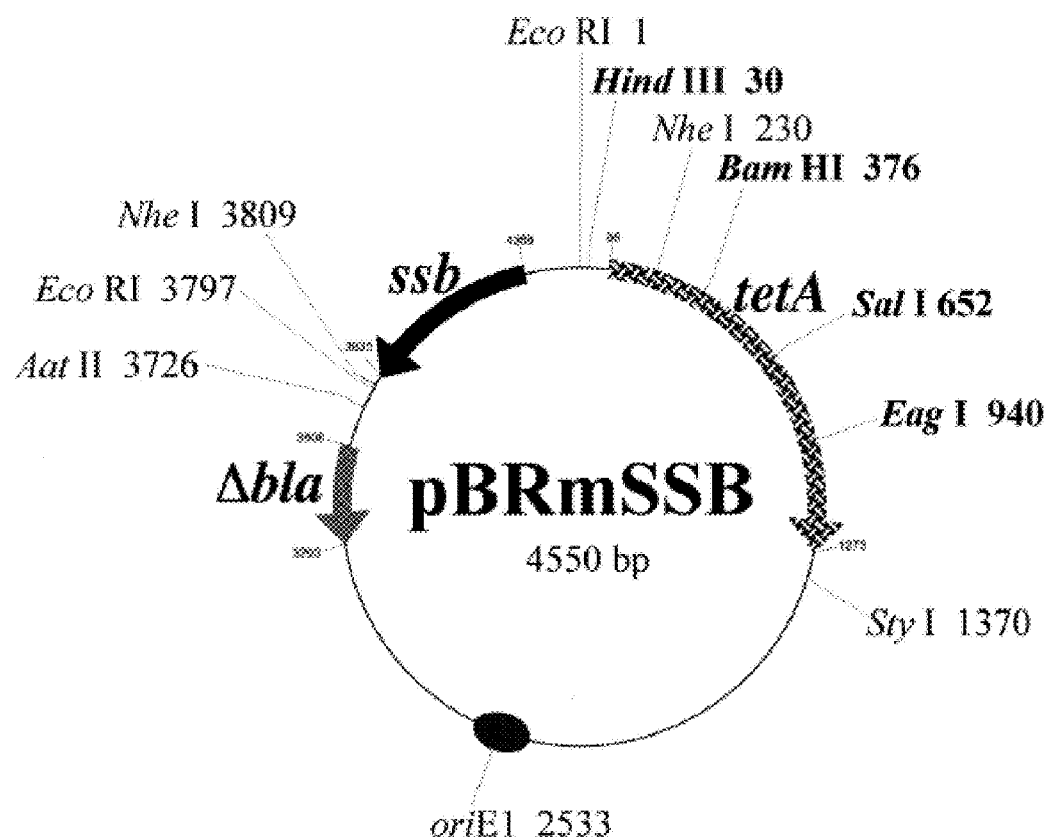
FIG. 5: genetic map of pBRmSSB. The sequence of pBRmSSB is set forth in SEQ ID NO:10.
Figure 6:
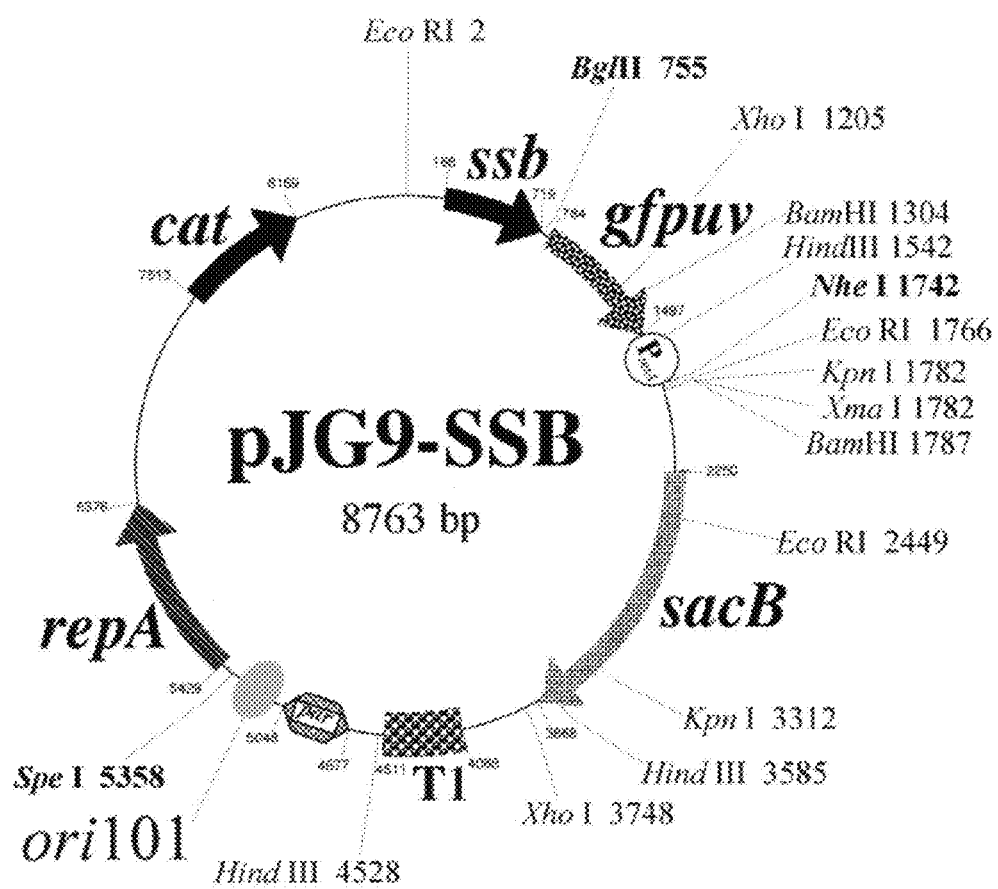
FIG. 6: genetic map of pJG9-SSB, a temperature-sensitive replicon derived from pSC101 carrying ssb, gfpuv, the cat chloramphenicol resistance allele, and the counterselectable marker sacB. The sequence of pJG9-SSB is set forth in SEQ ID NO:8.

During the construction of the chromosomal ssb deletions, all strains were complemented for SSB in trans by pBRmSSB, a pBR322-based plasmid encoding ssb and its two native promoters (SEQ ID NO:10; FIG. 5). After chromosomal deletions were accomplished, pBRmSSB was replaced in all cases with pJG9-SSB (SEQ ID NO:8; FIG. 6), a temperature-sensitive replicon derived from pSC101[8] carrying ssb, the cat chloramphenicol resistance allele, and the counterselectable marker sacB. Prior to final electroporation into *Salmonella* Typhi live vectors, SSB-stabilized plasmids are recovered in DH5αssb(pJG9-SSB) by selecting on solid Luria-Bertani (LB) medium supplemented only with 16% sucrose (to select for loss of sacB) and incubated at 42° C. (to inactivate the pJG9-SSB ori101). The desired supercoiled plasmids are then purified and recovered in CVD 908-htrAssb (pJG9-SSB) using the same procedure.

5.1. Construction of the Ssb Deletion in DH5α

SSB expression can occur via two ssb-specific promoters, one constitutive and the other inducible[11] (see FIG. 1). Expression from the inducible promoter is regulated by LexA, a repressor protein that is induced as part of the bacterial SOS response to DNA damage. LexA binding upstream of ssb also represses the divergent promoter that governs UvrA expression, another protein involved in the repair of DNA damage. pBRmSSB was introduced into DH5α and Lambda Red mutagenesis was used to delete ssb and the two ssb-specific promoters, leaving $P_{uvrA}$ intact. Construction of the critical DH5αssb(pJG9-SSB) strain, in which pBRmSSB was replaced with the temperature-sensitive pJG9-SSB replicon, was accomplished by exchanging these two plasmids in the presence of coumermycin at a concentration of 5 μg/ml to inhibit the ColE1 origin of replication in pBRmSSB[26], in addition to selection with 20 μg/ml chloramphenicol for incoming pJG9-SSB. Loss of pBRmSSB was confirmed by PCR analysis using primers specific for tetA and oriE1 in separate reactions. DH5αssb(pJG9-SSB) was used only as a strain for recovery of SSB-plasmids destined for electroporation into *Salmonella* Typhi vaccine strains. Therefore, any un-intended mutagenic effects of coumermycin upon either the *E. coli* chromosome or pJG9-SSB were irrelevant, since the desired SSB-stabilized expression plasmids is screened for antigen expression and then purified prior to electroporation into CVD 908-htrA.

5.2. Construction of the Ssb Deletion in *Salmonella* Typhi CVD 908-htrA

Lambda Red mutagenesis was used to delete ssb from CVD 908-htrA using the strategy used for DH5α. Construction of CVD 908-htrAssb(pJG9-SSB) was accomplished by electroporating pJG9-SSB into CVD 908-htrAssb (pBRmSSB), and CVD 908-htrAssb(pJG9-SSB) was recovered on LB medium containing 20 μg/ml chloramphenicol and 2,3-dihydroxybenzoate (DHB), a supplement required by all ΔaroCΔaroD attenuated auxotrophs. Spontaneous curing of pBRmSSB was again confirmed by PCR analysis using primers specific for tetA and oriE1 in separate reactions.

The ease of replacing pJG9-SSB with incoming foreign antigen-expression plasmids was confirmed by constructing the medium copy test plasmid pGEN222AKS (~15 copies per cell, SEQ ID NO: 9; FIG. 2), encoding resistance to ampicillin (bla) and kanamycin (aph), as well as carrying a complete plasmid maintenance system (hok-sok+parM+parR=hok-sok/parA) and also encoding SSB and UV-fluorescent GFPuv. Electroporation of supercoiled pGEN222AKS into CVD 908-htrAssb(pJG9-SSB), followed by selection at 42° C. on LB agar containing 16% sucrose+DHB, resulted in selection of CVD 908-htrAssb(pGEN222AKS). Loss of pJG9-SSB was confirmed by PCR analysis using primers specific for sacB, cat, and ori101 in separate reactions.

The stability of pGEN222AKS, both within CVD 908-htrA (i.e. wild-type for ssb) and within CVD 908-htrAssb, when both strains were passaged in the absence of antibiotic selection, was also examined. aph was included within pGEN222AKS because some growth inhibition of CVD 908-htrA was previously observed when grown using kanamycin selection versus selection with other antibiotics including carbenicillin and tetracycline. gfpuv was also included for its growth inhibitory effects on CVD 908-htrA, as well as to provide a convenient fluorescence screen for plasmid retention.

Both strains were grown for 5 hours in LB broth containing DHB plus carbenicillin to ensure a healthy and uniform starting population of live vectors carrying the test expression plasmid. Cultures were then diluted 1:1000 into LB medium containing only DHB and grown for 24 hours at 37° C. After 24 hrs, the frequency of recovery for plasmid-bearing CVD 908-htrA(pGEN222AKS) was only 1%, as determined by comparison of viable counts on LB agar with and without 50 μg/ml carbenicillin. The same frequency of 1% was observed when colonies grown without selection were examined directly for GFPuv fluorescence. However, the frequency of recovery for CVD 908-htrAssb(pGEN222AKS) was 100% by the same measures, even after passing without selection for 5 days.

5.3 Lambda Red Mediated Mutagenesis of CVD 908-htrA and DH5 Alpha

Lambda Red Mediated Mutagenesis was performed in *Salmonella enterica* serovar Typhi vaccine strain CVD 908-htrA and *E. coli* strain DH5 alpha in three stages as follows.

Stage 1 involved the PCR amplification of a DNA fragment upstream of ssb. Primers CVOL 110 and CVOL 111 (Table 1) were used to amplify SSBm1 (~670 bp) with CVD 1208s genomic DNA as template to delete ssb from DH5 alpha. This is because the region upstream of ssb is >99% homologous in both strains. Primers CVOL 142 and CVOL 143 (Table 1) were used to amplify TYSSBm1 (~611 bp) with CVD 908-htrA as a template. It should be noted that SSBm1 and TYSSBm1 were designed to encode the uvrA promoter and the LexA binding region but not the two ssb promoters (FIG. 9A). The PCR products were cloned into pCR-Blunt II-TOPO, and fragment orientation identified via NdeI (in CVOL 111 and CVOL 143) digestion of plasmid clones with either SpeI or XhoI found in the pCR-Blunt II-TOPO multiple cloning site.

Stage 2 involved amplification of a DNA fragment downstream of ssb. Primers used were CVOL 104 and CVOL 138 (Table 1) with DH5 alpha as a template (producing K12SSBm2, ~560 bp), and CVOL 144 and CVOL 145 (Table 1) with CVD 908-htrA as a template (producing Ty2SSBm2). The resulting fragment was ligated into pCR-Blunt II-TOPO and excised by either NdeI-XhoI or NdeI-SpeI digestion. K12SSBm2 and TY2SSBm2 were then ligated into the corresponding pCR-Blunt II-TOPO containing SSBm1 or TY2SSBm1 previously digested with either NdeI-XhoI (for PCR products derived from DH5 alpha) or NdeI-SpeI (for PCR products derived from CVD 908-htrA) (FIG. 9B).

The final stage of template construction involved PCR amplification of a chloramphenicol (cml) resistance cassette from template pKD3 (Datsenko and Wanner, GenBank accession number AY048742) using primers CVOL 75 and CVOL 99 (Table 1). The ~1020 by product was ligated into pCR-Blunt II-TOPO, excised by a NheI-NdeI digestion and inserted into the NheI-NdeI digested plasmids containing SSBm1-K12SSBm2 or TY2SSBm1-TY2SSBm2. The final constructs contained a cml resistance cartridge flanked by regions homologous to those surrounding ssb on the chromosomes of DH5 alpha and CVD 908-htrA.

Mutagenesis was performed as described by Datsenko and Wanner (*PNAS USA* 97:6640-6645 (2000)), with minor modifications. Strains CVD 908-htrA and DH5 alpha were transformed via electroporation with pKD46 and pBRmSSB, using the technique described herein. pKD46 encodes a temperature sensitive origin of replication, and the λ Red recombinase under the control of an arabinose inducible promoter. Ten colonies of CVD 908-htrA or DH5 alpha carrying KD46 and pBRmSSB were added to 20 ml of 2× soy media with carbenecillin and L-arabinose (0.2%) and grown at 30° C., 250 rpm for 3 hrs ($OD_{600}$ nm of ~0.6). Competent cells were electroporated with 100 ηg-1 μg of gel-purified PCR product previously amplified using template SSBm1-cml-K12SSBm2 (for DH5 alpha) with primers CVOL 110 and CVOL 138, and TY2SSBm1-TY2SSBm2 (for CVD 908-htrA) with primers CVOL 142 and CVOL 145. Cells were incubated in 2× soy media at 37° C. for 3 hrs prior to plating on 2× soy agar containing guanine and chloramphenicol overnight.

Antibiotic resistant colonies were screened via PCR for the alterations in the chromosomal ssb gene using primers that are homologous to regions outside those used to construct the ssb deletion templates. These primers were CVOL 112 and CVOL 139 (Table 1) for colonies derived from DH5 alpha, and CVOL 140 and 141 (Table 1) for colonies derived from CVD 908-htrA.

Colonies found to contain cml resistance were re-streaked at 37° C. on 2× soy agar lacking carbenecillin to ensure loss of pKD46. Removal of the cml resistance cassette was performed as described by Datsenko and Wanner. The resulting Assb mutant bacteria containing a functional copy of ssb on the pBRmSSB plasmid (DH5 alphaAssb1.1 and CVD 908-htrAΔssb1.1) were screened via PCR as described above for the absence of chromosomal ssb. Colonies exhibiting the correct genotype were re-streaked on 2× soy media to ensure loss of all antibiotic resistance. Those selected for storage were re-screened via PCR prior to freezing at −70° C. in 2× soy media containing 20% (v/v) glycerol.

TABLE 1

| Name | Sequence[a] | Target | Region[b] | SEQ ID NO: |
|---|---|---|---|---|
| CVOL 75 | <u>CATATG</u>AATATCCTCCTTAGTTCCTATTCC | pKD3 | 1044-1015 | 11 |
| CVOL 99 | <u>GCTAGC</u>GTGTAGGCTGGAGCTGCTTCGAAGTTCCTA | pKD3 | 31-57 | 12 |
| CVOL 104 | <u>CATATG</u>TTATATTGTTTTAAGGTGGATGATTAAAG | 2457t<br>K12 | 3456522-3456550<br>4272704-4272733 | 13 |
| CVOL 110 | GGAAAGATCGCAGACTTCGCCATCAATACG | 2457t | 3455161-3455190 | 14 |
| CVOL 111 | <u>CATATG</u>TTATTATTATT<u>AGCTAG</u>CTACTGTATATTC ATTCAGGTCAATTTGTGT | 2457t | 3455830-3455794 | 15 |
| CVOL 112 | GAAGCGATCAACCACCACTTCAATGGTATG | 2457t<br>K12 | 3455101-3455130<br>4271274-4271303 | 16 |
| CVOL 138 | <u>CTCGAGACTAGT</u>TCTGTACAGCAATAAAAGTCACG GCCTAAT | K12 | 4273260-4273231 | 17 |
| CVOL 139 | CTACAGGAATGCAGAGGCGGCGGGAAGATA | K12 | 4273320-4273291 | 18 |

TABLE 1-continued

| Name Sequence[a] | Target | Region[b] | SEQ ID NO: |
|---|---|---|---|
| CVOL 140 TTCGGCGGATCGGAGAGATCGCAGACTTCG | Ty2 | 3455150-3455179 | 19 |
| CVOL 141 AGACATCAATTATTGCACTAACTATATCTT | Ty2 | 4307282-4307251 | 20 |
| CVOL 142 CTTGCCAGATTTTCCAGCGTTTTGGTGTGT | Ty2 | 4305301-4305330 | 21 |
| CVOL 143 CATATGTTATTATTATTAGCTAGCTACTGTATATTC AAACAGGTTAAATTGTGT | Ty2 | 4305912-4305883 | 22 |
| CVOL 144 CATATGCATTTTCGCTATAGTTCTCGTCTGCTGAA A | Ty2 | 4306619-4306650 | 23 |
| CVOL 145 CTCGAGACTAGTTAGCTAATCATTGAAACTCTAAA TCATTTT | Ty2 | 4307282-4307251 | 24 |

[a]Primers are listed in 5' → 3' direction with restriction enzyme cleavage sites underlined.
[b]Indicates region of homology to plasmid pKD3 (Genbank accession number AY048742), the chromosome of parent S. flexneri 2a strain 2457t (Genbank accession number AE014073) or its virulence plasmid (VP; Genebank accession number M22802, S. Typhi parent strain Ty2 (Genbank accession number AE014613) or E. coli K12 genome (Genbank accession number U00096).

6. Alternate Non-Antibiotic Selection Method: Microcin H47

The use of microcins as an alternative non-chromosomal selection system was also investigated. One significant advantage for using this approach is that microcin-selected plasmids can be readily introduced into a variety of currently available live vectors, without further mutagenesis of the attenuated live vector chromosome.

Figure 3:
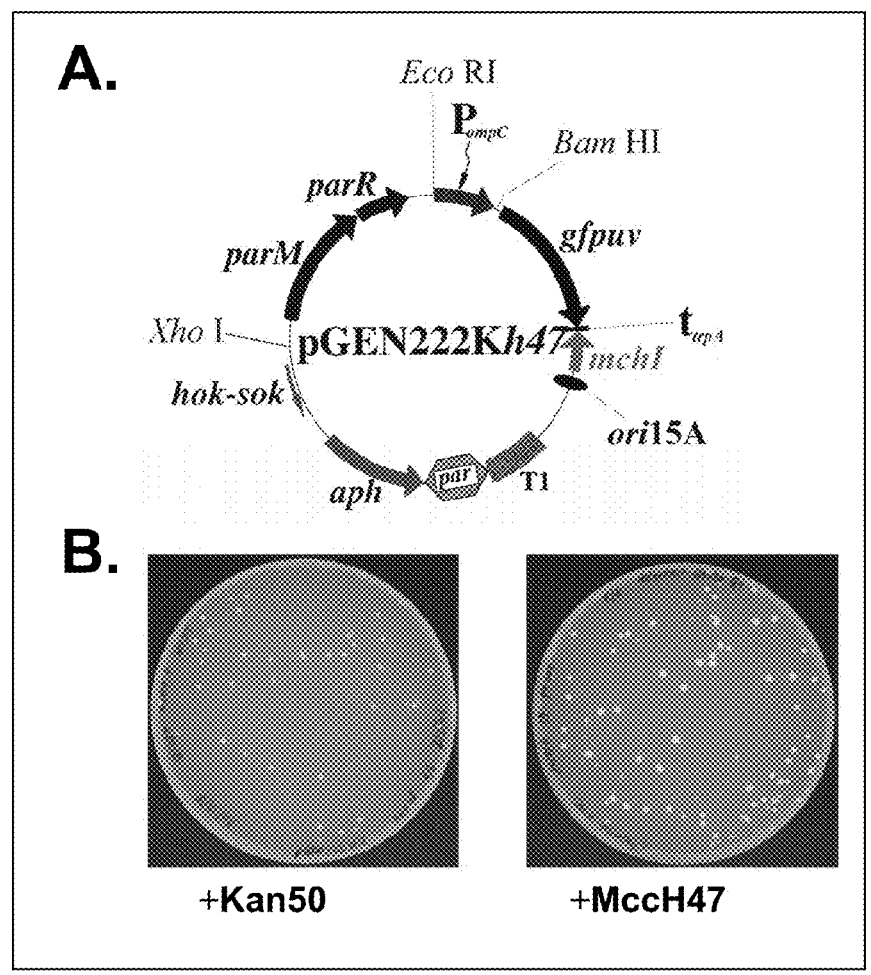
FIG. 3A: genetic map of pGEN222Kh47.
FIG. 3B: results of DH5a(pGEN222 Kh47) transformants selected on LB plates containing either 50 μg/ml kanamycin (+Kan50) or microcin H47 (+McCH47).

Preliminary experiments indicated that CVD 908-htrA was sensitive to McCH47 exported by E. coli strains carrying the mch47 operon. Therefore, a plasmid selection system based on McCH47 selection in susceptible strains with incoming plasmids encoding the McCH47 immunity protein MchI was developed. A test plasmid expressing GFPuv was derived from pGEN222 in which the immunity gene mchI was inserted just downstream of the trpA terminator and adjacent to ori15A (pGEN222 Kh47; SEQ ID NO:31; FIG. 3A). This plasmid was introduced by chemical transformation into commercially available library-grade competent DH5α (Invitrogen) to create DH5α (pGEN222 Kh47).

Because McCH47 was not commercially available, a procedure was devised in which a McCH47-expressing strain was used to impregnate agar plates with microcin H47. First, a cellulose membrane (Spectra/Por 1 membrane, Spectrum Laboratories, Inc.) permeable to proteins less than 8 kDa was overlain onto LB agar. A culture of DH5a(pEX4), carrying the entire functional mch47 operon (GenBank accession number AJ009631) on the pBR322-derived plasmid pEX4 (Lavina et al., J. Bacteriol. 172:6585-6588 (1990)), was then mixed with top agar and poured onto the membrane. Plates were incubated at 37° C. for 48 hours, allowing McCH47 to be secreted out of DH5a(pEX4) and diffuse through the membrane into the agar below. The membrane was then removed, and the plates were used for selection of DH5α (pGEN222Kh47) transformants resistant to McCH47 killing.

Because pGEN222Kh47 also carries the aph allele, the efficiency of selection with kanamycin could be compared to the efficiency of non-antibiotic selection using microcin H47. DH5α(pGEN222Kh47) transformants were therefore selected at 37° C. on LB plates containing either with 50 μg/ml kanamycin or microcin H47, incubated for 24 hours. As shown in FIG. 3B, the observed numbers of fluorescent bacteria indicate that the efficiency of selection using McCH47 was equivalent to that using kanamycin when equal amounts of transformed cells were plated. The McCH47 plates shown were allowed to incubate for a further 24 hours, and the much larger colonies were examined for sectoring of fluorescence as evidence of plasmid instability. No sectoring was observed. These data strongly support use of microcin H47 as yet another non-antibiotic plasmid selection system for development in attenuated Salmonella Typhi live vectors.

Figure 7:
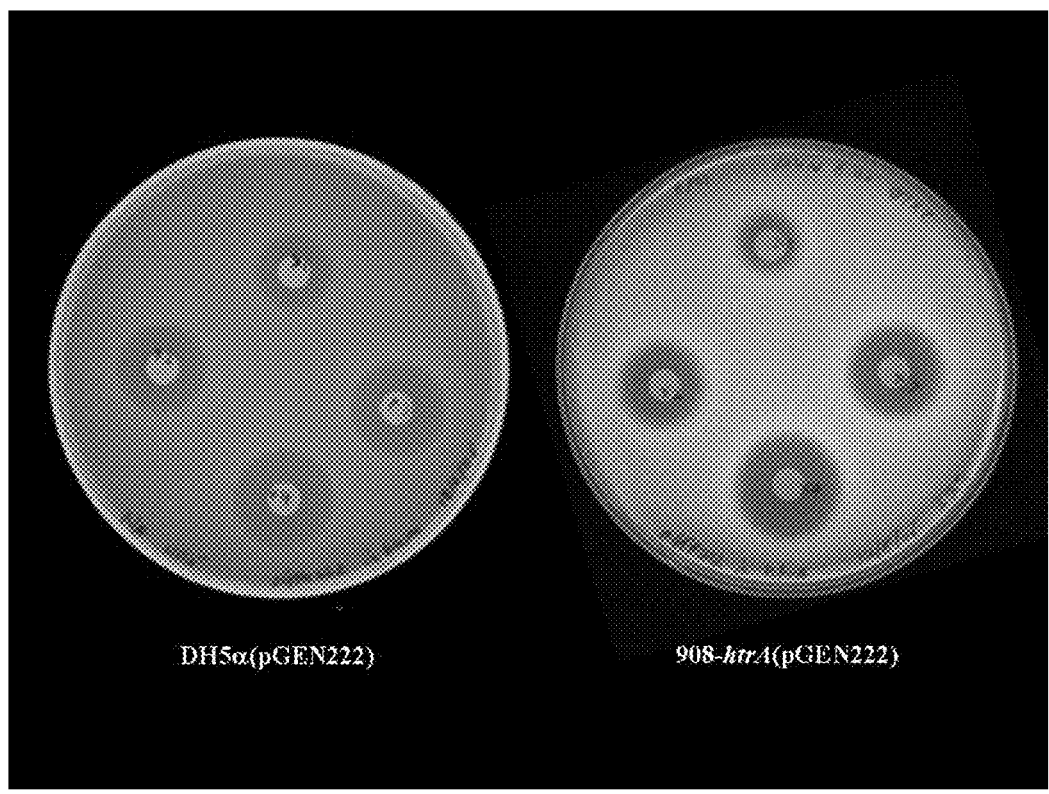
FIG. 7: growth inhibition of DH5a(pGEN222) and 908-htrA(pGEN222) in the presence of McCH47.

The sensitivity of Salmonella Typhi to McCH47 is augmented in strains of Salmonella Typhi in which expression of the Vi antigen was blocked. As shown in FIG. 7, McCH47 was equally effective in killing DH5a(pGEN222) and 908-htrA (pGEN222) where 908-htrA(pGEN222) did not produce the Vi antigen. Vi synthesis was blocked by growing 908-htrA (pGEN222) on Luria-Bertani solid medium with high osmolarity where the concentration of NaCl was increased from 0.15 M (normal medium) to 0.7 M (high osmolarity, which down-regulates Vi synthesis). In this experiment, DH5α (pGEN222) was grown on normal medium.

7. Murine Intranasal Model for Pre-Clinical Testing of Salmonella Typhi Live Vectors.

The lack of a practical small animal model to evaluate the immunogenicity of Salmonella Typhi-based live vector vaccines, prior to Phase I or Phase II clinical trials, has impeded live vector development.

Salmonella Typhi is a highly host-restricted human pathogen that is incapable of inducing a progressive systemic infection in conventional or germfree animal models by either oral or parenteral inoculation[15, 65]. Nevertheless, depending on the challenge dose and route of administration, Salmonella Typhi can establish a limited infection in the fixed macrophages of the murine reticuloendothelial system[15, 38, 39, 65]. Previous work[36] compared serum antibody responses of mice, immunized by orogastric or intranasal routes with CVD-908 carrying a plasmid encoding a protein fusion of tetanus toxin fragment C fused to the N-terminus of the eukaryotic cell receptor binding domain of diphtheria toxin (fragC-bDT)[36]. While orogastric immunization was not immunogenic, intranasal immunization elicited high titers of serum IgG antibodies specific for both the heterologous antigen (i.e., fragment C fusion domain) and the attenuated Salmonella Typhi carrier strain. Reciprocal geometric mean titers exceeding $10^4$ for anti-tetanus toxin and $10^3$ for *Salmonella* Typhi LPS were routinely observed after one boosting immunization. These titers were comparable to serum responses observed when immunizing mice intranasally with *Salmonella Typhimurium* strains expressing the identical heterologous antigen within the identical expression plasmid.

In addition, these serum tetanus antitoxin responses were shown to contain neutralizing tetanus antibodies which conferred 100% protection against challenge with 100 50% lethal doses of tetanus toxin that rapidly killed all control mice immunized with CVD 908 alone. Similar serum immune responses for intranasal immunization of mice with attenuated *Salmonella* Typhi carrier strains were also reported by Barry et al.[6] who demonstrated serum immune responses to both domains of a fusion protein containing fragment C fused at its carboxyl terminus to a truncated non-catalytic 51 subunit of pertussis toxin. It was further demonstrated that the serum IgG pertussis antitoxin response contained neutralizing antitoxin as judged by a CHO cell neutralization assay. Interestingly, the S1 subunit alone expressed poorly in the cytoplasm of CVD 908-htrA and was not immunogenic. The intranasal route for inoculation of mice constitutes a significant breakthrough in the development of a practical animal model for examining the immunogenicity and protective efficacy of heterologous antigens expressed within *Salmonella* Typhi-based live vector vaccines.

8. Immunogenicity of PA83 Delivered by CVD 908-htrA

In earlier work with first-generation expression plasmids, the immunogenicity of the *Bacillus anthracis* Protective Antigen PA83 was tested. Two codon-optimized cassettes were synthesized, with one encoding a ClyA-PA83 fusion protein (SEQ ID NO:33), wherein PA83 was fused to the carboxyl terminus of ClyA (encoded by pSEC91-83; SEQ ID NO:32) and the other encoding unfused PA83 (SEQ ID NO:26) for cytoplasmic expression (encoded by pPA83; SEQ ID NO:25). Upon introduction of pSEC91-83 and pPA83 into CVD 908-htrA, Western immunoblot analysis confirmed excellent expression of both PA83-derived antigens (data not shown). The immunogenicity of the bacterial live vector vaccines CVD 908-htrA(pPA83) and CVD 908-htrA(pSEC91-83) was compared in mice using a heterologous 2-prime/boost strategy in which mice were primed twice intranasally with $10^9$ cfu of live vector on days 0 and 14, and then boosted intramuscularly (i.m.) on day 28 with 0.5 μg of rPA83 adsorbed to Alhydrogel adjuvant (Accurate Chemical & Scientific Corp.). Pooled sera were used for ELISA and toxin neutralizing antibody (TNA) determinations, and results are presented in Table 2.

These data show that both PA83-encoding alleles, when expressed using the attenuated CVD 908-htrA vaccine strain, elicit anthrax toxin-specific neutralizing antibody responses. While export of PA83 as a ClyA-PA83 protein fusion improves the kinetics of the PA-specific antibody response, the peak titers for both strains are comparable, as were peak TNA responses.

In other preliminary experiments examining the boosting efficiency of purified PA83, it was observed that in mice primed only with empty live vector or PBS (i.e., unprimed for Protective Antigen), delivery of even high booster doses of PA83 elicits only modest antitoxin responses (data not shown). Therefore, for further experiments, antitoxin TNA responses may be improved by priming with two intranasal doses of live vector expressing codon-optimized PA83 from SSB-stabilized plasmids, and boosting i.m. with 10 μg of purified PA83 adsorbed to Alhydrogel.

9. Immunogenicity of ClyA-D4 Protein Fusions

In studies designed to examine the immunogenicity of ClyA-D4 protein fusions, a synthetic gene (d4) encoding protective antigen domain 4 of *Bacillus anthracis*, genetically fused in-frame to the carboxyl terminus of *Salmonella* Typhi ClyA (clyA::d4), was engineered[35]. The sequence of the ClyA::D4 fusion protein is shown in SEQ ID NO:34. The sequence encoding the ClyA::D4 fusion protein is shown in SEQ ID NO:28. A further isogenic construct was made for expression of unfused D4 within the cytoplasm. The amino acid sequence of unfused D4 is shown in SEQ ID NO:36. The nucleic acid sequence encoding unfused D4 is shown in SEQ ID NO:35. All constructions were carried out as described above in Section 8 for ClyA-PA83 and unfused PA83 expression plasmids. After electroporation of the resulting pSEC91-D4 and pSEC91-D4c constructs into CVD 908-htrA by electroporation, the immunogenicity of exported versus cytoplasmically expressed un-fused D4 was assessed using the murine intranasal model of immunogenicity.

Mice were randomly assorted and immunized with two doses of the live vector CVD 908-htrA constructs on days 0 and 28. 11 of 15 mice immunized with two doses of CVD 908-htrA exporting ClyA-D4 exhibited seroconversion with a peak anti-PA geometric mean titer (GMT) of 254. In contrast, only 1 of 16 mice immunized with the cytoplasmic expression construct manifested seroconversion (p=0.0002); responses in the latter group of mice differed little from controls (p=0.347).

Studies were also performed on whether *Salmonella* Typhi exporting ClyA-D4 could elicit cell-mediated immunity and whether protein export would influence the outcome of T cell responses in comparison with cytoplasmic expression. The

TABLE 2

Heterologous 2-prime/boosting strategy using CVD 908-htrA live vectors induces neutralizing antibody responses in mice after boosting with purified PA83.

| Priming agent [a] | Boosting agent [b] | Anti-PA titer (pooled sera) [c] | | | | | TNA [d] |
|---|---|---|---|---|---|---|---|
| | | Day −1 | Day 28 | Day 35 | Day 42 | Day 56 | Day 56 |
| htrA | Rpa83 | <25 | 87 | 122 | 278 | 4,479 | 6 |
| htrA(pPA-83) | rPA83 | <25 | 92 | 383 | 5,839 | 28,491 | 43 |
| htrA(pSEC91-PA83) | rPA83 | <25 | 98 | 26,322 | 60,501 | 64,626 | 43 |
| PBS | PBS | <25 | <25 | <25 | <25 | <25 | 0 |

[a] $10^9$ cfu in 10 μl administered intranasally; 12 mice per group for PA83, 10 mice for htrA group, 5 mice for PBS group.
[b] All animals boosted with 0.5 μg rPA83 (VaxGen) adsorbed to 0.075 mg Alhydrogel in 50 μl administered intramuscularly.
[c] Reported in ELISA Units (EU).
[d] Pooled sera; method of Quinn et al[80]; values reported as geometric means of ED50s; values below 25 are not statistically significant.

frequencies of IFN-γ and IL-5 secreting cells in the spleens from mice immunized with CVD 908-htrA alone or expressing D4 were measured by ELISPOT upon in vitro stimulation with rPA83. Mice that received CVD 908-htrA expressing D4 (both exported and cytoplasmic) showed IFN-γ responses that were significantly higher than those of the control group that received CVD 908-htrA alone (p=0.008 and p=0.019 respectively), as well as superior IL-5 responses (p=0.015 and p=0.040) respectively). Mice that received CVD 908-htrA exporting ClyA-D4 exhibited a slightly higher frequency of both IFN-γ and IL-5 secreting cells compared with mice immunized with CVD 908-htrA expressing D4 cytoplasmically, although the difference was not statistically significant. These data demonstrate the feasibility of developing a safe and immunogenic live vector-based vaccine against anthrax, using multicopy expression plasmids selected without the use of antibiotics.

10. Non-Antibiotic, Non-Catalytic, Plasmid Selection System for Stable Expression of Protective Antigen PA83 in an Attenuated *Salmonella* Typhi Vaccine Strain Both medium (~15 copies per chromosomal equivalent) and low copy number (~5 copies per chromosomal equivalent) expression plasmids are engineered to encode wildtype ssb. These modified plasmids are then used to express full-length PA83 from anthrax toxin in *Salmonella* Typhi CVD 908-htrAssb, and are tested for the ability to elicit antitoxin immunity (as judged by measurement of toxin neutralizing antibody responses) using the murine intranasal model of immunogenicity.

The use of ssb in selecting expression constructs introduced into CVD 908-htrA will be pursued for several reasons. First, preliminary data described above (Section 5.2) clearly demonstrates the efficiency of selecting and maintaining SSB-selected plasmids within CVD 908-htrAssb for greater than 150 generations in vitro. SSB is essential to DNA metabolism and must be continuously available to CVD 908-htrAssb to allow live vector replication. Therefore, SSB-selected plasmids encoding PA83 are expected to be stable in vivo as well as in vitro, enhancing foreign antigen-specific protective immunity. Since SSB is expected to function in vivo as a post-segregational killing system, the hok-sok system will be unnecessary and will therefore be removed. Should expression of PA83 from 15 copies of these plasmids prove to be unexpectedly toxic, the lower 5 copy expression plasmids will be used for the live vaccine.

It is becoming increasingly clear that toxin neutralizing antibody (TNA) responses function as a reliable correlate of protection in anthrax challenge studies using a variety of animal models[56,72,74], as well as for humans[76]. For this reason, focus will be on peak TNA responses as the critical measurement assessing the immunogenicity of live vector constructs. Total PA-specific IgG titers quantitated by ELISA will be used only to detect when peak serum responses occur.

A new set of isogenic expression plasmids will be constructed using the ori15A and ori101 replicons. These plasmids will have a backbone organization identical to that represented in FIG. 4. Because the origins of replication are sequestered by transcriptional termination signals at both the 5'-proximal and 3'-proximal termini, variations in copy number due to read-through transcription from other promoters within these expression plasmids will be minimized.

Plasmids may retain the parA active partitioning system to enhance plasmid inheritance in vivo. bla, encoding resistance to ampicillin and carbenicillin, may also be retained for efficient recovery of intermediate constructions; it has been observed that recombinants selected using the SSB system grow very slowly in 16% sucrose at 42° C., often requiring 2 days for visible colony formation. However, bla will be engineered within a cassette flanked by XbaI restriction sites so that prior to final introduction into *Salmonella* Typhi, the gene can be deleted from PA83-expressing constructs by digestion with XbaI, re-ligated, and recovered in DH5αssb(pJG9-SSB) plated on solid medium containing 16% sucrose and incubated at 42° C.

Recombinant PA83 supercoiled vaccine plasmids will then be purified, electroporated into CVD 908-htrAssb(pJG9-SSB), and the desired non-drug resistant live vectors recovered at 42° C. on media containing 16% sucrose. Successful replacement of pJG9-SSB will be confirmed by PCR using primers specific for sacB, cat, and ori101 in separate reactions.

Both clyA-pa83 and unfused pa83 genes can be inserted as SpeI-NheI cassettes into SSB-stabilized ori15A and ori101 replicons, generating pSEC91S-PA83 and pGEN222S-PA83 (medium copy plasmids; secreted and cytoplasmic alleles respectively) or pSEC10S-PA83, and pGEN$_2$O$_6$S-PA83 (low copy; secreted and cytoplasmic alleles respectively). Comparable expression of full-length PA83 by all constructs after introduction into CVD 908-htrAssb will be confirmed by western immunoblot analysis using goat polyclonal IgG antibody against Protective Antigen (List Biologicals).

The immunogenicity of the resulting live vector strains will be compared in mice immunized intranasally using a heterologous 2-prime-boost strategy. Mice will be randomly assorted into 4 equal-sized groups, each immunized with $5 \times 10^9$ colony forming units (CFUs) of one of the following: 1) CVD 908-htrAssb(pSEC91S-PA83), 2) CVD 908-htrAssb (pGEN222S-PA83), 3) CVD 908-htrAssb(pSEC10S-PA83), and 4) CVD 908-htrAssb(pGEN206S-PA83). All mice will be intranasally primed with live vectors on days 0 and 14, and boosted i.m. 4 weeks later (day 42) with 10 μg recombinant PA83 adsorbed to Alhydrogel. Sera will be collected on days −1, 13, 27, 41, 49, and 56 and analyzed for TNA responses using the method of Quinn et al[80]. It is hypothesized that CVD 908-htrAssb(pSEC91S-PA83), which exports ClyA-PA83 fusion proteins expressed from stabilized medium copy plasmids, will elicit the highest TNA responses among the four strains. Statistical analysis may be on log$_{10}$ TNA titers by one-way analysis of variance (ANOVA) and Hsu's multiple comparison procedure[46], which is designed to identify the best among several treatments. One-way ANOVA may be used rather than 2×2 factorial analysis in order to allow for possible interaction between the secreted/cytoplasmic and medium/low copy number factors. Within each group, log$_{10}$ TNA is assume to be normally distributed, with standard deviation estimated from previous experiments as 0.31. If the true ratio of the highest to second highest geometric mean titer (GMT) in the four groups is 1.9 or higher (i.e., difference in mean log$_{10}$ TNA titers >0.2788), then for groups of size 20 the power to obtain a statistically significant difference among the groups at the 5% significance level by ANOVA will be at least 80%. However, for 80% power that the highest GMT will be significantly higher at the 5% level than the second highest in the Hsu procedure, the ratio of GMTs must be approximately 2.8 Power calculations were done using PASS 2005 (Number Cruncher Statistical Systems, Kaysville, Utah).

After determining the most immunogenic of the SSB-stabilized PA83-expressing constructs, a further experiment will be conducted in mice to compare the immunogenicity of SSB-stabilized live vectors versus the analogous conventional kanamycin-selected PA83 plasmid carrying a hok-sok/parA plasmid maintenance system. Mice will again be immunized using the heterologous 2-prime-boost strategy. There will be 30 mice in each group. In mice immunized with CVD 908-htrAssb(pSEC91S-PA83), it is expected that the true TNA geometric mean titer will be at least two times as high as in mice immunized with CVD 908-htrA(pSEC91-PA83). Then the power to obtain a significant difference between strains with a t-test on $\log_{10}$ TNA titers at the two-sided 0.05 significance level will be 96%, again assuming a within-group standard deviation of 0.31. Power will be >80% for a ratio of TNA geometric mean titers of about 1.7 or higher. If TNA responses to live vectors carrying SSB-stabilized plasmids are superior to, or even similar to, responses to conventional expression plasmids, then SSB-stabilized plasmids should provide an excellent alternative to resistance markers for construction of plasmid-bearing live vector vaccines against anthrax.

In the unlikely event that SSB-stabilized plasmids expressing PA83 over-attenuate CVD 908-htrA and reduce immunogenicity when compared to conventional plasmids carrying a full hok-sok/parA plasmid maintenance system, an alternate selection system will be developed based on selection with microcin H47 of plasmids expressing the cognate H47 immunity protein. Medium and low copy plasmids will be engineered as for pGEN222 Kh47 (FIG. 3A), with aph replaced by an XbaI bla cassette, and the gfpuv cassette replaced either with clyA-pa83 or unfused pa83 cassettes. The immunogenicity of these constructs can then be compared with those of live vectors carrying SSB-stabilized or conventional plasmids to measure any improvement in antitoxin immunity.

11. Effective Maintenance of Higher Copy Number Plasmids at Maximum Copy Number in CVD 908-htrA Using SSB-Selected Plasmids The wildtype ssb allele, carried on multicopy expression plasmids from Section 10 above, will be replaced with an allele carrying the W54S mutation, known to be suppressed by over-expression of the W54S mutant allele from high copy number plasmids. The immunogenicity of live vectors carrying isogenic PA83 plasmids, encoding either ssb or $ssb^{W54S}$, will then be compared in mice.

Because the wildtype copy number of ssb per chromosomal equivalent is one, it is theoretically necessary for only one SSB-stabilized plasmid copy to be maintained within either CVD 908ssb or CVD 908-htrAssb live vectors. If true, multicopy SSB-stabilized expression plasmids may not achieve their maximum intended copy numbers in vivo, resulting in lower immune responses against the foreign antigen. The required conformation of SSB is a tetramer, and the W54S mutation destabilizes formation of this tetramer. However, when present on high copy number pUC plasmids, the lethality of $ssb^{W54S}$ was suppressed; Carlini et al[14] hypothesized that excess amounts of mutant protein pushed the dissociation equilibrium towards tetrameric forms. Experiments will be conducted to determine whether incorporation of the mutant $ssb^{W54S}$ allele can promote full retention of PA83-expressing plasmids.

Figure 4:
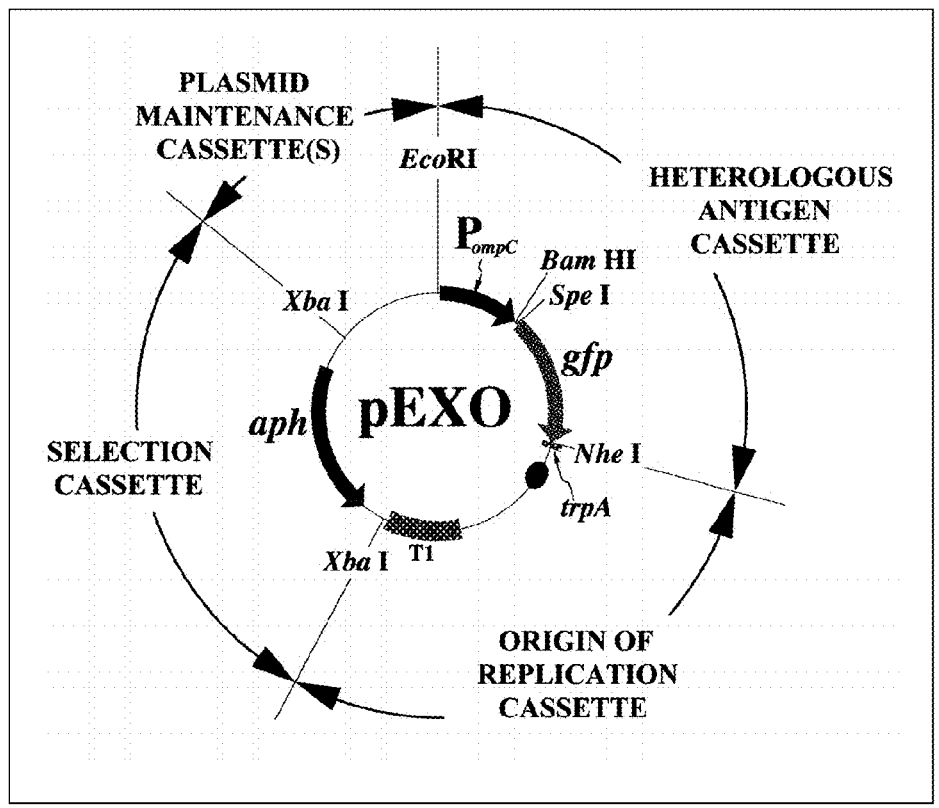
FIG. 4: genetic map of pEXO

A set of isogenic ori15A replicons will be constructed, stabilized either with ssb or $ssb^{W54S}$, and again patterned after the genetic organization shown in FIG. 4. As with the constructs described in Section 10 above, the parA active partitioning locus will be retained to enhance plasmid inheritance, and the bla gene encoding β-lactamase will also be retained within a cassette flanked by XbaI restriction sites, to select for intermediate constructs in the presence of 50 μg/ml of carbenicillin. GFPuv will be expressed as a test heterologous antigen, from a gfpuv allele that is transcriptionally controlled by $P_{ompC}$ and contained on a SpeI-NheI cassette. These plasmids will be designated as pGFPssb and $pGFPssb^{W54S}$. Improvement in GFPuv expression will be assayed in the optimum live vector determined in Section 10 above, by measuring the mean fluorescence of live vectors carrying pGFPssb or $pGFPssb^{W54S}$, grown in vitro under inducing conditions of high osmolarity without antibiotic selection, as previously described[37]. In addition, copy number in these strains will be directly determined, again grown in vitro in the absence of antibiotic selection under inducing conditions, using quantitative real-time PCR with the method of Lee et al[49, 50] and primer sets specific for plasmid gfpuv and the *Salmonella* chromosomal ssrB locus. Finally, the most immunogenic clyA-pa83 or unfused pa83 gene identified in Section 10 above will be inserted as a SpeI-NheI cassette into pGFPssb and $pGFPssb^{W54S}$, replacing gfpuv to create pPA83ssb and $pPA83ssb^{W54S}$.

Mice will be immunized using the heterologous 2-prime-boost strategy, with the optimum live vector strain carrying pPA83ssb or $pPA83ssb^{W54S}$. Mice will be randomly assorted into two groups of 30, and immunized using the heterologous 2-prime-boost strategy. It is hypothesized that in mice immunized with live vectors expressing PA83 from $ssb^{W54S}$-stabilized plasmids, the true TNA geometric mean titer will be at least two times as high as in mice immunized with ssb-stabilized plasmids. Then the power to find a statistically significant difference between strains with a t-test on $\log_{10}$ TNA titers at the two-sided 0.05 significance level will be 96%, assuming as before a within-group standard deviation of 0.31. Power will be ≥80% for a ratio of TNA geometric mean titers of about 1.7 or higher. In addition to measuring TNA responses, we will determine the in vivo copy number of both pPA83ssb or $pPA83ssb^{W54S}$ within our live vector using quantitative real time PCR analysis of bacterial DNA recovered from nasal associated lymphoid tissue (NALT), as carried out in Section 10 above, using primer sets specific for plasmid pa83 and the *Salmonella* chromosomal ssrB locus.

If no significant differences are detected for in vivo copy number or TNA responses between the optimum live vector strain carrying ssb- or $ssb^{W54S}$-stabilized PA83 plasmids and the within-group standard deviation of $\log_{10}$ TNA is 0.31, the observed ratio will be about 1.45 or less. In this case, we would conclude that stabilization of multicopy expression plasmids using $ssb^{W54S}$ is unnecessary.

12. Introduction of the SSB-Based Plasmid Selection System Will not Further Attenuate CVD 908-htrA, and Diminish Anthrax Toxin Immunity A chromosomal deletion of ssb within the chromosome of CVD 908, the less-attenuated parent of CVD 908-htrA, will be constructed and the immunogenicity of both strains carrying SSB-selected plasmids expressing PA83 will be compared in mice.

A successful attenuated bacterial vaccine strain can achieve high levels of immunity only by striking a delicate balance between attenuation and immunogenicity. It is clear that over-attenuated strains, while safe, are not highly immunogenic[51]. Experiments will be conducted to examine the theoretical possibility that a safe and sufficiently attenuated vaccine strain eliciting protective immunity may become over-attenuated after further genetic manipulation, and suffer an unacceptable reduction in immunogenicity. The concept of further strain attenuation, resulting from introduction of an expression plasmid selection system, was recently reported by Kotton et al for attenuated *Salmonella* Typhimurium live vectors delivering an HIV-1 Gag antigen[48]. Because CVD 908 is the less attenuated parent of CVD 908-htrA, it was hypothesized that any over-attenuation, resulting from introduction of a further chromosomal ssb deletion and SSB-stabilized PA83 constructs into CVD 908-htrA, may be reduced or eliminated by introduction of the SSB system into the more robust CVD 908 strain.

CVD 908ssb will be constructed using the Lambda Red-mediated mutagenesis procedures used to construct CVD 908-htrAssb. pBRmSSB will be used to temporarily trans-complement the chromosomal lesion, prior to introduction of the temperature-sensitive pJG9-SSB plasmid. The optimum SSB-stabilized PA83 expression plasmid identified in Section 10 above will be exchanged with pJG9-SSB. The exchange will be confirmed by PCR. Comparable levels of PA83 expression between CVD 908ssb and CVD 908-htrAssb grown in vitro will be confirmed by Western immunoblot analysis using goat polyclonal IgG antibody against Protective Antigen (List Biologicals). The immunogenicity of CVD 908ssb and CVD 908-htrAssb strains expressing PA83 will be compared using the murine intranasal model and measurement of peak TNA antitoxin responses.

Mice will be randomly assorted into 2 groups, and immunized intranasally using the heterologous 2-prime/boost strategy, as described for Section 10 above. It is hypothesized that in mice immunized with CVD 908ssb expressing PA83, the true TNA geometric mean titer will be at least two times as high as in mice immunized with CVD 908-htrAssb expressing PA83. Then the power to detect a significant difference between strains with a t-test on $\log_{10}$ TNA titers at the two-sided 0.05 significance level will be 96%, assuming a within-group standard deviation of 0.31. Power will be >80% for a ratio of TNA geometric mean titers of about 1.7 or higher.

If no significant difference in TNA responses between CVD 908ssb and CVD 908-htrAssb live vectors carrying SSB-stabilized PA83 plasmids is found and the within-group standard deviation of $\log_{10}$ TNA is 0.31 as assumed above, the observed ratio will be about 1.45 or less. In this case it would be concluded that introduction of ssb-stabilized expression plasmids into CVD 908-htrA does not result in any over-attenuation as an anthrax vaccine strain.

The SSB system developed here has broad application to a variety of vaccine approaches. The system can be introduced into various attenuated bacterial vaccine strains, producing commensal or other attenuated live vectors. This technology may also improve antigen production from stabilized plasmids in conventional bacterial strains used for purified protein vaccine production, and will further obviate the need for removal of trace antibiotic contaminants from final vaccine preparations. And finally, if the efficiency of plasmid DNA vaccine delivery into eukaryotic target cells by invasive *Salmonella* or *Shigella* vaccine strains (a process called bactofection[92]) is dependent on the retention of the DNA vaccine within a bacterium prior to DNA delivery, then the efficiency of delivery and resulting immunogenicity could be improved if SSB-stabilized DNA vaccines are used.

Each of the documents, publications, books, patents, published patent applications, reference materials, journal articles, and any other periodicals cited herein is hereby expressly incorporated herein it is entirety.

REFERENCE LIST

1. Abromaitis, S., S. Faucher, M. Beland, R. Curtiss, III, and F. Daigle. 2005. The presence of the tet gene from cloning vectors impairs *Salmonella* survival in macrophages. FEMS Microbiol. Lett. 242:305-312.
2. Altboum, Z., M. M. Levine, J. E. Galen, and E. M. Barry. 2003. Genetic characterization and immunogenicity of coli surface antigen 4 from enterotoxigenic *Escherichia coli* when it is expressed in a *Shigella* live-vector strain. Infect. Immun. 71:1352-1360.
3. Azpiroz, M. F. and M. Lavina. 2004. Involvement of enterobactin synthesis pathway in production of microcin 1147. Antimicrob. Agents Chemother. 48:1235-1241.
4. Azpiroz, M. F., E. Rodriguez, and M. Lavina. 2001. The structure, function, and origin of the microcin H47 ATP-binding cassette exporter indicate its relatedness to that of colicin V. Antimicrob. Agents Chemother. 45:969-972.
5. Bailey, J. E. 1993. Host-vector interactions in *Escherichia coli*, p. 29-77. In A. Fiechter (ed.), Advances in Biochemical Engineering. Biotechnology. Springer-Verlag, Berlin.
6. Barry, E. M., O. G. Gomez-Duarte, S. Chatfield, R. Rappuoli, M. Pizza, G. Losonsky, J. E. Galen, and M. M. Levine. 1996. Expression and immunogenicity of pertussis toxin 51 subunit-tetanus toxin fragment C fusions in *Salmonella* typhi vaccine strain CVD 908. Infect. Immun. 64:4172-4181.
7. Baumler, A. J., J. G. Kusters, I. Stojiljkovic, and F. Heffron. 1994. *Salmonella* typhimurium loci involved in survival within macrophages. Infect. Immun. 62:1623-1630.
8. Blomfield, I. C., V. Vaughn, R. F. Rest, and B. I. Eisenstein. 1991. Allelic exchange in *Escherichia coli* using the *Bacillus subtilis* sacB gene and a temperature-sensitive p5C101 replicon. Mol. Microbiol. 5:1447-1457.
9. Boe, L., K. Gerdes, and S. Molin. 1987. Effects of genes exerting growth inhibition and plasmid stability on plasmid maintenance. J. Bacteriol. 169:4646-4650.
10. Bouvier, J., C. Richaud, W. Higgins, O. Bogler, and P. Stragier. 1992. Cloning, characterization, and expression of the dapE gene of *Escherichia coli*. J. Bacteriol. 174:5265-5271.
11. Brandsma, J., D. Bosch, M. de Ruyter, and P. van de Putte. 1985. Analysis of the regulatory region of the ssb gene of *Escherichia coli*. Nucleic Acids Res. 13:5095-5109.
12. Brossier, F., M. Weber-Levy, M. Mock, and J. C. Sirard. 2000. Role of toxin functional domains in anthrax pathogenesis. Infect. Immun. 68:1781-1786.
13. Burrus, V. and M. K. Waldor. 2004. Shaping bacterial genomes with integrative and conjugative elements. Res. Microbiol. 155:376-386.
14. Carlini, L. E., R. D. Porter, U. Curth, and C. Urbanke. 1993. Viability and preliminary in vivo characterization of site-specific mutants of *Escherichia coli* single-stranded DNA-binding protein. Mol. Microbiol. 10:1067-1075.
15. Carter, P. B. and F. M. Collins. 1974. Growth of typhoid and paratyphoid bacilli in intravenously infected mice. Infect. Immun. 10:816-822.
16. Cerin, H. and J. Hackett. 1989. Molecular cloning and analysis of the incompatibility and partition functions of the virulence plasmid of *Salmonella* typhimurium. Microb. Pathog. 7:85-99.
17. Chase, J. W., J. B. Murphy, R. F. Whittier, E. Lorensen, and J. J. Sninsky. 1983. Amplification of ssb-1 mutant single-stranded DNA-binding protein in *Escherichia coli*. J. Mol. Biol. 163, 164:193-211.
18. Chase, J. W. and K. R. Williams. 1986. Single-stranded DNA binding proteins required for DNA replication. Annu. Rev. Biochem. 55:103-136.
19. Chatfield, S., K. Strahan, D. Pickard, I. G. Charles, C. E. Hormaeche, and G. Dougan. 1992. Evaluation of *Salmonella* typhimurium strains harbouring defined mutations in htrA and aroA in the murine salmonellosis model. Microb. Pathog. 12:145-151.
20. Chatfield, S, N., I. G. Charles, A. J. Makoff, M. D. Oxer, G. Dougan, D. Pickard, D. Slater, and N. F. Fairweather. 1992. Use of the nirB promoter to direct the stable expression of heterologous antigens in *Salmonella* oral vaccine strains: development of a single-dose oral tetanus vaccine. Biotechnology (NY) 10:888-892.
21. Chatfield, S. N., N. F. Fairweather, I. G. Charles, D. Pickard, M. M. Levine, D. M. Hone, M. Posada, R. A. Strugnell, and G. Dougan. 1992. Construction of a genetically defined *Salmonella* typhi Ty2 aroA, aroC mutant for the engineering of a candidate oral typhoid-tetanus vaccine. Vaccine 10:53-60.
22. Collier, R. J. and J. A. Young. 2003. Anthrax toxin. Annu. Rev. Cell Dev. Biol. 19:45-70.
23. Cordoba-Rodriguez, R., H. Fang, C. S. Lankford, and D. M. Frucht. 2004. Anthrax lethal toxin rapidly activates caspase-1/ICE and induces extracellular release of interleukin (IL)-1beta and IL-18. J. Biol. Chem. 279:20563-20566.
24. Covone, M. G., M. Brocchi, E. Palla, W. D. da Silveira, R. Rappuoli, and C. L. Galeotti. 1998. Levels of expression and immunogenicity of attenuated *Salmonella enterica* serovar typhimurium strains expressing *Escherichia coli* mutant heat-labile enterotoxin. Infect. Immun. 66:224-231.
25. D'Costa, V. M., K. M. McGrann, D. W. Hughes, and G. D. Wright. 2006. Sampling the antibiotic resistome. Science. 311:374-377.
26. Danilevskaya, O. N. and A. I. Gragerov. 1980. Curing of *Escherichia coli* K12 plasmids by coumermycin. Mol. Gen. Genet. 178:233-235.
27. Datsenko, K. A. and B. L. Wanner. 2000. One-step inactivation of chromosomal genes in *Escherichia coli* K-12 using PCR products. Proc. Natl. Acad. Sci. U.S.A. 97:6640-6645.
28. Destoumieux-Garzon, D., J. Peduzzi, and S. Rebuffat. 2002. Focus on modified microcins: structural features and mechanisms of action. Biochimie. 84:511-519.
29. Edelman, R., K. Palmer, K. G. Russ, H. P. Secrest, J. A. L. Becker, S. A. Bodison, J. G. Perry, A. R. Sills, A. G. Barbour, C. J. Luke, M. S. Hanson, C. K. Stover, J. E. Burlein, G. P. Bansal, E. M. Connor, and S. Koenig. 1999. Safety and immunogenicity of recombinant Bacille Calmette-Guerin (rBCG) expressing *Borrelia burgdorferi* outer surface protein A (OspA) lipoprotein in adult volunteers: a candidate Lyme disease vaccine. Vaccine 17:904-914.
30. Eifler, N., M. Vetsch, M. Gregorini, P. Ringler, M. Chami, A. Philippsen, A. Fritz, S. A. Muller, R. Glockshuber, A. Engel, and U. Grauschopf. 2006. Cytotoxin ClyA from *Escherichia coli* assembles to a 13-meric pore independent of its redox-state. EMBO J. 25:2652-2661.
31. Ferguson, G. C., J. A. Heinemann, and M. A. Kennedy. 2002. Gene transfer between *Salmonella enterica* serovar *Typhimurium* inside epithelial cells. J. Bacteriol. 184:2235-2242.
32. Frana, T. S., S. A. Carlson, D. C. Rauser, B. D. Jones, B. J. Fergen, and R. W. Griffith. 2004. Effects of microcin 24-producing *Escherichia coli* on shedding and multiple-antimicrobial resistance of *Salmonella enterica* serotype typhimurium in pigs. Am. J. Vet. Res. 65:1616-1620.
33. Gaggero, C., F. Moreno, and M. Lavina. 1993. Genetic analysis of microcin H47 antibiotic system. J. Bacteriol. 175:5420-5427.
34. Galan, J. E., K. Nakayama, and R. Curtiss III. 1990. Cloning and characterization of the asd gene of *Salmonella* typhimurium: use in stable maintenance of recombinant plasmids in *Salmonella* vaccine strains. Gene 94:29-35.
35. Galen, J. E., L. Zhao, M. Chinchilla, J. Y. Wang, M. F. Pasetti, J. Green, and M. M. Levine. 2004. Adaptation of the endogenous *Salmonella enterica* serovar Typhi clyA-encoded hemolysin for antigen export enhances the immunogenicity of anthrax protective antigen domain 4 expressed by the attenuated live-vector vaccine strain CVD 908-htrA. Infect. Immun. 72:7096-7106.
36. Galen, J. E., O. G. Gomez-Duarte, G. Losonsky, J. L. Halpern, C. S. Lauderbaugh, S. Kaintuck, M. K. Reymann, and M. M. Levine. 1997. A murine model of intranasal immunization to assess the immunogenicity of attenuated *Salmonella* typhi live vector vaccines in stimulating serum antibody responses to expressed foreign antigens. Vaccine 15:700-708.
37. Galen, J. E., J. Nair, J. Y. Wang, S. S. Wasserman, M. K. Tanner, M. Sztein, and M. M. Levine. 1999. Optimization of plasmid maintenance in the attenuated live vector vaccine strain *Salmonella* typhi CVD 908-htrA. Infect. Immun. 67:6424-6433.
38. Gerichter, C. B. 1960. The dissemination of *Salmonella* typhi, S. paratyphi A, and S. paratyphi B through the organs of the white mouse by oral infection. J. Hyg. Camb. 58:307-319.
39. Gerichter, C. B. and D. L. Boros. 1962. Dynamics of infection of the blood stream and internal organs of white mice with *Salmonella* typhi by intraperitoneal injection. J. Hyg. Camb. 60:311-321.
40. Glick, B. R. 1995. Metabolic load and heterologous gene expression. Biotechnol. Adv. 13:247-261.
41. Gomez-Duarte, O. G., J. E. Galen, S, N. Chatfield, R. Rappuoli, L. Eidels, and M. M. Levine. 1995. Expression of fragment C of tetanus toxin fused to a carboxyl-terminal fragment of diphtheria toxin in *Salmonella* typhi CVD 908 vaccine strain. Vaccine 13:1596-1602.
42. Gonzalez, C., D. M. Hone, F. Noriega, C. O. Tacket, J. R. Davis, G. Losonsky, J. P. Nataro, S. Hoffman, A. Malik, E. Nardin, M. Sztein, D. G. Heppner, T. R. Fouts, A. Isibasi, and M. M. Levine. 1994. *Salmonella* typhi vaccine strain CVD 908 expressing the circumsporozoite protein of *Plasmodium falciparum*: strain construction and safety and immunogenicity in humans. J. Infect. Dis. 169:927-931.
43. Gootz, T. D. 2006. The forgotten Gram-negative bacilli: what genetic determinants are telling us about the spread of antibiotic resistance. Biochem. Pharmacol. 71:1073-1084.
44. Hoiseth, S. K. and B. A. Stocker. 1981. Aromatic-dependent *Salmonella* typhimurium are non-virulent and effective as live vaccines. Nature 291:238-239.
45. Hone, D. M., A. M. Harris, S. Chatfield, G. Dougan, and M. M. Levine. 1991. Construction of genetically defined double aro mutants of *Salmonella* typhi. Vaccine 9:810-816.
46. Hsu J. 1996. Sample size computations Multiple comparisons: theory and methods. Chapman and Hall/CRC, New York.
47. Karem, K. L., S. Chatfield, N. Kuklin, and B. T. Rouse. 1995. Differential induction of carrier antigen-specific immunity by *Salmonella* typhimurium live-vaccine strains after single mucosal or intravenous immunization of BALB/c mice. Infect. Immun. 63:4557-4563.
48. Kotton, C. N., A. J. Lankowski, N. Scott, D. Sisul, L. M. Chen, K. Raschke, G. Borders, M. Boaz, A. Spentzou, J. E. Galan, and E. L. Hohmann. 2006. Safety and immunogenicity of attenuated *Salmonella enterica* serovar *Typhimurium* delivering an HIV-1 Gag antigen via the *Salmonella* Type III secretion system. Vaccine.
49. Lee, C., J. Kim, S. G. Shin, and S. Hwang. 2006. Absolute and relative QPCR quantification of plasmid copy number in *Escherichia coli*. J. Biotechnol. 123:273-280.

50. Lee, C. L., D. S. Ow, and S. K. Oh. 2006. Quantitative real-time polymerase chain reaction for determination of plasmid copy number in bacteria. J. Microbiol. Methods. 65:258-267.

51. Levine, M. M., J. E. Galen, C. O. Tacket, E. M. Barry, M. F. Pasetti, and M. B. Sztein. 2004. Attenuated strains of *Salmonella enterica* serovar Typhi as live oral vaccines against typhoid fever, p. 479-486. In M. M. Levine, J. B. Kaper, R. Rappuoli, M. A. Liu, and M. F. Good (eds.), New generation vaccines. Marcel Dekker, Inc., New York.

52. Levine, M. M., J. B. Kaper, H. Lockman, R. E. Black, M. L. Clements, and S. Falkow. 1983. Recombinant DNA risk assessment studies in humans: efficacy of poorly mobilizable plasmids in biologic containment. J. Infect. Dis. 148: 699-709.

53. Levine, M. M., J. E. Galen, E. M. Barry, F. Noriega, S. Chatfield, M. Sztein, G. Dougan, and C. O. Tacket. 1996. Attenuated *Salmonella* as live oral vaccines against typhoid fever and as live vectors. J. Biotechnol. 44:193-196.

54. Lewis, R. T. 2002. Oral versus systemic antibiotic prophylaxis in elective colon surgery: a randomized study and meta-analysis send a message from the 1990s. Can. J. Surg. 45:173-180.

55. Licht, T. R., B. B. Christensen, K. A. Krogfelt, and S. Molin. 1999. Plasmid transfer in the animal intestine and other dynamic bacterial populations: the role of community structure and environment. Microbiology. 145:2615-2622.

56. Little, S. F., B. E. Ivins, P. F. Fellows, M. L. Pitt, S. L. Norris, and G. P. Andrews. 2004. Defining a serological correlate of protection in rabbits for a recombinant anthrax vaccine. Vaccine 22:422-430.

57. Lohman, T. M. and M. E. Ferrari. 1994. *Escherichia coli* single-stranded DNA-binding protein: multiple DNA-binding modes and cooperativities. Annu. Rev. Biochem. 63:527-570.

58. Maeda, S., M. Ito, T. Ando, Y. Ishimoto, Y. Fujisawa, H. Takahashi, A. Matsuda, A. Sawamura, and S. Kato. 2006. Horizontal transfer of nonconjugative plasmids in a colony biofilm of *Escherichia coli*. FEMS Microbiol. Lett. 255: 115-120.

59. Maeda, S., A. Sawamura, and A. Matsuda. 2004. Transformation of colonial *Escherichia coli* on solid media. FEMS Microbiol. Lett. 236:61-64.

60. Matthews, R. G. 1996. One-carbon metabolism, p. 600-611. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (eds.), *Escherichia coli* and *Salmonella*: cellular and molecular biology. ASM Press, Washington, D.C.

61. McDermott, P. J., P. Gowland, and P. C. Gowland. 1993. Adaptation of *Escherichia coli* growth rates to the presence of pBR322. Lett. Appl. Microbiol. 17:139-143.

62. Medaglini, D., G. Pozzi, T. P. King, and V. A. Fischetti. 1995. Mucosal and systemic immune responses to a recombinant protein expressed on the surface of the oral commensal bacterium *Streptococcus gordonii* after oral colonization. Proc. Natl. Acad. Sci. USA 92:6868-6872.

63. Nissen-Meyer, J. and I. F. Nes. 1997. Ribosomally synthesized antimicrobial peptides: their function, structure, biogenesis, and mechanism of action. Arch. Microbiol. 167:67-77.

64. Noriega, F., G. Losonsky, J. Y. Wang, S. B. Formal, and M. M. Levine. 1996. Further characterization of DaroA, DvirG *Shigella flexneri* 2a strain CVD 1203 as a mucosal *Shigella* vaccine and as a live vector vaccine for delivering antigens of enterotoxigenic *Escherichia coli*. Infect. Immun. 64:23-27.

65. O'Brien, A. D. 1982. Innate resistance of mice to *Salmonella* typhi infection. Infect. Immun. 38:948-952.

66. Orr, N., J. E. Galen, and M. M. Levine. 1999. Expression and immunogenicity of a mutant diphtheria toxin molecule, $CRM_{197}$, and its fragments in *Salmonella* typhi vaccine strain CVD 908-htrA. Infect. Immun. 67:4290-4294.

67. Pallen, M. J. and B. W. Wren. 1997. The HtrA family of serine proteases. Mol. Microbiol. 26:209-221.

68. Papagianni, M. 2003. Ribosomally synthesized peptides with antimicrobial properties: biosynthesis, structure, function, and applications. Biotechnol. Adv. 21:465-499.

69. Patzer, S. I., M. R. Baquero, D. Bravo, F. Moreno, and K. Hantke. 2003. The colicin G, H and X determinants encode microcins M and 1147, which might utilize the catecholate siderophore receptors FepA, Cir, Fiu and IroN. Microbiology. 149:2557-2570.

70. Pecota, D.C., C. S. Kim, K. Wu, K. Gerdes, and T. K. Wood. 1997. Combining the hok/sok, parDE, and pnd postsegregational killer loci to enhance plasmid stability. Appl. Environ. Microbiol. 63:1917-1924.

71. Petosa, C., R. J. Collier, K. R. Klimpel, S. H. Leppla, and R. C. Liddington. 1997. Crystal structure of the anthrax toxin protective antigen. Nature 385:833-838.

72. Phipps, A. J., C. Premanandan, R. E. Barnewall, and M. D. Lairmore. 2004. Rabbit and nonhuman primate models of toxin-targeting human anthrax vaccines. Microbiol. Mol. Biol. Rev. 68:617-629.

73. Pickett, T. E., M. F. Pasetti, J. E. Galen, M. B. Sztein, and M. M. Levine. 2000. In vivo characterization of the murine intranasal model for assessing the immunogenicity of attenuated *Salmonella enterica* serovar Typhi strains as live mucosal vaccines and as live vectors. Infect. Immun. 68:205-213.

74. Pitt, M. L., S. Little, B. E. Ivins, P. Fellows, J. Boles, J. Barth, J. Hewetson, and A. M. Friedlander. 1999. In vitro correlate of immunity in an animal model of inhalational anthrax. J. Appl. Microbiol. 87:304.

75. Pittard, A. J. 1996. Biosynthesis of the aromatic amino acids, p. 458-484. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (eds.), *Escherichia coli* and *Salmonella*: cellular and molecular biology. ASM Press, Washington, D.C.

76. Pittman, P. R., S. L. Norris, J. G. Barrera Oro, D. Bedwell, T. L. Cannon, and K. T. McKee, Jr. 2006. Patterns of antibody response in humans to the anthrax vaccine adsorbed (AVA) primary (six-dose) series. Vaccine. 24:3654-3660.

77. Poey, M. E., M. F. Azpiroz, and M. Lavina. 2006. Comparative analysis of chromosome-encoded microcins. Antimicrob. Agents Chemother. 50:1411-1418.

78. Pons, A. M., I. Lanneluc, G. Cottenceau, and S. Sable. 2002. New developments in non-post translationally modified microcins. Biochimie. 84:531-537.

79. Porter, R. D., S. Black, S. Pannuri, and A. Carlson. 1990. Use of the *Escherichia coli* ssb gene to prevent bioreactor takeover by plasmidless cells. Bio/Technology 8:47-51.

80. Quinn, C. P., P. M. Dull, V. Semenova, H. Li, S. Crotty, T. H. Taylor, E. Steward-Clark, K. L. Stamey, D. S. Schmidt, K. W. Stinson, A. E. Freeman, C. M. Elie, S. K. Martin, C. Greene, R. D. Aubert, J. Glidewell, B. A. Perkins, R. Ahmed, and D. S. Stephens. 2004. Immune responses to

*Bacillus anthracis* protective antigen in patients with bioterrorism-related cutaneous or inhalation anthrax. J. Infect. Dis. 190:1228-1236.
81. Rodriguez, E., C. Gaggero, and M. Lavina. 1999. The structural gene for microcin 1147 encodes a peptide precursor with antibiotic activity. Antimicrob. Agents Chemother. 43:2176-2182.
82. Rodriguez, E. and M. Lavina. 1998. Genetic analysis of microcin 1147 immunity. Can. J. Microbiol. 44:692-697.
83. Rodriguez, E. and M. Lavina. 2003. The proton channel is the minimal structure of ATP synthase necessary and sufficient for microcin h47 antibiotic action. Antimicrob. Agents Chemother. 47:181-187.
84. Ryan, E. T., J. R. Butterton, T. Zhang, M. A. Baker, S. L. Jr. Stanley, and S. B. Calderwood. 1997. Oral immunization with attenuated vaccine strains of *Vibrio cholerae* expressing a dodecapeptide repeat of the serine-rich *Entamoeba histolytica* protein fused to the cholera toxin B subunit induces systemic and mucosal antiamebic and anti-*V. cholerae* antibody responses in mice. Infect. Immun. 65:3118-3125.
85. Salerno-Goncalves, R., T. L. Wyant, M. F. Pasetti, M. Fernandez-Vina, C. O. Tacket, M. M. Levine, and M. B. Sztein. 2003. Concomitant induction of CD4+ and CD8+ T cell responses in volunteers immunized with *Salmonella enterica* serovar typhi strain CVD 908-htrA. J. Immunol. 170:2734-2741.
86. Salyers, A. A. and C. F. Amabile-Cuevas. 1997. Why are antibiotic resistance genes so resistant to elimination? Antimicrob. Agents Chemother. 41:2321-2325.
87. Salyers, A. A., A. Gupta, and Y. Wang. 2004. Human intestinal bacteria as reservoirs for antibiotic resistance genes. Trends Microbiol. 12:412-416.
88. Schippers, E. F. and J. T. van Dissel. 2003. Selective gut decontamination. Crit. Care Med. 31:2715-2716.
89. Schodel, F., S. M. Kelly, S. A. Tinge, S. Hopkins, D. L. Peterson, D. R. Milich, and R. Curtiss III. 1996. Hybrid hepatitis B virus core antigen as a vaccine carrier moiety. II. Expression in avirulent *Salmonella* spp. for mucosal immunization. Adv. Exp. Med. Biol. 397:15-21.
90. Smith, M. A. and M. J. Bidochka. 1998. Bacterial fitness and plasmid loss: the importance of culture conditions and plasmid size. Can. J. Microbiol. 44:351-355.
91. Sorensen, S. J., M. Bailey, L. H. Hansen, N. Kroer, and S. Wuertz. 2005. Studying plasmid horizontal transfer in situ: a critical review. Nat. Rev. Microbiol. 3:700-710.
92. Souders, N.C., T. Verch, and Y. Paterson. 2006. In vivo bactofection: listeria can function as a DNA-cancer vaccine. DNA Cell Biol. 25:142-151.
93. Srinivasan, J., S. A. Tinge, R. Wright, J. C. Herr, and R. Curtiss III. 1995. Oral immunization with attenuated *Salmonella* expressing human sperm antigen induces antibodies in serum and the reproductive tract. Biol. Reprod. 53:462-471.
94. Summers, D. K. 1998. Timing, self-control and sense of direction are the secrets of multicopy plasmid stability. Mol. Microbiol. 29:1137-1145.
95. Tacket, C. O., J. Galen, M. B. Sztein, G. Losonsky, T. L. Wyant, J. Nataro, S. S. Wasserman, R. Edelman, S. Chatfield, G. Dougan, and M. M. Levine. 2000. Safety and immune responses to attenuated *Salmonella enterica* serovar Typhi oral live vector vaccines expressing tetanus toxin fragment C. Clin Immunol. 97:146-153.
96. Tacket, C. O., D. M. Hone, R. Curtiss III, S. M. Kelly, G. Losonsky, L. Guers, A. M. Harris, R. Edelman, and M. M. Levine. 1992. Comparison of the safety and immunogenicity of DaroCDaroD and DcyaDcrp *Salmonella* typhi strains in adult volunteers. Infect. Immun. 60:536-541.
97. Tacket, C. O., S. M. Kelley, F. Schodel, G. Losonsky, J. P. Nataro, R. Edelman, M. M. Levine, and R. Curtiss III. 1997. Safety and immunogenicity in humans of an attenuated *Salmonella* typhi vaccine vector strain expressing plasmid-encoded hepatitis B antigens stabilized by the Asd-balanced lethal vector system. Infect. Immun. 65:3381-3385.
98. Tacket, C. O., M. Sztein, G. Losonsky, S. S. Wasserman, J. P. Nataro, R. Edelman, D. Pickard, G. Dougan, S. Chatfield, and M. M. Levine. 1997. Safety of live oral *Salmonella* typhi vaccine strains with deletions in htrA and aroC aroD and immune responses in humans. Infect. Immun. 65:452-456.
99. Tacket, C. O., M. Sztein, S. S. Wasserman, G. Losonsky, K. Kotloff, T. L. Wyant, J. P. Nataro, R. Edelman, J. G. Perry, P. Bedford, D. Brown, S. Chatfield, G. Dougan, and M. M. Levine. 2000. Phase 2 clinical trial of attenuated *Salmonella enterica* serovar Typhi oral live vector vaccine CVD 908-htrA in U.S. volunteers. Infect. Immun. 68:1196-1201.
100. Tinge, S. A. and R. Curtiss III. 1990. Conservation of *Salmonella* typhimurium virulence plasmid maintenance regions among *Salmonella* serovars as a basis for plasmid curing. Infect. Immun. 58:3084-3092.
101. Tinge, S. A. and R. Curtiss III. 1990. Isolation of the replication and partitioning regions of the *Salmonella* typhimurium virulence plasmid and stabilization of heterologous replicons. J. Bacteriol. 172:5266-5277.
102. Trujillo, M., E. Rodriguez, and M. Lavina. 2001. ATP synthase is necessary for microcin 1147 antibiotic action. Antimicrob. Agents Chemother. 45:3128-3131.
103. Umbarger, H. E. 1978. Amino acid biosynthesis and its regulation. Annu. Rev. Biochem. 47:533-606.
104. Valenzuela, M. S., K. A. Siddiqui, and B. L. Sarkar. 1996. High expression of plasmid-encoded tetracycline resistance gene in *E. coli* causes a decrease in membrane-bound ATPase activity. Plasmid. 36:19-25.
105. Varughese, M., A. V. Teixeira, S. Liu, and S. H. Leppla. 1999. Identification of a receptor-binding region within domain 4 of the protective antigen component of anthrax toxin. Infect. Immun. 67:1860-1865.
106. Wai, S. N., B. Lindmark, T. Soderblom, A. Takade, M. Westermark, J. Oscarsson, J. Jass, A. Richter-Dahlfors, Y. Mizunoe, and B. E. Uhlin. 2003. Vesicle-mediated export and assembly of pore-forming oligomers of the enterobacterial ClyA cytotoxin. Cell 115:25-35.
107. Wallace, A. J., T. J. Stillman, A. Atkins, S. J. Jamieson, P. A. Bullough, J. Green, and P. J. Artymiuk. 2000. *E. coli* hemolysin E (HlyE, ClyA, SheA): X-ray crystal structure of the toxin and observation of membrane pores by electron microscopy. Cell 100:265-276.
108. Wang, J. Y., F. Noriega, J. E. Galen, E. M. Barry, and M. M. Levine. 2000. Constititive expression of the Vi polysaccharide capsular antigen in attenuated *Salmonella enterica* serovar Typhi oral vaccine strain CVD 909. Infect. Immun. 68:4647-4652.
109. Wang, J. Y., M. F. Pasetti, F. Noriega, R. J. Anderson, S. S. Wasserman, J. E. Galen, M. Sztein, and M. M. Levine. 2001. Construction, genotypic and phenotypic characterization, and immunogenicity of attenuated DguaBA *Salmonella enterica* serovar Typhi strain CVD 915. Infect. Immun. 69:4734-4741.
110. Williams, K. R., J. B. Murphy, and J. W. Chase. 1984. Characterization of the structural and functional defect in the *Escherichia coli* single-stranded DNA binding protein encoded by the ssb-1 mutant gene. J. Biol. Chem. 259: 11804-11811.
111. Wu, K. and T. K. Wood. 1994. Evaluation of the hok/sok killer locus for enhanced plasmid stability. Biotechnol. Bioeng. 44:912-921.
112. Zalkin, H. and P. Nygaard. 1996. Biosynthesis of purine nucleotides, p. 561-579. In F. C. Neidhardt, J. L. Ingraham, E. C. C. Lin, K. B. Low, B. Magasanik, W. S. Reznikoff, M. Riley, M. Schaechter, and H. E. Umbarger (eds.), *Escherichia coli* and *Salmonella*: cellular and molecular biology. ASM Press, Washington, D.C.
113. Zegers, N. D., E. Kluter, S. H. Van Der, E. Van Dura, P. Van Dalen, M. Shaw, and L. Baillie. 1999. Expression of the protective antigen of *Bacillus anthracis* by *Lactobacillus casei*: towards the development of an oral vaccine against anthrax. J. Appl. Microbiol. 87:309-314.

What is claimed is:

1. An expression vector comprising a nucleotide sequence encoding:
   (a) a restricted-copy-number origin of replication cassette comprising
      (i) a nucleotide sequence encoding an origin of replication that limits the expression vector to an average plasmid copy number of about 2 to 75 copies per cell,
      (ii) a first unique restriction enzyme cleavage site located 5' of the nucleotide sequence encoding the origin of replication, and
      (iii) a second unique restriction enzyme cleavage site located 3' of the nucleotide sequence encoding the origin of replication;
   (b) at least one post-segregational killing cassette comprising
      (i) a nucleotide sequence encoding at least one post-segregational killing locus,
      (ii) a third unique restriction enzyme cleavage site located 5' of the nucleotide sequence encoding the at least one post-segregational killing locus, and
      (iii) a fourth unique restriction enzyme cleavage site located 3' of the nucleotide sequence encoding the at least one post-segregational killing locus;
   (c) at least one partitioning cassette comprising
      (i) a nucleotide sequence encoding at least one partitioning function,
      (ii) a fifth unique restriction enzyme cleavage site 5' of the nucleotide sequence encoding the at least one partitioning function, and
      (iii) a sixth unique restriction enzyme cleavage site located 3' of the nucleotide sequence encoding the at least one partitioning function; and
   (d) at least one selectable marker cassette comprising
      (i) a nucleotide sequence encoding at least one selectable marker, wherein said selectable marker is the *E. coli* polypeptide mchI having the amino acid sequence set forth in SEQ ID NO:30
      (ii) a seventh unique restriction enzyme cleavage site located 5' of the nucleotide sequence encoding the at least one selectable marker, and
      (iii) an eighth unique restriction enzyme cleavage site located 3' of the nucleotide sequence encoding the at least one selectable marker.

2. The expression vector of claim 1, wherein the nucleotide sequence encoding an origin of replication is a nucleotide sequence selected from the group consisting of the oriE1 sequence set forth in SEQ ID NO:1, the ori101 sequence set forth in SEQ ID NO:3, and the ori15A sequence set forth in SEQ ID NO:2.

3. The expression vector of claim 1, wherein the nucleotide sequence encoding at least one post-segregational killing locus is a nucleotide sequence selected from the group consisting of a nucleotide sequence encoding the ssb post-segregational killing locus, a nucleotide sequence encoding the asd balanced-lethal system, a nucleotide sequence encoding the phd-doc proteic system, and a nucleotide sequence encoding the hok-sok antisense system.

4. The expression vector of claim 1, wherein said nucleotide sequence encoding at least one post-segregational killing locus is a nucleotide sequence encoding the ssb post-segregational killing locus.

5. The expression vector of claim 4, wherein said ssb post-segregational killing locus comprises a ssb inducible promoter, a ssb constitutive promoter and a ssb coding region, and wherein said locus is the ssb post-segregational killing locus of *Shigella flexneri, Salmonella* Typhi or *E. coli*.

6. The expression vector of claim 4, wherein said ssb post-segregational killing locus comprises the ssb inducible promoter, the ssb constitutive promoter and the ssb coding region of *Shigella flexneri* 2a strain CVD 1208s as set forth in SEQ ID NO:4.

7. The expression vector of claim 1, wherein the nucleotide sequence encoding at least one post-segregational killing locus is a homolog of a ssb post-segregational killing locus, wherein said homolog has at least 90% identity over its entire length to the ssb post-segregational killing locus set forth in SEQ ID NO:4, wherein both the inducible and constitutive promoters of said homolog have promoter activity, and wherein the SSB polypeptide encoded by said homolog has DNA binding and DNA replication activity.

8. The expression vector of claim 1, wherein the partitioning function is an active partitioning function.

9. The expression vector of claim 1, wherein the nucleotide sequence encoding at least one partitioning function comprises *Escherichia coli* parA set forth in SEQ ID NO:5.

10. The expression vector of claim 1, wherein the nucleotide sequence encoding at least one partitioning function is the par locus of *Escherichia coli* pSC101 set forth in SEQ ID NO:6.

11. The expression vector of claim 1, wherein the average plasmid copy-number is about 5 to about 60 copies per cell.

12. The expression vector of claim 1, further comprising
   (e) an expression cassette comprising
      (i) a nucleotide sequence encoding a promoter,
      (ii) a ninth unique restriction enzyme cleavage site located 5' of the nucleotide sequence encoding the promoter, and
      (iii) a tenth unique restriction enzyme cleavage site located 3' of the nucleotide sequence encoding the promoter.

13. The expression vector of claim 12, wherein the promoter (e)(i) is an inducible promoter.

14. The expression vector of claim 13, wherein the promoter (e)(i) is an ompC promoter.

15. The expression vector of claim 13, wherein the promoter (e)(i) is the ompC promoter set forth in SEQ ID NO:7.

16. The expression vector of claim 12, wherein said expression cassette (e) further comprises a nucleotide sequence encoding an antigen positioned at the 3' end of the nucleotide sequence encoding promoter (e)(i), wherein expression of said antigen is under control of said promoter (e)(i).

17. The expression vector of claim 16, wherein the antigen is selected from the group consisting of a viral antigen, a bacterial antigen, a cancer antigen, and an auto-immune antigen.

18. The expression vector of claim 16, wherein the antigen is selected from the group consisting of a domain of the anthrax toxin Protective Antigen PA83 moiety, full-length PA83 or the 63 kDa biologically active form of PA83.

19. The expression vector of claim 17, wherein the antigen is domain 4 of the anthrax toxin Protective Antigen PA83 set forth in SEQ ID NO:36.

20. The expression vector of claim 16, wherein the antigen is a fragment of a *Clostridium botulinum* neurotoxin eukaryotic cell-binding heavy chain or a fusion protein consisting of fragments of said heavy chain, wherein said heavy chain is a heavy chain of a *Clostridium botulinum* serotype selected from the group consisting of *Clostridium botulinum* serotypes A, B, C, D, E, F and G.

21. An isolated cell comprising the expression vector of claim 1.

22. The isolated cell of claim 21, wherein the isolated cell is a bacterial cell.

23. The isolated cell of claim 22, wherein the isolated cell is a *Salmonella* Typhi cell.

24. The isolated cell of claim 21, wherein the isolated cell is a cell of a bacterial strain selected from the group consisting of *Shigella flexneri* 2a strain CVD 1208s, *Salmonella enterica* serovar Typhi strain CVD 908-htrA, *Salmonella enterica* serovar Typhi strain CVD 909, and *E. coli* strain DH5 alpha.

25. The isolated cell of claim 22, wherein the endogenous ssb gene of said bacterial cell is inactivated or deleted.

26. The isolated cell of claim 23, wherein the endogenous ssb gene of said *Salmonella* Typhi cell is inactivated or deleted.

27. The isolated cell of claim 24, wherein the endogenous ssb gene of said cell of a bacterial strain is inactivated or deleted.

28. The isolated cell of claim 23, wherein said cell is *Salmonella enterica* serovar Typhi strain CVD 908-htrAssb.

* * * * *

UNITED STATES PATENT AND TRADEMARK OFFICE
CERTIFICATE OF CORRECTION

PATENT NO.         : 8,728,760 B2
APPLICATION NO.    : 12/531714
DATED              : May 20, 2014
INVENTOR(S)        : James E. Galen et al.

It is certified that error appears in the above-identified patent and that said Letters Patent is hereby corrected as shown below:

In the Specification

Column 1, lines 4-6, cancel the two sentences beginning with "This invention was made with" and ending with "certain rights in this invention." and insert the following heading and two sentences.

--STATEMENT REGARDING FEDERALLY SPONSORED RESEARCH
This invention was made with government support under Grant Numbers AI057168 and AI025461 awarded by the National Institutes of Health. The government has certain rights in the invention.--

Signed and Sealed this
Seventh Day of October, 2014

Michelle K. Lee
*Deputy Director of the United States Patent and Trademark Office*